US011814407B2

(12) United States Patent
Hansen et al.

(10) Patent No.: US 11,814,407 B2
(45) Date of Patent: *Nov. 14, 2023

(54) MULTIPLE COUPLING AND OXIDATION METHOD

(71) Applicant: Roche Innovation Center Copenhagen A/S, Horsholm (DK)

(72) Inventors: Dennis Jul Hansen, Farum (DK); Erik Daa Funder, Hilleroed (DK)

(73) Assignee: ROCHE INNOVATION CENTER COPENHAGEN A/S, Basel (CH)

( * ) Notice: Subject to any disclaimer, the term of this patent is extended or adjusted under 35 U.S.C. 154(b) by 59 days.

This patent is subject to a terminal disclaimer.

(21) Appl. No.: 16/617,279

(22) PCT Filed: Jun. 26, 2018

(86) PCT No.: PCT/EP2018/067015
§ 371 (c)(1),
(2) Date: Nov. 26, 2019

(87) PCT Pub. No.: WO2019/002237
PCT Pub. Date: Jan. 3, 2019

(65) Prior Publication Data
US 2020/0148714 A1    May 14, 2020

(30) Foreign Application Priority Data

Jun. 28, 2017 (EP) .................... 17178454

(51) Int. Cl.
*C07H 21/00* (2006.01)
*C07H 21/02* (2006.01)
(Continued)

(52) U.S. Cl.
CPC ............... *C07H 1/00* (2013.01); *C07H 21/00* (2013.01); *C07H 21/02* (2013.01); *C07H 21/04* (2013.01)

(58) Field of Classification Search
CPC combination set(s) only.
See application file for complete search history.

(56) References Cited

U.S. PATENT DOCUMENTS 8,859,755 B2    10/2014  Wada et al.
9,598,458 B2 *   3/2017  Shimizu ................. C07H 21/04
(Continued)

FOREIGN PATENT DOCUMENTS

EP       1984381       10/2008
EP       3645544 A1     5/2020
(Continued)

OTHER PUBLICATIONS

U.S. Appl. No. 17/241,535, filed Apr. 2021, Hanson et al.*
(Continued)

*Primary Examiner* — Eric Olson
(74) *Attorney, Agent, or Firm* — Smith, Gambrell & Russell; Judy Jarecki-Black

(57) ABSTRACT

The present invention relates to methods of synthesis of stereodefined oligonucleotides wherein the protected 5'-hydroxy terminus of a nucleoside or oligonucleotide attached to a solid support is first unprotected, followed by coupling an oxazaphospholidine phosphoramidite monomer to the now deprotected 5'-hydroxy terminus, oxidizing the resultant phosphite triester intermediate with a sulfurizing reagent, and optionally washing the product. The method of synthesis of the present invention described above may be repeated to optionally elongate the stereodefined oligonucleotide being synthesized until the elongation cycle is intentionally terminated via deprotecting and cleavaging the resulting stereodefined oligonucleotide from the solid support. The oxazaphospholidine phosphoramidite monomer to be coupled in the present invention may optionally be chosen from Formula 1a and 1b. Generally, the present invention relates to enhanced synthesis methods wherein a
(Continued)

Figure 3A:
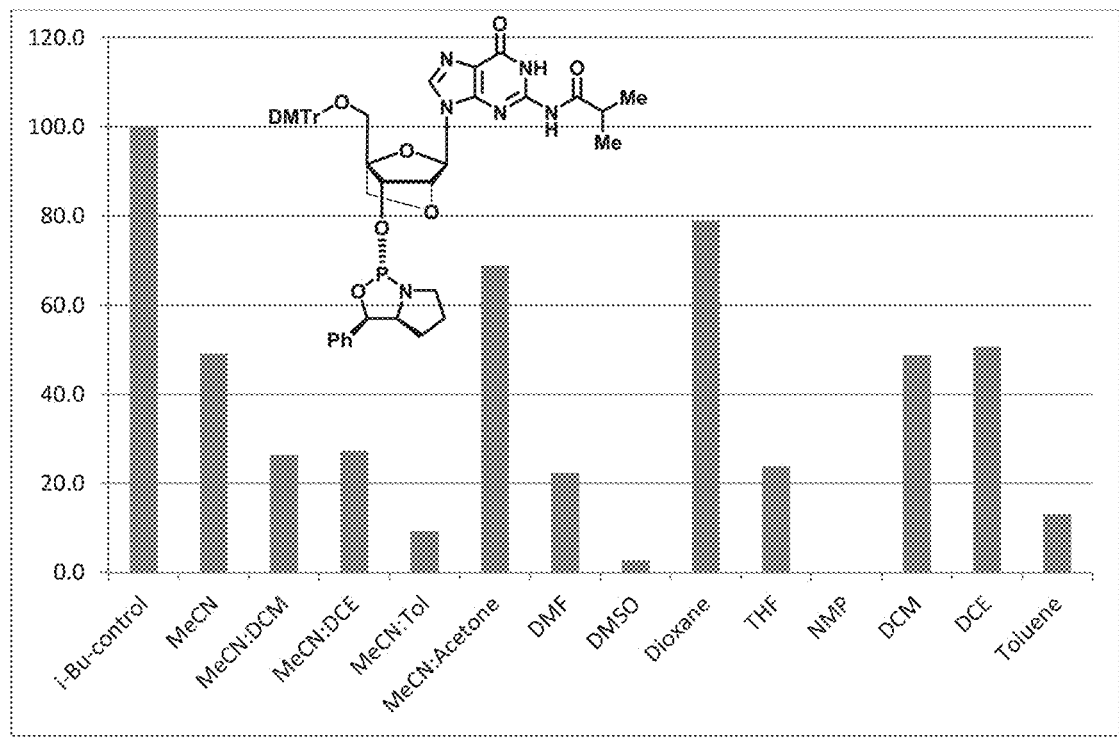

single elongation cycle, optionally comprising repeated coupling and oxidation steps, results in an enhanced yield and higher purity of stereodefined phosphorothioate oligonucleotides.

9 Claims, 23 Drawing Sheets

Specification includes a Sequence Listing.

(51) Int. Cl.
C07H 21/04 (2006.01)
C07H 1/00 (2006.01)

(56) References Cited

U.S. PATENT DOCUMENTS

| | | | | |
|---|---|---|---|---|
| 10,072,261 | B1* | 9/2018 | Myerson | C07H 21/00 |
| 10,167,309 | B2* | 1/2019 | Shimizu | C07H 19/10 |
| 10,696,711 | B2* | 6/2020 | Shimizu | C07H 1/00 |
| 11,261,209 | B2* | 3/2022 | Ravn | C07H 19/06 |
| 11,267,843 | B2* | 3/2022 | Albaek | C07H 19/16 |
| 2006/0247431 | A1 | 11/2006 | Wolter et al. | |
| 2015/0197540 | A1 | 7/2015 | Shimizu et al. | |
| 2019/0153012 | A1* | 5/2019 | Ravn | C07H 19/20 |
| 2021/0179658 | A1* | 6/2021 | Bleicher | C07H 19/10 |
| 2021/0355150 | A1* | 11/2021 | Hansen | C07H 19/06 |

FOREIGN PATENT DOCUMENTS

| | | | |
|---|---|---|---|
| JP | 2005-046073 A | 2/2005 | |
| WO | WO 98/16540 | 4/1998 | |
| WO | WO 2007/090071 | 8/2007 | |
| WO | WO 2007/112754 | 10/2007 | |
| WO | WO 2009/043353 | 4/2009 | |
| WO | WO 2009/124238 | 10/2009 | |
| WO | WO 2010/036698 | 4/2010 | |
| WO | 2011/108682 A1 | 9/2011 | |
| WO | WO 2014/010250 | 1/2014 | |
| WO | WO-2014012081 A2 * | 1/2014 | A61K 38/17 |
| WO | WO 2017/194498 | 11/2017 | |
| WO | WO 2018/177825 | 10/2018 | |

OTHER PUBLICATIONS

Bergstrom, "Unnatural Nucleosides with Unusual Base Bairing Properties," Current Protocols in Nucleic Acid Chemistiy Suppl., Jun. 2009, 37:1.4.1.-1.4.32.
Capaldi and Scozzari, "Manufacturing and Analytical Processes for 2'-O-(2-Methoxyethyl)-Modified Oligonucleotides," Antisense Drug Technology: Principles, Strategies, and Applications, CRC Press 2008, Chapter 14, 2 pages, Abstract Only.
Hirao et al., "Natural versus Artificial Creation of Base Pairs in DNA: Origin of Nucleobases from the Perspectives of Unnatural Base Pair Studies," Accounts of Chemical Research, Jan. 20, 2012, 45(12):2055-2065.
International Preliminary Report on Patentability in International Application No. PCT/EP2018/067015, dated Dec. 31, 2019, 8 pages.
International Search Report and Written Opinion in International Applciation No. PCT/EP2018/067015, dated Sep. 17, 2018, 11 pages.
Nukaga et al., "Stereocontrolled Solid-Phase Synthesis of Phosphorothioate Oligoribonucleotides Using 2'-0-(2-Cyanoethoxymethyl)-nucleoside 3'-0-Oxazaphospholidine Monomers," Journal of Organic Chemistry, 2012, 77(18):7913-7922.
Oka et al., "Solid-Phase Synthesis of Stereoregular Oligodeoxyribonucleoside Phosphorothioates Using Bicyclic Oxazaphospholidine Derivatives as Monomer Units," J. Am. Chem. Soc., Nov. 8, 2008, 130(47):16031-16037.
Ravikumar et al., "UnyLinker: An Efficient and scaleable synthesis of Oligonucleotides Utilizing a Universal Linker Molecule: A Novel Approach To Enhance the Purity of Drugs," Organic Process Research & Development, 2008, 12:399-410.
Seth at al., "Synthesis and Biophysical Evaluation of 2',4'-Constrained 2'O-Methoxyethyl and 2',4'-Constrained 2'O-Ethyl Nucleic Acid Analogues," J. Org. Chem., 2010, 75(5):1569-1581.
Wan et al., "Synthesis, biophysical properties and biological activity of second generation antisense oligonucleotides containing chiral phosphorothioate linkages," NAR, Nov. 14, 2014, 42(22):13456-13468.
Wan et al., "Synthesis, biophysical properties and biological activity of second generation antisense oligonucleotides containing chiral phosphorothioate linkages," NAR, 2014, 42(22):13466 Supplementary Information.
Hyodo, M., et al., "Utility of Azolium Tritiates as Promotors for the Condensation of a Nucleoside Phosphoramidite and a Nucleoside in the Agrawal's Stereoselective Synthesis of Nucleoside Phosphorothioates", Eur. J. Chem., 5216-5223 (2005).
Lyer, R.P.,et al, "Solid-Phase Stereoselective Synthesis of Oligonucleoside Phosphorothioates: The Nucleoside Bicyclic Oxazaphospholidines as Novel Synthons", Tetrahedron Lett., 39: 2491-2494 (1998).
Notice of Reasons for Rejection received for Japanese patent Application No. 2019-572465, dated Jul. 11, 2022, 10 pages (5 pages of English Translation and 5 pages of Original Document).
Nukaga, Y. et al., "Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method", Journal of Organic Chemistry , 2016, 81(7): 2753-2762.
Oka, N., et al., "Diastereocontrolled Synthesis of Dinucleoside Phosphorothioates Using a Novel Class of Activators, Dialkyl(cyanomethyl)ammonium Tetrafluoroborates", J. Am. Chem. Soc., 124: 4962-4963 (2002).
Oka, N., et al., "Diastereocontrolled Synthesis of Phosphorothioate DNA via an Oxazaphospholidine Approach Using a Novel Class of Activators, Dialkyl(cyanomethyl)ammonium Salts", Nucleosides, Nucleotides & Nucleic Acids, 22: 1411-1413(2003).
Oka, N., et al., "Stereocontrolled Synthesis of Oligoribonucleoside Phosphorothioates by an Oxazaphospholidine Approach", Orig. Lett., 11: 967-970 (2009).
Oka, N., et al., "An Oxazaphospholidine Approach for the Stereocontrolled Synthesis of Oligonucleoside Phosphorothioates", J. of the American Chem. Soc., 125(27): 8307-8317 (2003).
Wan, W. B. et al., "Supplementary Information Synthesis, Biophysical Properties and Biological Activity of Second Generation Antisense Oligonucleotides Containing Chiral Phosphorothioate Linkages", Nucleicacids Research, vol. 42, No. 22, Nov. 14, 2014, pp. 13466.
Office Action received for Chinese Patent Application No. 201880043406.4, dated Nov. 1, 2022, 13 pages (4 pages of English Translation and 9 pages of Original Document).
Communication under Rule 161/162 received on Feb. 6, 2020 for EP 18734530, 3 Pages.
Intention to grant received for European Application No. 18734530.1, dated Jan. 4, 2023, 9 pages.
Reply to Communication under Rule 161/162 dated Jul. 10, 2020 for EP 18734530.1, 7 Pages.

* cited by examiner

| Stability at 24 hours | MeCN | MeCN/ DCM (1:1) | MeCN/ DCE (1:1) | MeCN/ Toluene (1:1) | MeCN/ Acetone (1:1) | DMF | DMSO | Dioxane | THF | NMP | DCM | DCE | Toluene |
|---|---|---|---|---|---|---|---|---|---|---|---|---|---|
| D-LNA A-DMF | 2 | 3 | 3 | 3 | 2 | 3 | 3 | 2 | 1 | 3 | 3 | 3 | 3 |
| L-LNA A-DMF | 3 | 3 | 3 | 2 | 2 | 3 | 3 | 1 | 1 | 3 | 1 | 1 | 3 |
| D-LNA T-DMF | 1 | 1 | 1 | 2 | 2 | 2 | 3 | 2 | 1 | 3 | 3 | 1 | 3 |
| L-LNA T-DMF | 1 | 3 | 1 | 2 | 2 | 1 | 2 | 1 | 1 | 2 | 1 | 1 | 3 |
| D-LNA C-DMF | 3 | 3 | 3 | 3 | 3 | 3 | 3 | 3 | 2 | 3 | 2 | 3 | 3 |
| L-LNA C-DMF | 2 | 2 | 1 | 3 | 3 | 1 | 1 | 1 | 1 | 3 | 1 | 2 | 3 |
| D-LNA G-DMF | 1 | 1 | 1 | 3 | 3 | 3 | 3 | 1 | 2 | 3 | 3 | 3 | 3 |
| L-LNA G-DMF | Not soluble | 3 | Not soluble | Not soluble | Not soluble | 3 | 3 | Not soluble | Not soluble | 3 | 3 | 3 | Not soluble |
| L-LNA G-4Bn | 2 | 2 | 2 | 3 | 2 | 3 | 3 | 1 | 2 | n/a | 2 | 2 | 3 |
| D-DNA A-DMF | 3 | 3 | 3 | 3 | 3 | 3 | 3 | 2 | 2 | 3 | 2 | 2 | 3 |
| L-DNA A-DMF | 3 | 1 | 3 | 3 | 3 | 3 | 3 | 1 | 2 | 3 | 2 | 2 | 3 |
| D-DNA T-DMF | 3 | 3 | 3 | 3 | 3 | 2 | 3 | 2 | 1 | 3 | 1 | 1 | 3 |
| L-DNA T-DMF | 3 | 1 | 2 | 3 | 1 | 3 | 3 | 1 | 2 | 3 | 1 | 1 | 3 |
| D-DNA C-DMF | 2 | 2 | 2 | 3 | 2 | 3 | 3 | 1 | 1 | 3 | 1 | 1 | 3 |
| L-DNA C-DMF | 3 | 3 | 3 | 3 | 3 | 3 | 3 | 2 | 3 | 3 | n/a | n/a | 3 |
| D-DNA G-DMF | 3 | 3 | 3 | 3 | 3 | 3 | 3 | 2 | 3 | n/a | n/a | n/a | 3 |

FIG. 1

Solubility 0 h

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | no | no | no | yes | yes | no | no | yes | yes | no | no |
| L-LNA G-i-Bu | yes | yes | yes | yes | yes | yes | yes | yes | yes | n/a | yes | yes | yes |

Solubility 24 h

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | yes | no | no | yes | yes | no | no | no | yes | yes | no |
| L-LNA G-i-Bu | no | no | no | no | yes | yes | no | yes | yes | n/a | yes | yes | yes |

FIG. 2

FIG. 14
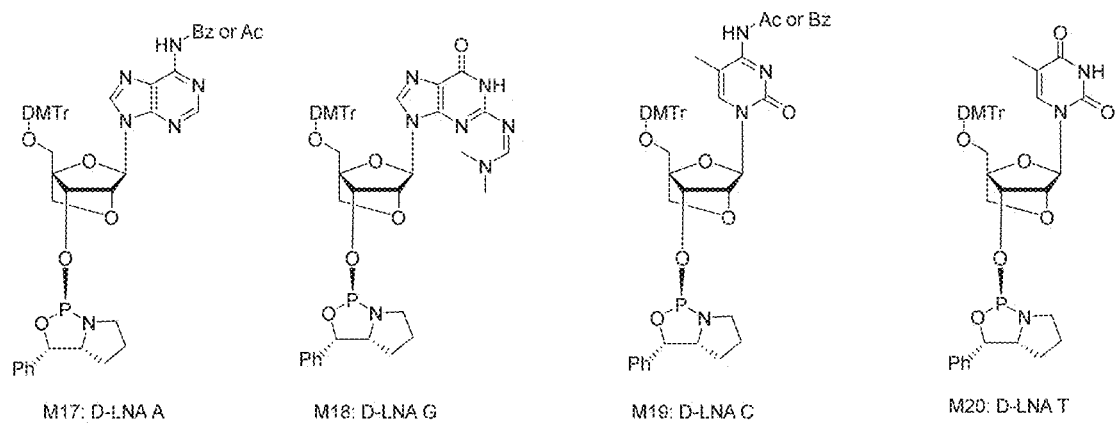
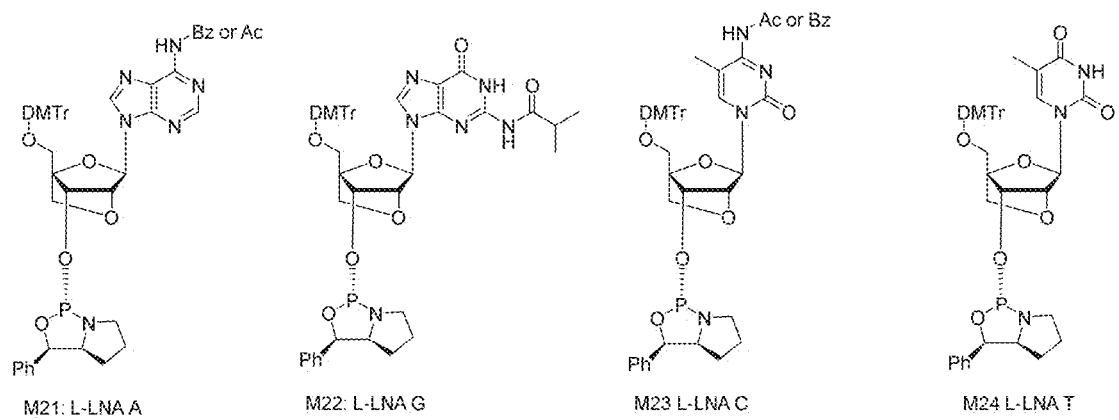

FIG. 17
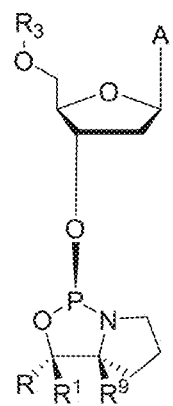 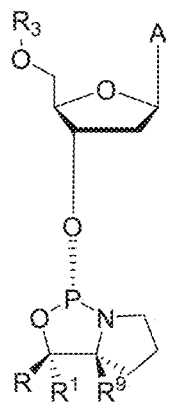 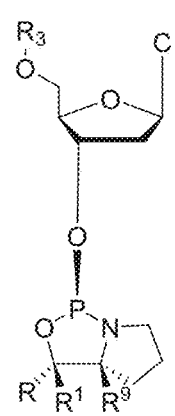 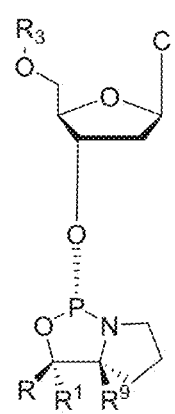
Formula 33    Formula 34    Formula 35    Formula 36
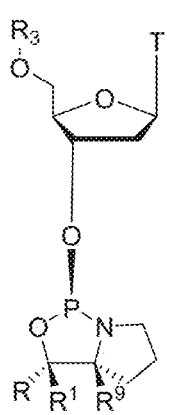 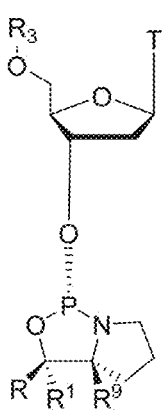 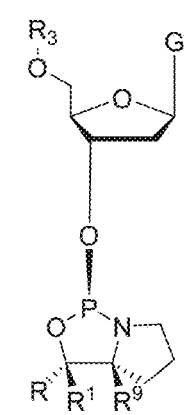 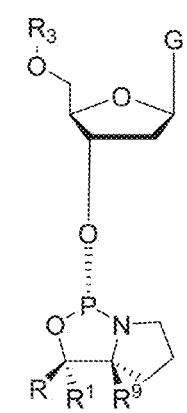
Formula 37    Formula 38    Formula 39    Formula 40

FIG. 18
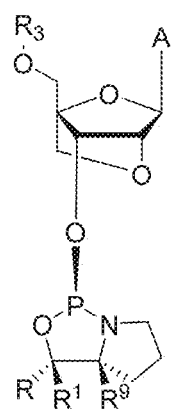
Formula 41
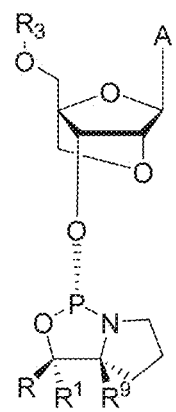
Formula 42
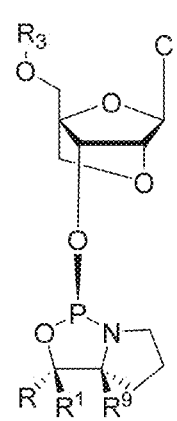
Formula 43
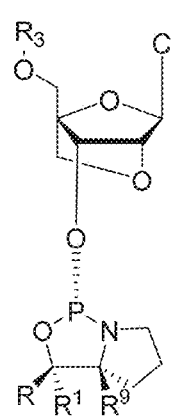
Formula 44
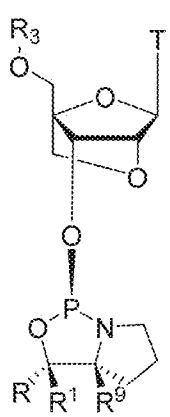
Formula 45
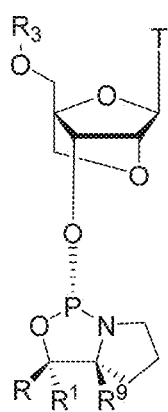
Formula 46
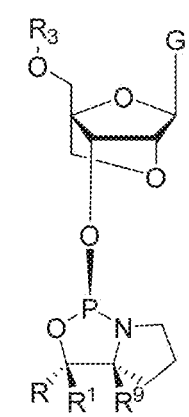
Formula 47
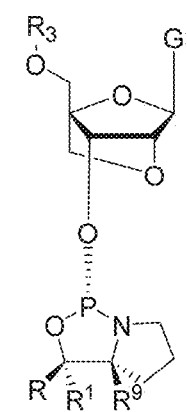
Formula 48

MULTIPLE COUPLING AND OXIDATION METHOD

CROSS REFERENCE TO RELATED APPLICATIONS

This application is a National Phase application under 35 U.S.C. § 371 of PCT International Application number PCT/EP2018/067015 filed Jun. 26, 2018, which claims priority to EP Patent Application No. 17178454.9 filed Jun. 28, 2017. The entire contents of the foregoing applications are hereby incorporated by reference.

FIELD OF THE INVENTION

The present invention relates to the field of stereodefined phosphorothioate oligonucleotides and to stereodefining nucleoside monomers and methods of synthesis of stereodefined oligonucleotides using said monomer. Herein are disclosed oligonucleotide enhanced synthesis methods where within a single elongation cycle there are repeated coupling and oxidation steps.

The method results in an enhanced yield and higher purity of stereodefined phosphorothioate oligonucleotides.

BACKGROUND TO THE INVENTION

Recently it has become apparent that the use of stereodefined phosphorothioate internucleoside linkages in oligonucleotides allow for the optimisation of the pharmacological profile of therapeutic oligonucleotides. However, the manufacture of stereodefined phosphorothioate oligonucleotides is at present comparatively inefficient as compared to non stereodefined phosphorothioate oligonucleotides. There is therefore a need to improve the efficiency of synthesis of stereodefined oligonucleotides.

Wan et al., Nucleic Acids Research (Advance Access published Nov. 14, 2014) disclose the synthesis of (S)cET gapmer antisense oligonucleotides containing chiral phosphorothioate linkages within the DNA gap region. The oligonucleotides made by Wan et al. incorporated oxazaphospholidine DNA monomers into (S)cET gapmers. The DNA amidites were prepared as 0.2M concentration in acetonitrile/toluene (1:1 v/v), and were coupled using a double coupling step. The (S)cET monomers were standard (not stereodefining) amidites.

WO2014/010250 discloses nucleoside monomers which when incorporated into an oligonucleotide provide a chirally defined stereocenter at the corresponding phosphorothioate internucleoside linkage position. The coupling step reported in WO2014/010250 is performed in acetonitrile.

WO98016540 discloses improved coupling activators for oligonucleotide synthesis. The oligonucleotide synthesis methods include the use of a double coupling prior to oxidation.

Ravikumar et al., Organic Process Research & Development 2008, 12, 399-410, disclose a Unylinker oligonucleotide support.

PCT/EP2017/060985 provides enhanced solvent compositions for enhancing the solubility, stability and reactivity of oxazaphospholidine phosphoramidite monomers.

EP17163506.3 provides oxazaphospholidine phosphoramidite monomers comprising orthogonally protected amine groups on the oxazaphospholidine chiral auxiliary.

The present invention is based upon the finding that multiple coupling/oxidation cycles within a single elongation synthesis cycle results in an enhanced yield when the monomer coupled during the elongation cycle is an oxazaphospholidine phosphoramidite monomer. The increase in yield is considered to be due to the stabilisation of the intermediate phosphite-triester by sulfurization, which appears to be unstable in the prolonged coupling steps required to achieve efficient coupling.

STATEMENT OF INVENTION

The invention provides for an improved synthesis method for stereodefined phosphorothioate oligonucleotides. The improved methods result in an enhanced coupling efficacy of oxazaphospholidine phosphoramidite monomers within a single elongation step as compared to the coupling efficacy which can be achieved by using a single coupling and single oxidation step within the single elongation step. The improved methods result in an enhanced oligonucleotide yield as compared to stereodefined phosphorothioate oligonucleotide synthesis methods which use a single coupling and single oxidation step within the single elongation step.

The invention provides for a method for the synthesis of a stereodefined phosphorothioate oligonucleotide, comprising the step of:
a) deprotecting a protected 5'-hydroxy terminus of a nucleoside, or oligonucleotide, attached to a solid support (e.g. unilinker),
b) coupling an oxazaphospholidine phosphoramidite monomer to the deprotected 5'-hydroxy terminus of a nucleoside or oligonucleotide, to form a phosphite triester intermediate,
c) oxidizing the phosphite triester intermediate with a sulfurizing reagent, followed by an optional washing step,
d) repeating steps b) and c) within the same elongation cycle (i.e. without repeating step a)),
e) optionally repeating steps a)-d) for one or more further elongation cycles,
f) deprotecting and cleavaging the oligonucleotide from the solid support.

Suitably, in some embodiments after step d), and prior to step e) a capping step may be performed.

In some embodiments the coupling step b) comprises coupling an oxazaphospholidine phosphoramidite monomer to a 5'-terminus of a nucleoside or oligonucleotide, comprising the step of reacting the nucleoside or oligonucleotide, with an oxazaphospholidine phosphoramidite monomer, wherein said reaction takes place in an acetonitrile solvent composition comprising acetonitrile and an aromatic heterocyclic solvent.

The method of the invention may comprise multiple further elongation cycles e), such as 2, 3, 4, 5, 6, 7, 8, 9, 10, 11, 12, 13, 14, 15, 16, 17, 18, 19, 20 or more further elongation cycles.

As is illustrated in PCT/EP2017/060985, the use of solvent composition of the invention (also referred to as the acetonitrile and aromatic heterocyclic solvent composition), enhances the solubility and stability of oxazaphospholidine phosphoramidite monomers and this may result in an enhanced utility in oligonucleotide synthesis. In some embodiments the oxazaphospholidine phosphoramidite monomers are soluble in the solvent composition for a period of at least 24 hours. The invention further provides for a solution of an oxazaphospholidine phosphoramidite monomer comprising the monomer and an acetonitrile solvent composition of the invention (acetonitrile and an aromatic heterocyclic solvent composition), for use in the method of the invention. In some embodiments, the solution of oxazaphospholidine phosphoramidite monomer is stable for at least 24 hours.

FIGURES

FIG. 1: Stability of various L and D nucleoside monomers in a selection of solvents. 3=Comparatively unstable, 2=intermediate stability, 1=Comparatively stable.

FIG. 2: Solubility of various L and D nucleoside monomers in a selection of solvents FIG. 3: Stability of L-LNA-G-iBu monomer (3a) and L-LNA-G-DMF monomer as measured after 24 hours in various solvents (see example 6).

Figure 4:
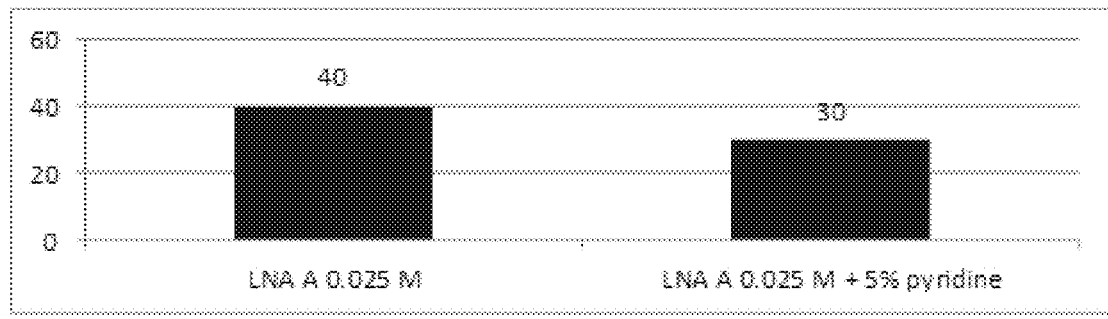

FIG. 4: Addition of 5% pyridine to the acetonitrile solvent decreases the coupling efficacy of conventional phosphoramidites.

Figure 5:
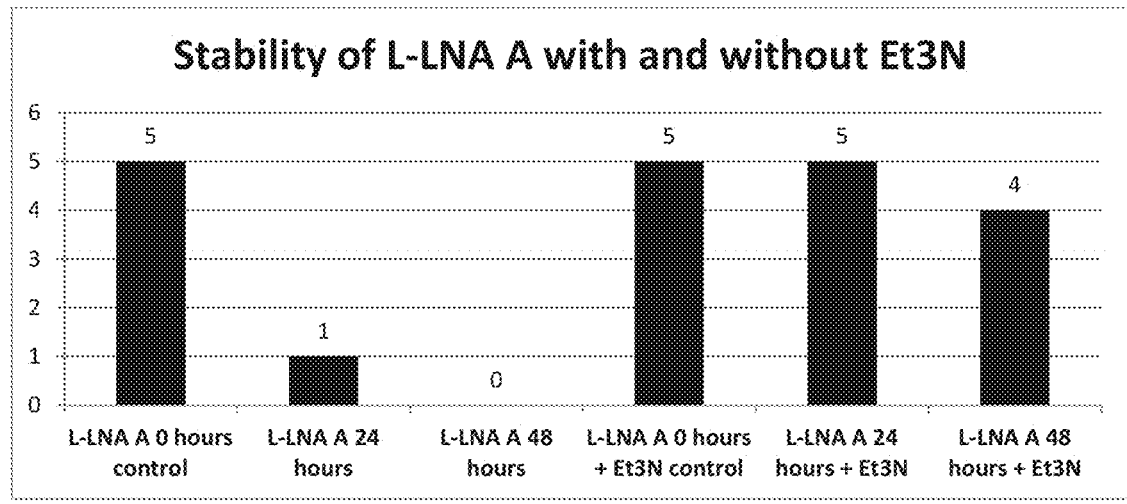

FIG. 5: Stability of L-LNA-A with and without triethylamine. Triethylamine stabilises L-LNA A monomers.

Figure 6:
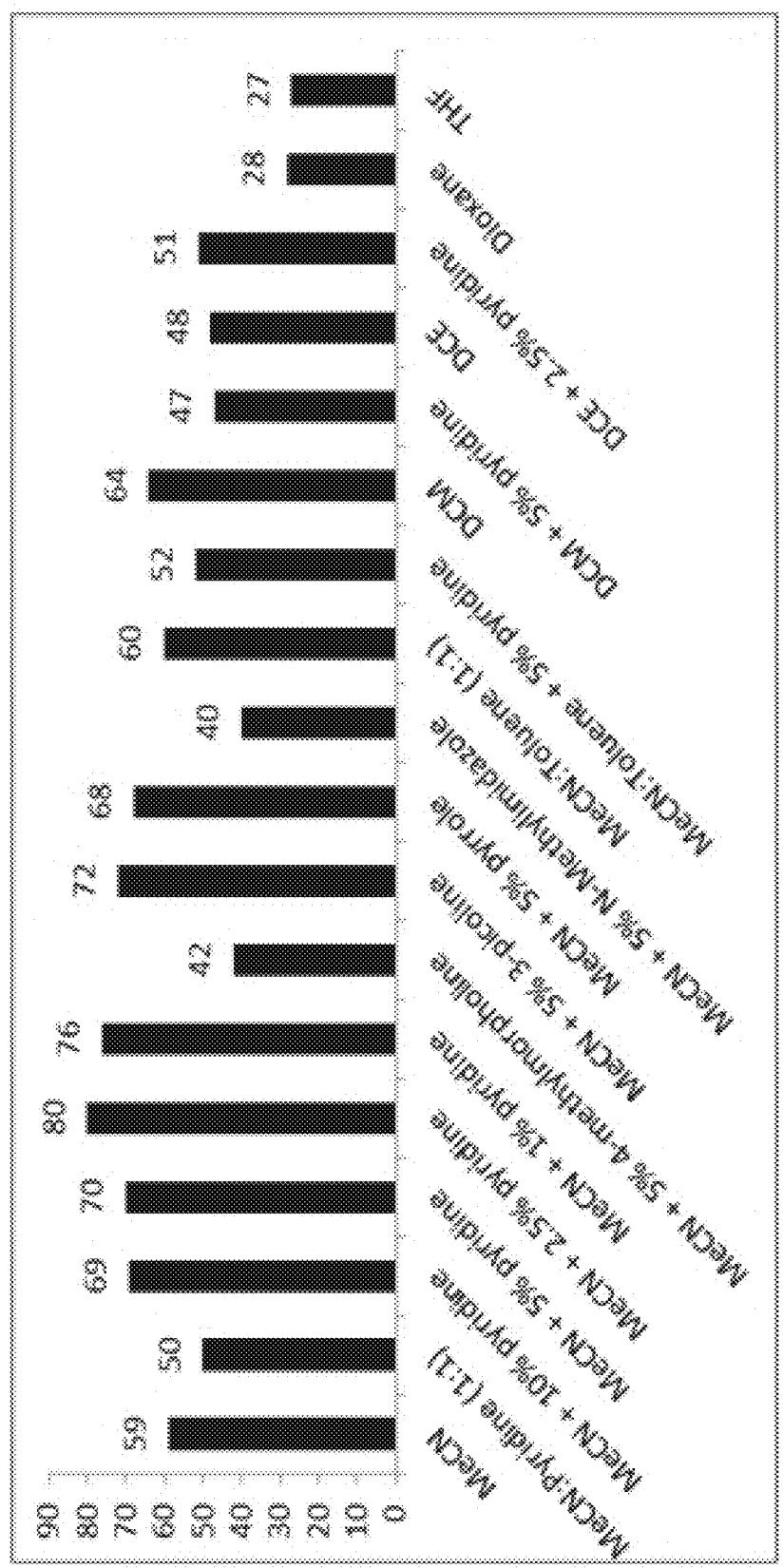

FIG. 6: Relative coupling efficiency in the model system using stereodefined L-LNA—A oxazaphospholidine phosphoramidite monomers and a variety of different amine bases.

Figure 7:
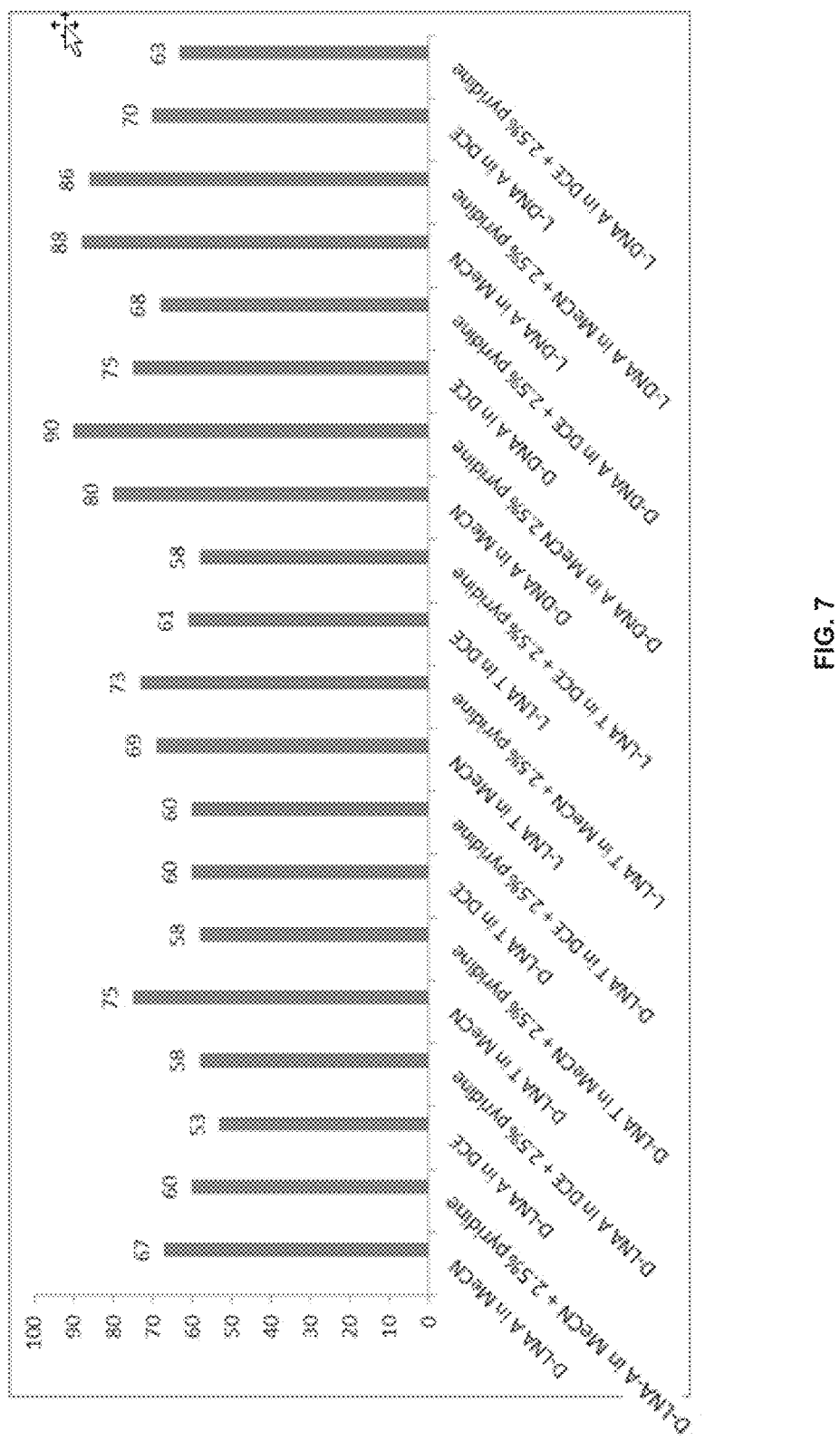

FIG. 7: Relative coupling efficiency in the model system using various oxazaphospholidine phosphoramidite monomers in a variety of solvents. Further testing additional monomers reveals that the solubility enhancing effect of the addition of pyridine is general across the series of monomers. As in the case of D-LNA A, D-DNA A and, L-DNA A these monomers are not soluble after 24 hours in MeCN. However with the addition of pyridine the solubility of the monomer is preserved. The enhancement in reactivity is also seen for D-DNA A and L-LNA T while L-DNA A and D-LNA A reacts in a comparable manner.

Figure 8:
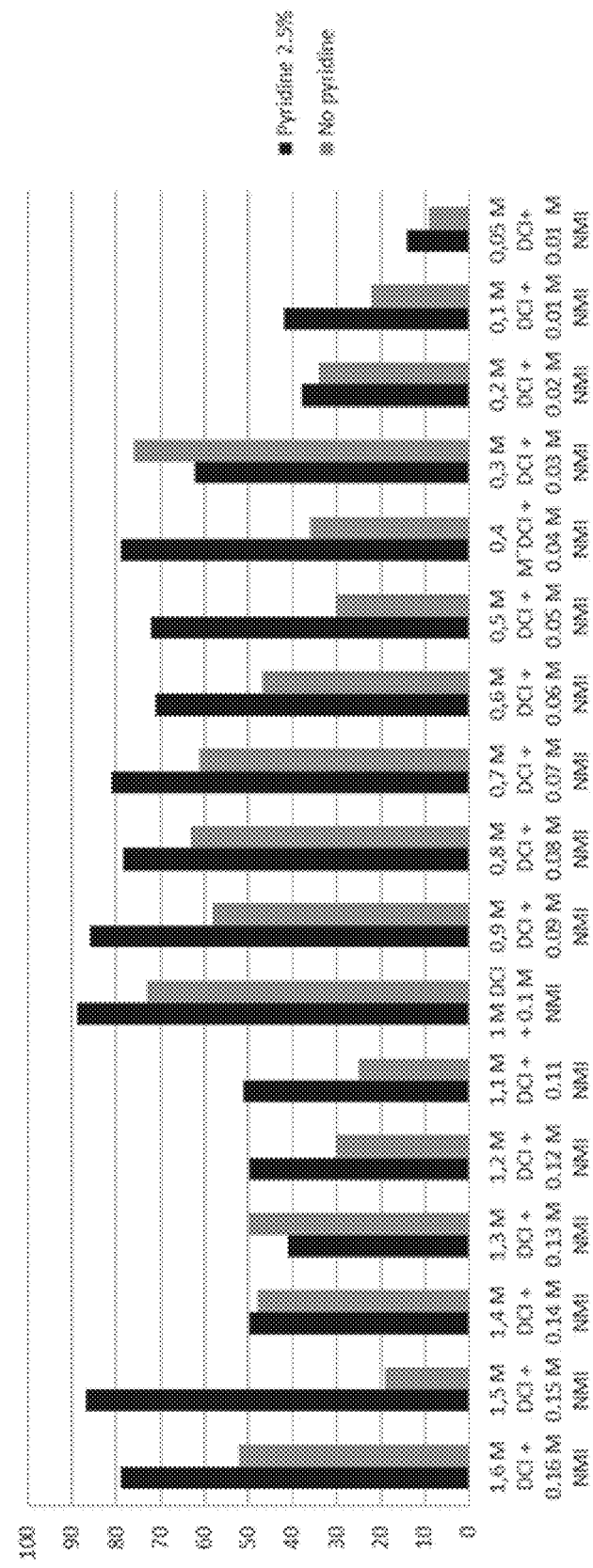

FIG. 8: Conversion of full length product with and without 2.5% pyridine.

Figure 9:
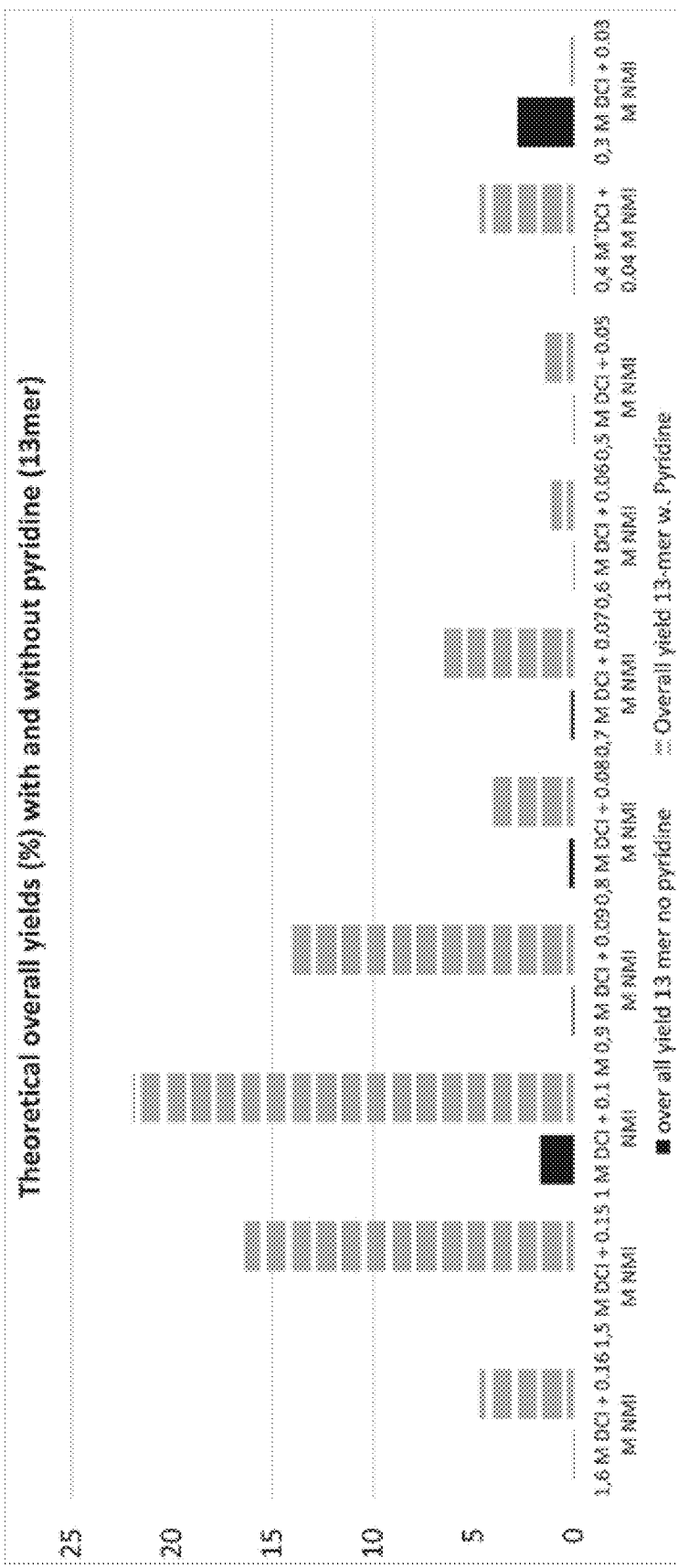

FIG. 9: Theoretical yields (%) with and without pyridine—a 13mer.

Figure 10:
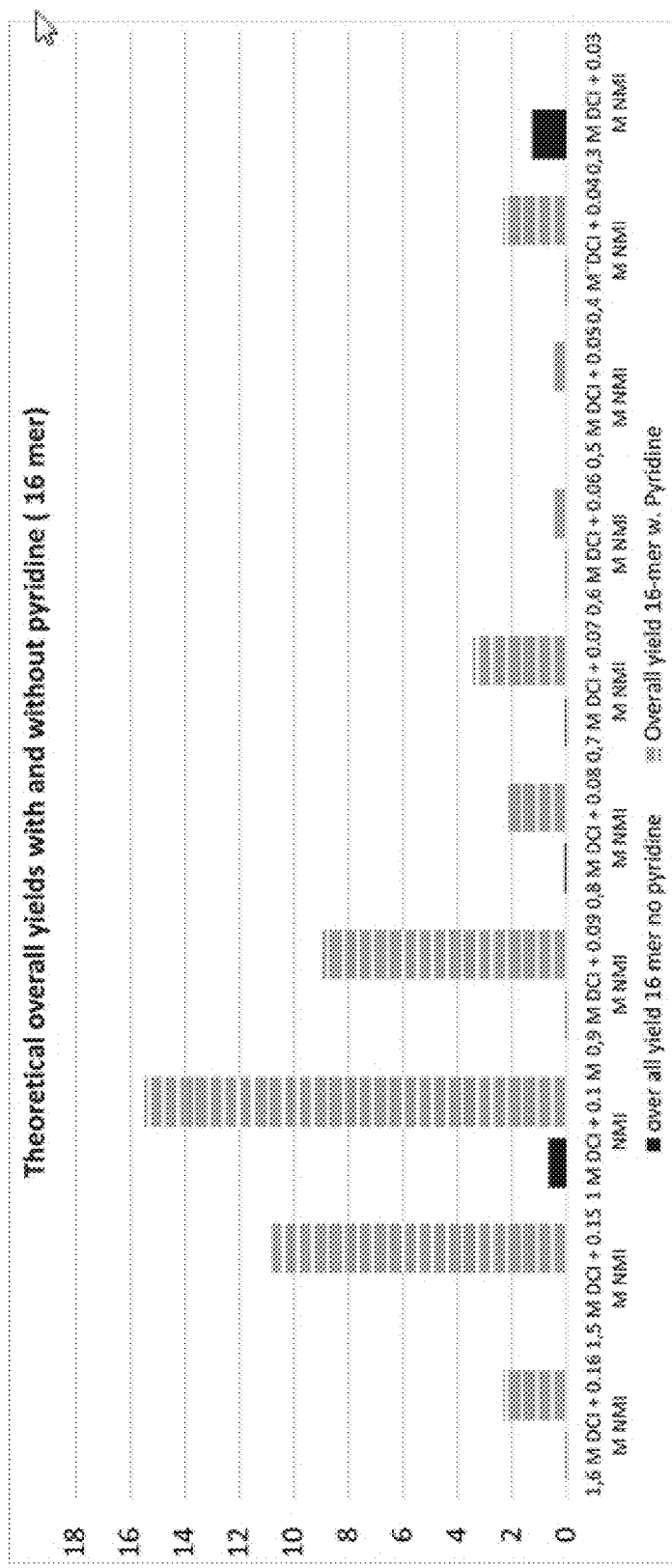

FIG. 10: Theoretical yields (%) with and without pyridine—a 16mer.

Figure 11:
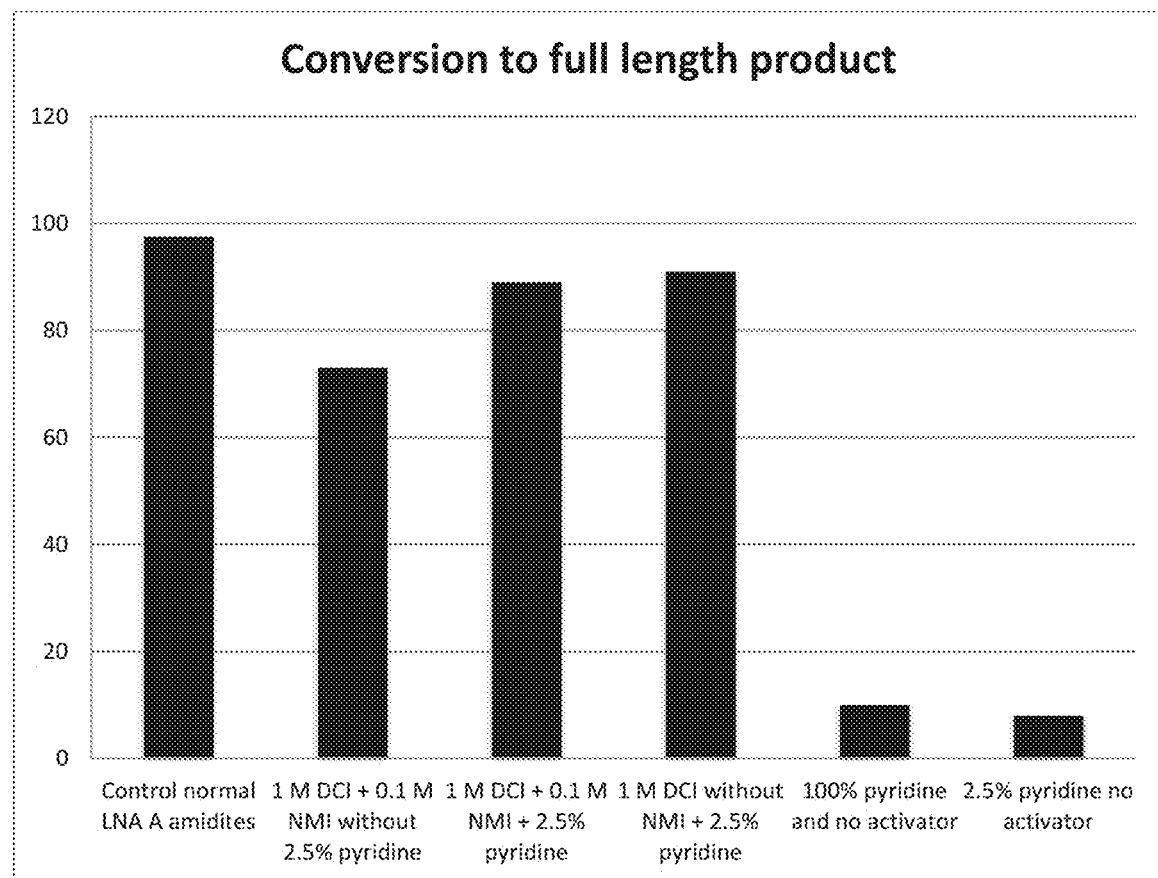

FIG. 11: Conversion to full length product in the presence of no pyridine, 100% pyridine solvent, and 2.5% pyridine, illustrating that 2.5% pyridine results in a conversion rate which is approaching that achieved with non-stereodefined phosphoamidate coupling.

Figure 12:
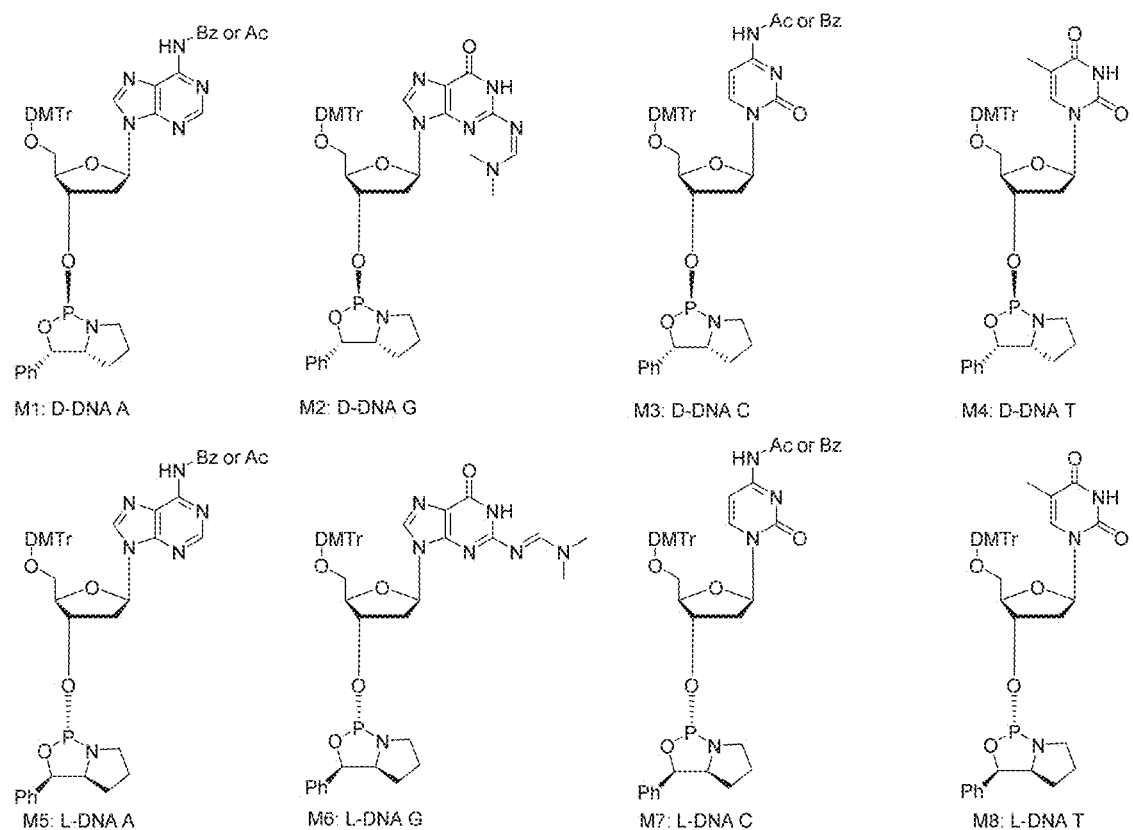

FIG. 12: Exemplary oxazaphospholidine phosphoramidite DNA monomers M1-M8. Ac=acetyl protection group, Bz=benzoyl protection group.

Figure 13:
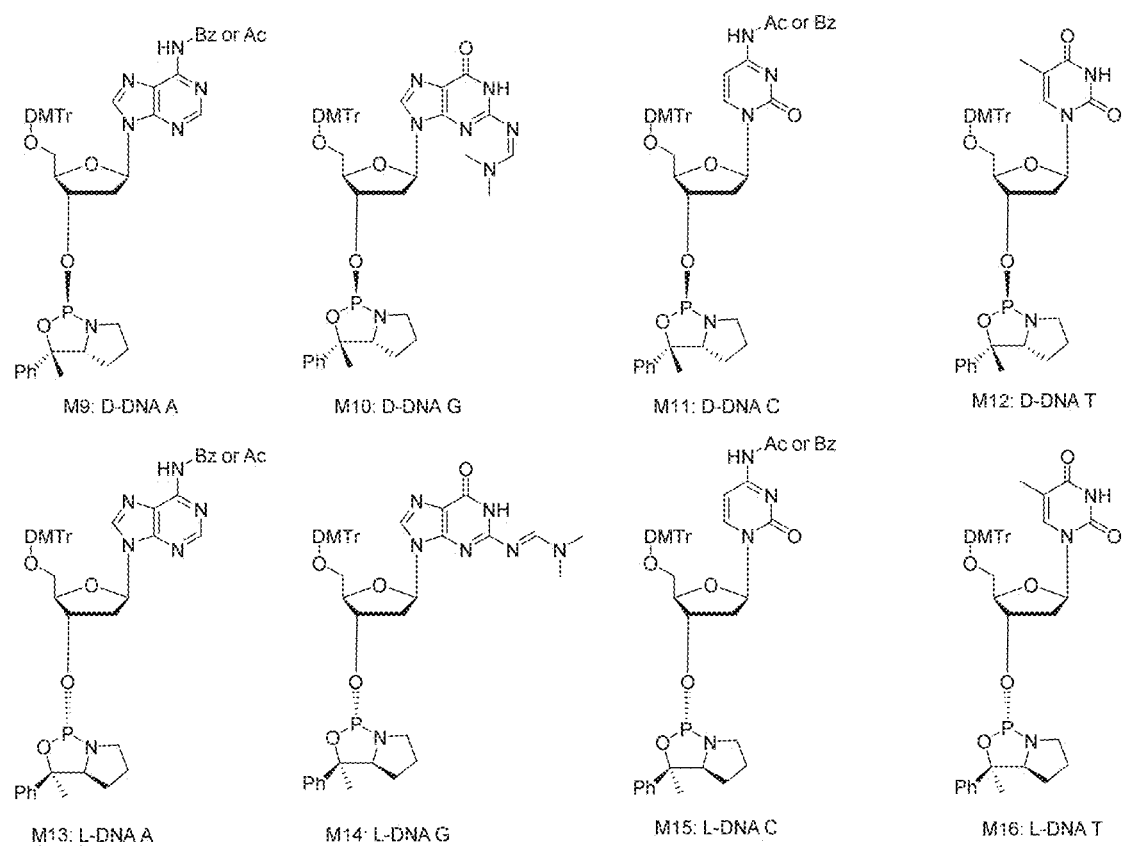

FIG. 13: Exemplary oxazaphospholidine phosphoramidite DNA monomers M9-M16, wherein $R^1$=methyl; Ac=acetyl protection group, Bz=benzoyl protection group.

FIG. 14: Exemplary oxazaphospholidine phosphoramidite LNA monomers M17-M24. Ac=acetyl protection group, Bz=benzoyl protection group.

Figure 15:
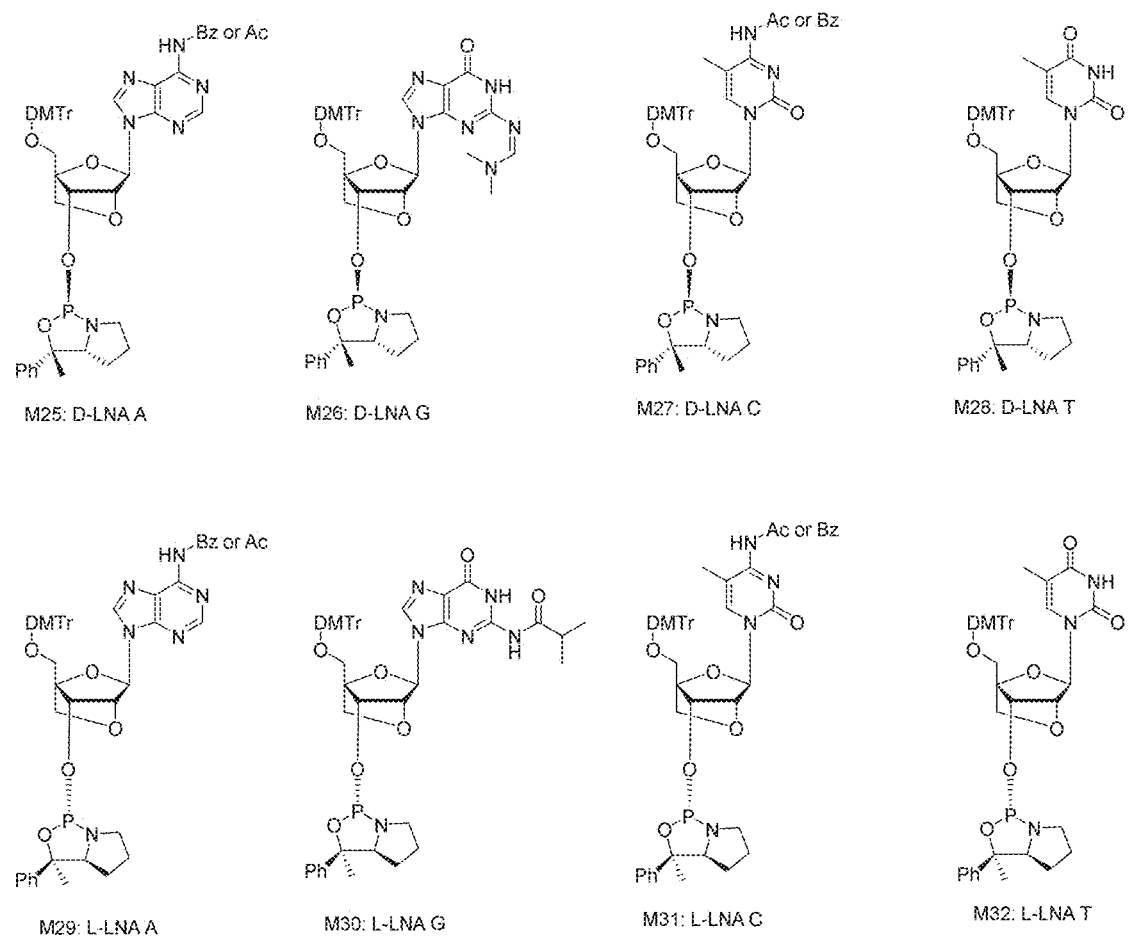

FIG. 15: Exemplary oxazaphospholidine phosphoramidite LNA monomers M25-M32; wherein $R^1$=methyl; Ac=acetyl protection group, Bz=benzoyl protection group.

Figure 16:
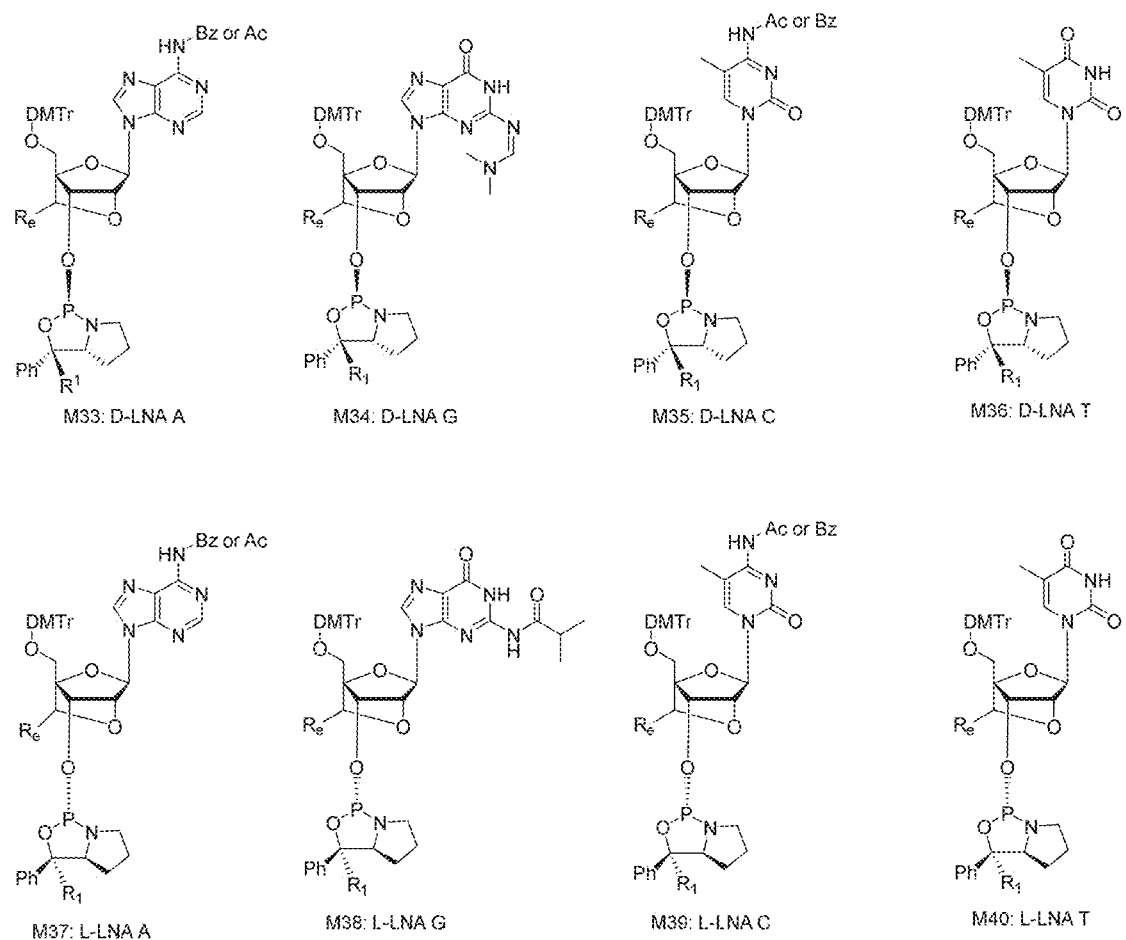

FIG. 16: Exemplary oxazaphospholidine phosphoramidite LNA monomers M32-M40, wherein $R^1$=is selected from hydrogen and methyl; $R_e$ is methyl which may be in either the S or R configuration, preferably in the S configuration ((S)Cet), Ac=acetyl protection group, Bz=benzoyl protection group.

FIG. 17: Exemplary oxazaphospholidine phosphoramidite DNA monomers (Formulas 33-40). A=adenine, which may optionally be protected, e.g. with acetyl or benzoyl; T=thymine; C=cytosine which may optionally be 5-methyl cytosine, cytosine or 5-methyl cytosine may optionally be protected e.g. with benzoyl or acetyl; G=guanine which may optionally protected e.g. with acyl, such as iBu or DMF; $R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$, preferably —$CH_2$—O-DMTr; R is aryl, preferably phenyl; $R^1$ is hydrogen or methyl; $R^9$ is hydrogen.

FIG. 18: Exemplary oxazaphospholidine phosphoramidite LNA monomers (Formulas 41-48). A=adenine, which may optionally be protected, e.g. with acetyl or benzoyl; T=thymine; C=cytosine which may optionally be 5-methyl cytosine, cytosine or 5-methyl cytosine may optionally be protected e.g. with benzoyl or acetyl; G=guanine which may optionally protected e.g. with acyl, such as iBu for L-LNA-G monomers or either acyl (such as iBu) or DMF for D-LNA-G monomer; $R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$, preferably —$CH_2$—O-DMTr; R is aryl, preferably phenyl; $R^1$ is hydrogen or methyl; $R^9$ is hydrogen.

Figure 19:
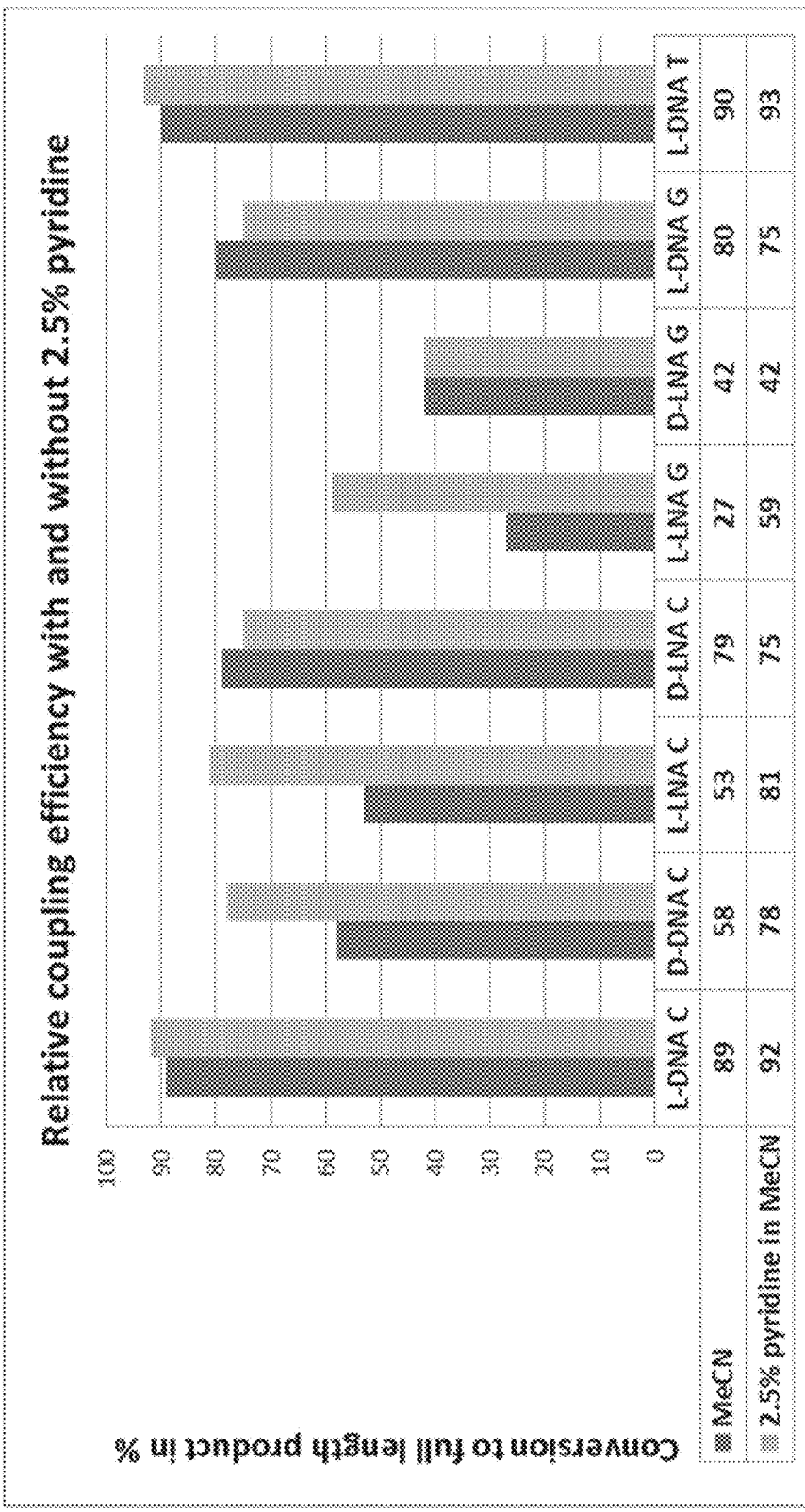

FIG. 19: Relative coupling efficiency in the model system using various oxazaphospholidine phosphoramidite monomers in acetonitrile with or without 2.5% pyridine. The figure illustrates that the coupling efficacy of L-LNA-G, L-LNA-C, D-DNA-C are markedly improved by the presence of 2.5% pyridine in the coupling solvent, for the remaining monomers tested, the addition of pyridine either improve coupling efficacy (e.g. L-DNA-T or L-DNA-C) did not adversely effects the coupling efficacy, and considering the solubility and stability benefits of pyridine on the monomers, the results illustrate the benefit of using coupling solvents comprising heterocyclic base solvents, such as pyridine, are seen for all the monomers.

Figure 20:
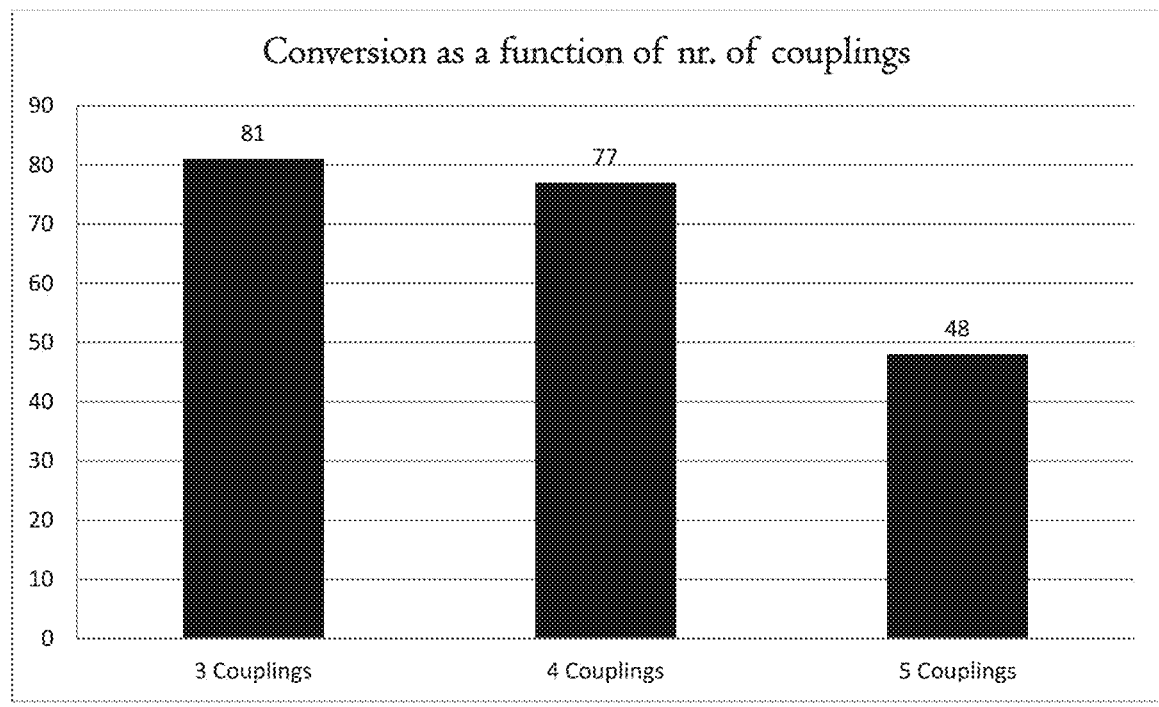

FIG. 20: The observation that multiple couplings (e.g. CCCOW, CCCCOW or CCCCCOW), results in a reduction in oligonucleotide yield.

Figure 21:
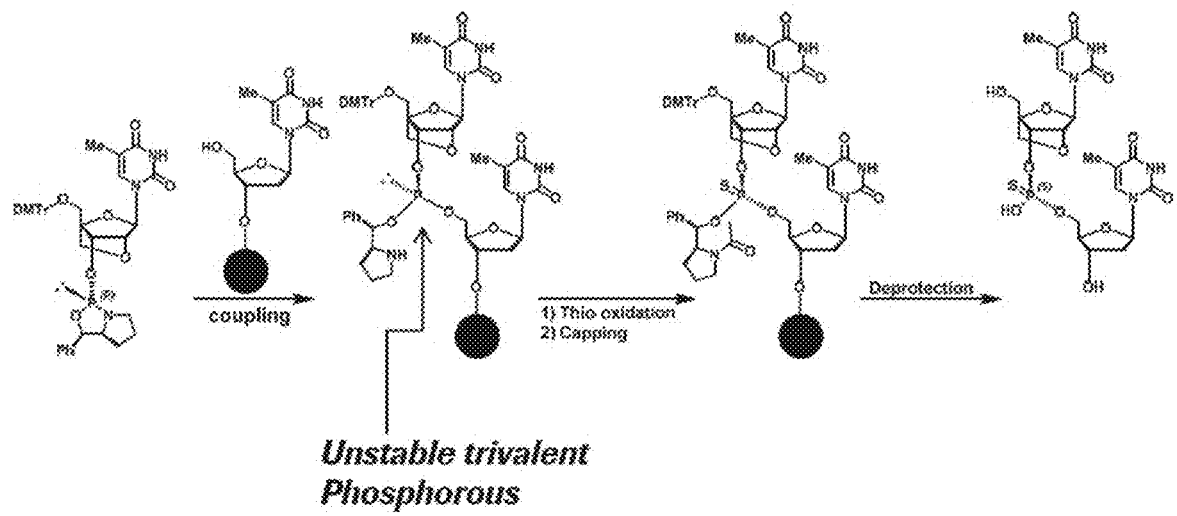

FIG. 21: A Proposed mechanism for the instability of the coupled intermediate prior to oxidation.

Figure 22:
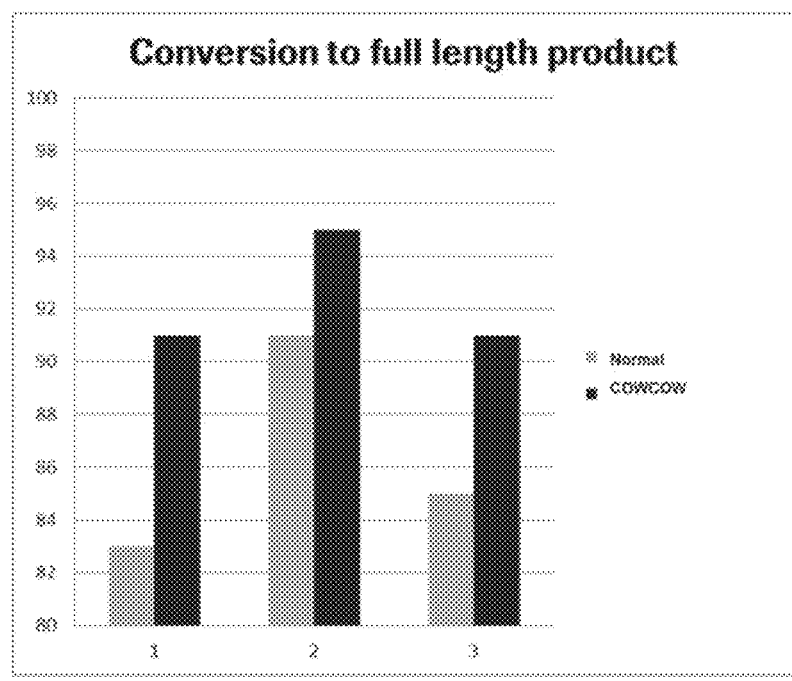

FIG. 22: 1, 2, and 3 denotes three separate positions in the oligonucleotide synthesis machine. In order to avoid position to position variation between the results each positions is only compared to itself. In it seen that in all cases the COWCOW cycle improves the relative coupling efficiency as compared to the "Normal" cycle.

Figure 23:
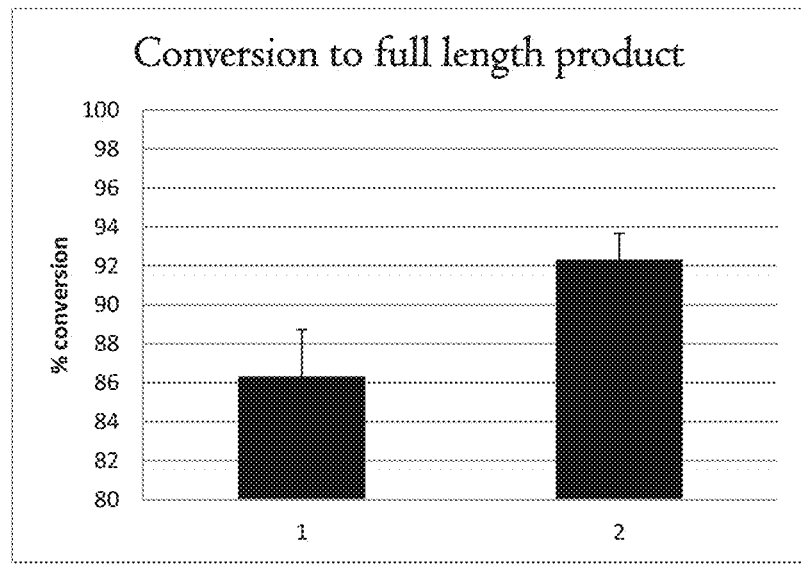

FIG. 23: The results from FIG. 22 have here been summarized and statically evaluated using std. error. Here it is seen that the COWCOW cycle is significantly better than the "normal" cycle thus underlying the importance of the COW-COW coupling cycle. Column 1: Using the conventional coupling cycle of: coupling ×3, oxidation, capping, and DMTr deprotection. Column 2: Using the modified coupling cycle now known as COWCOW, consisting of: Coupling, oxidation, wash, coupling, oxidation wash, coupling, oxidation wash (COWCOWCOW), DMTr deprotection. 1: Normal coupling 2: Enhanced coupling cycle of the invention.

Figure 24:
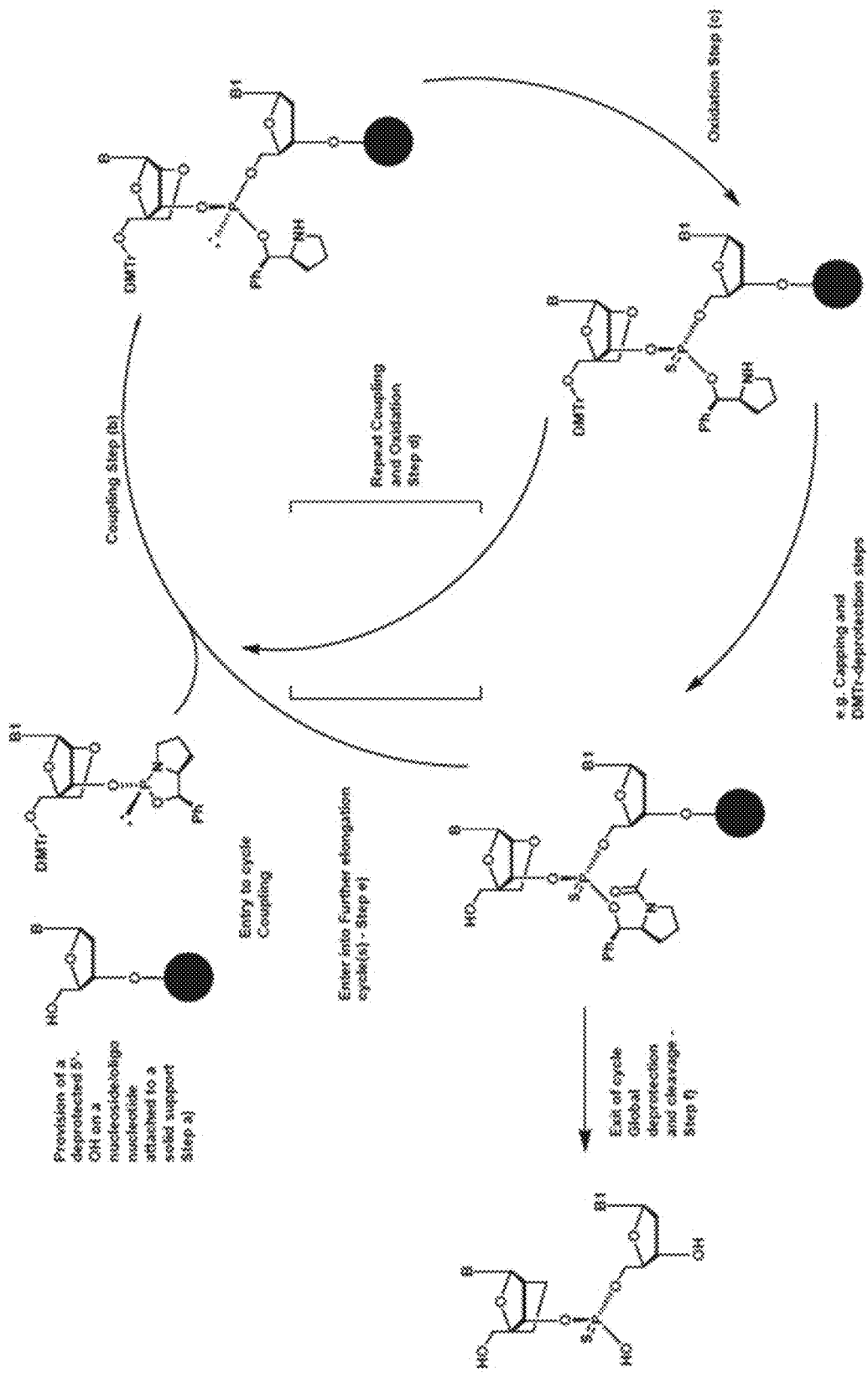

FIG. 24: An example of the repeated coupling and oxidation oligonucleotide synthesis method of the invention.

Figure 25:
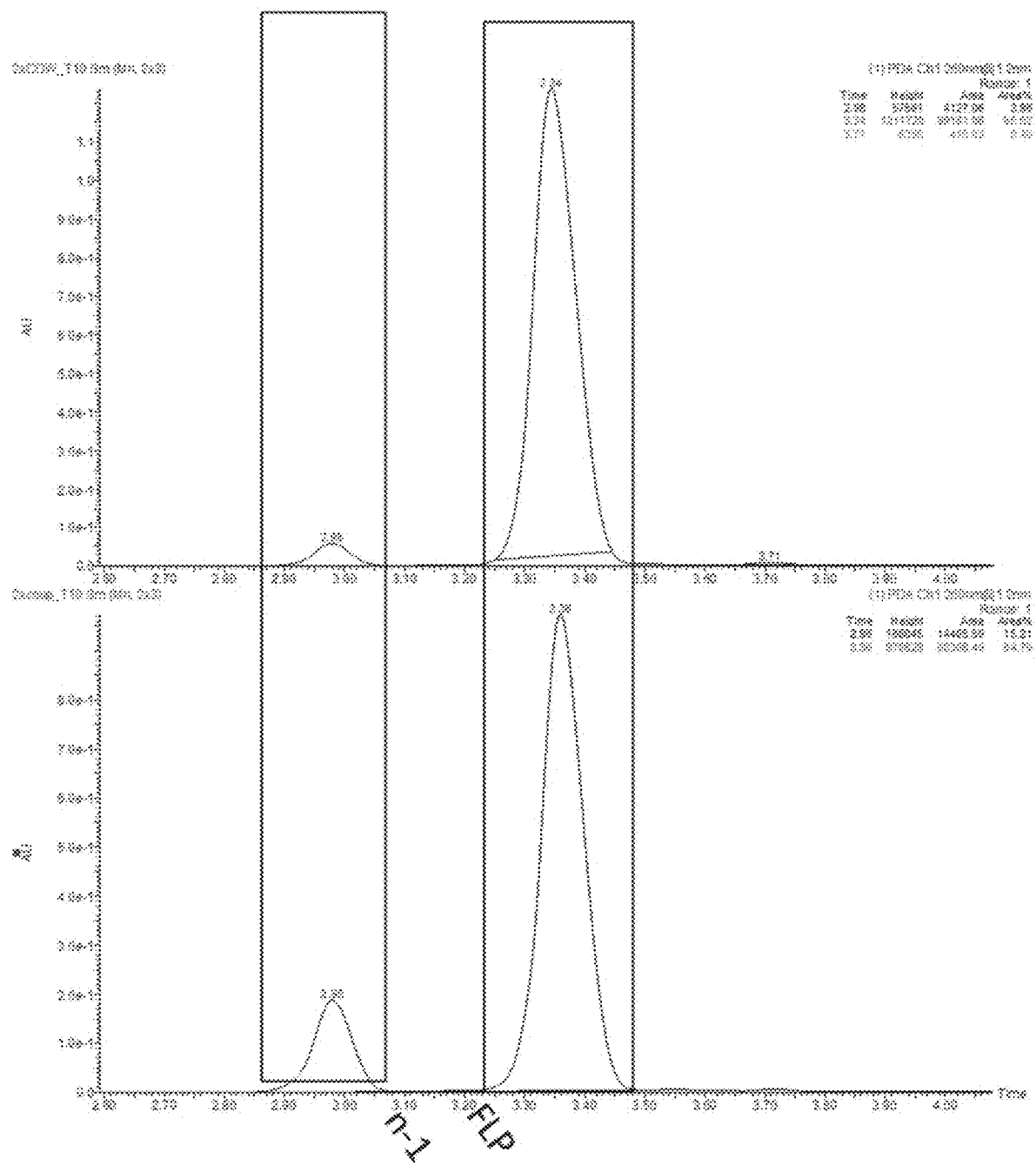

FIG. 25: Chromatograms showing the coupling efficiency of a L-DNA T monomer on a (dT)9 oligonucleotide as outlined in example 20.

Figure 26:
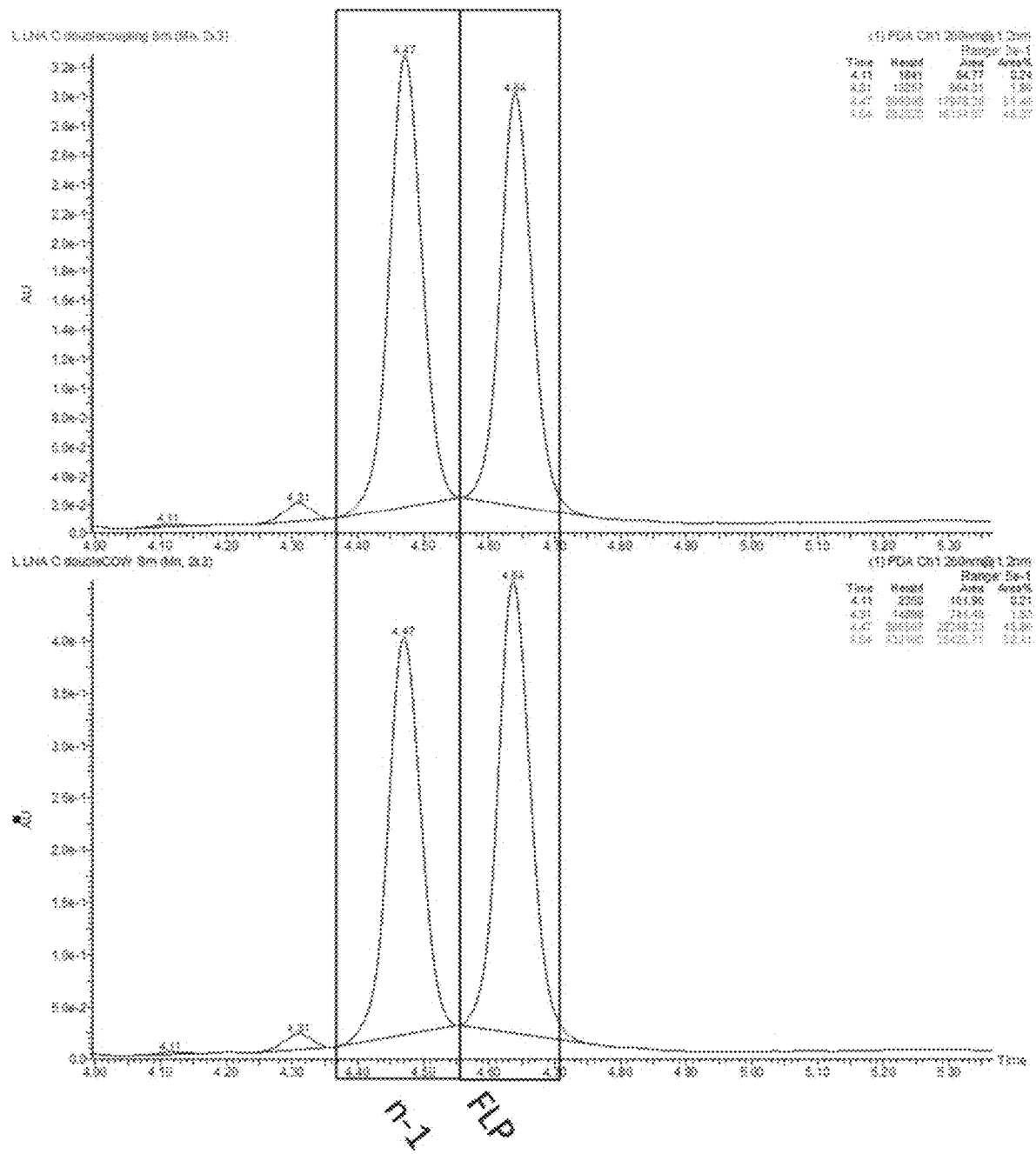

FIG. 26: Chromatograms showing the coupling efficiency of a L-LNA C monomer on a (dT)15 oligonucleotide as outlined in example 20.

DETAILED DESCRIPTION

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_{1-10}$ aryl. In some embodiments aryl is phenyl. When substituted aryl may be substituted with a group selected from the group consisting of: $C_{1-4}$ alkyl group, $C_{6-14}$ aryl group $C_{1-4}$, alkoxy group, $C_{7-14}$ aralkyl group, $C_1$. 4 alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$alkoxy, $C_{6-14}$ aryl group, or $C_{6-14}$ aryl $C_{6-14}$ alkyl group; or a group selected from the group consisting of halide, such as iodide, fluoride, bromide or chloride, such as phenyl substituted with halide, such as iodide, fluoride, bromide or chloride.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring. The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_{1-6}$ alkyl" or similar designations. By way of example only, "$C_{1-6}$ alkyl" indicates that there are one, two, three, four, five, or six carbon atoms in the alkyl chain, i.e., the alkyl chain is selected from the group consisting of methyl, ethyl, propyl, iso-propyl, n-butyl, isobutyl, sec-butyl, and tert-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_{1-4}$ or $C_{1-4}$alkyl or $C_{1-3}$ alkyl. $C_{1-3}$ alkyl group means straight or branched alkyl group that has 1 to 3 carbon atoms. Examples of $C_{1-4}$ alkyl group are methyl, ethyl, propyl and isopropyl. $C_{1-3}$ alkyl group means straight or branched alkyl group that has 1 to 4 carbon atoms. Examples of $C_{1-3}$ alkyl groups are methyl, ethyl, propyl, isopropyl, butyl, isobutyl, and tert-butyl.

"Alkenyl" groups are straight chain, branch chain, and cyclic hydrocarbon groups containing at least one carbon-carbon double bond. Alkenyl groups can be substituted.

"Alkynyl" groups are straight chain, branch chain, and cyclic hydrocarbon groups containing at least one carbon-carbon triple bond. Alkynyl groups can be substituted.

An "alkoxy" group refers to an alkyl group linked to oxygen i.e. (alkyl)-O— group, where alkyl is as defined herein. Examples include methoxy (—$OCH_3$) or ethoxy (—$OCH_2CH_3$) groups.

An "alkenyloxy" group refers to an alkenyl group linked to oxygen i.e. (alkenyl)-O— group, where alkenyl is as defined herein.

An "alkynyloxy" group refers to an alkynyl group linked to oxygen i.e. (alkynyl)-O— group, where alkynyl is as defined herein.

An "aryloxy" group refers to an aryl group linked to oxygen i.e. (aryl)-O— group, where the aryl is as defined herein. An example includes phenoxy (—$OC_6H_5$) group.

"Silyl" refers to $H_3Si$—. "Substituted silyl" as used herein, refers to a moiety which has one or more the hydrogen of silyl substituted. Examples include, but are not limited to, TBDMS {tert-butyldimethylsilyl}, TBDPS (tert-butyldiphenylsilyl) or TMS {trimethylsilyl} group.

The term "halogen" is intended to include fluorine, chlorine, bromine and iodine. The term "halide" includes fluoride, bromide, iodide and chloride.

An "acyl protection group" comprises an acyl group —C(═O)—$R^7$, wherein $R^7$ is a terminal group, for example a group selected from, alkyl-, alkyl-, alkenyl-, alkynyl-, cycloalkyl- and aryl-group; or a group selected from, unsubstituted alkyl-, unsubstituted alkenyl-, unsubstituted alkynyl-, unsubstituted cycloalkyl- or unsubstituted aryl-group; or a group selected from substituted alkyl-, substituted alkenyl-, substituted alkynyl-, substituted cycloalkyl- or substituted aryl-group. In some embodiments $R^7$ may be selected from the group consisting of unsubstituted $C_{1-6}$-alkyl-, unsubstituted $C_{2-6}$-alkenyl-, unsubstituted $C_{2-6}$-alkinyl-, unsubstituted $C_{3-7}$-cycloalkyl- or unsubstituted phenyl-group or substituted $C_{1-6}$-alkyl-, substituted $C_{2-6}$-alkenyl-, substituted $C_{2-6}$-alkinyl-, substituted $C_{3-7}$-cycloalkyl- or substituted phenyl-group; wherein when substituted, the substituent group may be mono or poly substituted, e.g. with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl. In some embodiments the acyl protection group is isobutyryl (—C(O═)CH(CH$_3$)$_2$) (also referred to herein as iBu). The term isobutyryl may also be spelt isobutyryl.

Oxazaphospholidine Phosphoramidite

The method of the invention comprises the step of coupling an oxazaphospholidine phosphoramidite to a nucleoside or nucleotide. The oxazaphospholidine phosphoramidite (also referred to as the nucleoside monomer) in some embodiments, is of formula 1:

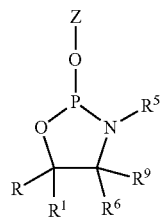

Formula 1 wherein Z is a nucleoside,
$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula 1;
$R^9$ is hydrogen;
$R^1$ is selected from the groups consisting of hydrogen and $C_{1-3}$ alkyl; and,
R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;
wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

The R and $R^1$ ($R/R^1$) groups of the nucleoside of formula 1 provide a stereocenter which results in the formation of a Sp stereodefined phosphorothioate group 3' to the nucleoside when incorporated into an oligonucleotide.

In some embodiments, the stereocenter is in the L position, as illustrated in formula 1a. In some embodiments, the stereocenter is in the D position, as illustrated in formula 1b.

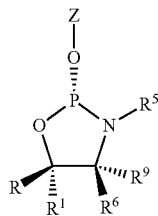

Formula 1a

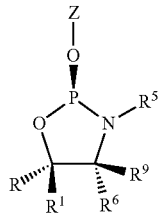

Formula 1b

The monomer comprising the stereocenter created by the R and $R^1$ groups as shown in formula 1a is referred to as an L monomer herein which results in the formation of a Sp stereocenter. The monomer comprising the stereocenter created by the R and R' groups as shown in formula 1b is referred to as a D monomer herein which results in the formation of a Rp stereocenter.

When substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

In some embodiments R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

In some embodiments R is selected from the group consisting of aryl, heteroaryl, substituted aryl and substituted heteroaryl.

In some embodiments R is aryl, such as phenyl.

In some embodiments, when R is substituted aryl, R may be substituted with halide, such as iodide, fluoride, bromide or chloride, such as phenyl substituted with halide, such as iodide, fluoride, bromide or chloride.

In some embodiments $R^1$ is hydrogen. In some embodiments $R^1$ is $C_{1-3}$alkyl, such as methyl, ethyl or propyl. In some embodiments $R^1$ is methyl.

In some embodiments, R is aryl, such as phenyl and $R^1$ is hydrogen.

In some embodiments, R is aryl, such as phenyl, and $R^1$ is $C_{1-3}$alkyl, such as methyl, ethyl or propyl.

In some embodiments R is

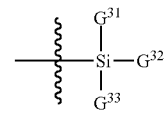

wherein $G^{31}$, $G^{32}$ and $G^{33}$ are independently selected from the groups consisting of $C_{1-4}$ alkyl, $C_{6-14}$ aryl$C_{1-4}$ alkoxy, $C_{7-14}$ aralkyl, $C_{1-4}$ alkyl$C_{6-14}$ aryl, $C_{1-4}$ alkoxy$C_{6-14}$ aryl, and $C_{6-14}$ aryl$C_{1-4}$ alkyl.

In some embodiments R is

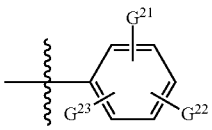

wherein $G^{21}$, $G^{22}$ and $G^{23}$ are independently hydrogen, nitro, halogen, cyano or $C_{1-3}$alkyl.

In some embodiments R is

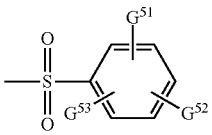

wherein $G^{51}$, $G^{52}$ and $G^{53}$ are independently hydrogen, nitro, halogen, cyano or $C_{1-3}$alkyl or $C_{1-3}$ alkyloxy group.

In some embodiments $R^5$ and $R^6$ together form a heterocylic ring (with the cyclic nitrogen shown in Formula 1)—nucleoside monomers referred to as bicyclic oxazaphospholidine phosphoramidites. The heterocyclic ring may comprise, for example 3-16 carbon atoms, such as 4 carbons atoms.

Orthogonally Protected Oxazaphospholidine Phosphoramidite Monomers

EP17163506.3, hereby incorporated by reference, provides oxazaphospholidine phosphoramidite monomers comprising orthogonally protected amine groups on the oxazaphospholidine chiral auxiliary. In some embodiments the oxazapholidine phosphoramidite monomer is an orthogonally protected oxazapholidine phosphoramidite monomer.

Bicyclic Oxazapholidine Phosphoramidite Monomers

In some embodiments the monomer is a bicyclic oxazapholidine phosphoramidite monomer, e.g. in some embodiments $R^5$ and $R^6$ together form a heterocylic ring. In some embodiments $R^5$ and $R^6$ together form a heterocylic ring (with the cyclic nitrogen shown in Formula 1) which comprises 4 carbon atoms, making a total of five atoms in the heterocyclic ring (4 carbon and the nitrogen shown in Formula 1). For example, the compound of the invention may be of formula 2a or 2b:

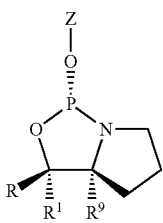

Formula 2a

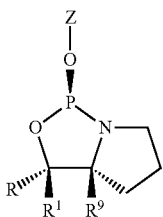

Formula 2b

Wherein R, $R^1$, $R^9$ and Z are as according to formula 1.

In some embodiments $R^5$ and $R^6$ together form a heterocylic ring (with the cyclic nitrogen shown in Formula I) which comprises 4 carbon atoms, making a total of five atoms in the heterocyclic ring (4 carbon and the nitrogen shown in Formula 1), and R is aryl, such as phenyl, $R^1$ is hydrogen or methyl. $R^9$ is hydrogen.

The Z group above is a nucleoside where the 3' oxygen of the nucleoside is the exocyclic oxygen shown in formula 1, 1a, 1b, 2a or 2b. In some embodiments the Z group is a LNA nucleoside moiety. In some embodiments the Z group is a DNA nucleoside moiety. In some embodiment the compound of the invention may therefore be represented as the compound of formula 3a or 3b:

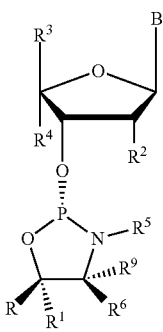

Formula 3a

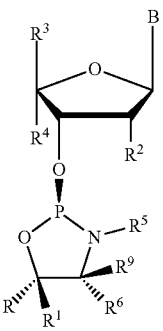

Formula 3b wherein, R, $R^1$, $R^5$, $R^6$ and $R^9$ are as per the compound of the invention;

B is a nucleobase,

In some embodiments B is a nucleobase selected from the group consisting of 9-adeninyl, 9-guaninyl, 1-cytosinyl, 1-thymidinyl, 1-uracil, 9-xanthinyl, 9-hypoxanthinyl, 1-5-methyl-cytosinyl, 1-isocytosinyl, 1-pseudoisocytosinyl, 1-5-bromo-uracil, 1-5-propynyl-uracil, 9-6-aminopurinyl, 9-2-aminopurinyl, 9-diaminopurinyl, and 9-2-chloro-6-aminopurinyl.

In some embodiments B is a purine nucleobase. In some embodiments B is a pyrimidine nucleobase. In some embodiments, B is a B is 9-adeninyl. In some embodiments, B is 1-thymidinyl. In some embodiments, B is 9-guaninyl. In some embodiments, B is 1-cytosinyl. In some embodiments, B is 1-5-methyl-cytosinyl.

In some embodiments, B is other than 1-cytosinyl, for example, when the monomer is a D-DNA monomer, e.g. of formula 20 or 22. In some embodiments, e.g. when the monomer is a D-DNA-C, B is other than acetyl (Ac) protected cytosine.

It should be understood that for use in oligonucleotide synthesis the nucleobase group B may be protected in the amidite monomers (thymidine is often used without a protection group).

Suitable protection groups include dimethyformamide (DMF), dimethoxytrityl (DMT) or an acyl protection group, such as isobutyryl (iBu), or an acetyl protection group (Ac) or a benzoyl protection group (Bz).

In some embodiments, e.g. when the monomer is a L-LNA-G, B is other than DMF protected 9-guaninyl (G). $R^3$= is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$;

$R^2$ is selected from the groups consisting of halo, such as —F, amino, azido, —SH, —CN, —OCN, —$CF_3$, —$OCF_3$, —O($R'''$)-alkyl, —S($R'''$)-alkyl, —N($R'''$)-alkyl, —O($R'''$)-alkenyl, —S($R'''$)-alkenyl, —N($R'''$)— alkenyl; —O($R'''$)-alkynyl, —S($R'''$)-alkynyl or —N($R'''$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R'''$)($R''$) or O—$CH_2C$(=O)—N($R'''$)($R''$), —O—$(CH_2)_2OCH_3$, and —O—$CH_3$, where each $R'''$ and $R''$ are independently, H, an amino protecting group or substituted or unsubstituted $C_{1-10}$ alkyl;

$R^4$= is selected from the group consisting of alkyl, cyclo-alkyl, cyclo-heteroalkyl, O-alkyl, S-alkyl, NH-alkyl, and hydrogen; In some embodiments, $R^4$ is hydrogen. In some embodiments, $R^4$ is hydrogen, and $R^2$ is selected from the group consisting of —O—$CH_3$, and —O—$(CH_2)_2OCH_3$.

Or in some embodiments, $R^2$ and $R^4$ together designate a bivalent bridge, such as consisting of 1, 2, 3 groups/atoms selected from the group consisting of —C($R^a R^b$)—, —C($R^a$)=C($R^b$), —C($R^a$)=N, O, —Si($R^a$)$_2$—, S—, —SO$_2$—, —N($R^a$)—, and >C=Z;

wherein $R^a$ and, when present $R^b$, each is independently selected from hydrogen, optionally substituted $C_{1-6}$alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryl-oxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation.

In some embodiments, when incorporated into an oligonucleotide, the nucleoside (Z) confers a higher binding affinity to a complementary RNA target than an equivalent DNA nucleoside. Such nucleosides are referred to as high affinity nucleosides. Examples of high affinity nucleosides include 2'-O-MOE, 2'-fluoro, 2'-O-methyl, and LNA nucleosides. In the embodiments, where the nucleoside is a high affinity nucleoside $R^3$ may, for example, be CH$_2$—O-DMTr or CH$_2$—O-MMTr.

In some embodiments, $R^2$ is selected from the group consisting of fluoro (—F), —O—(CH$_2$)$_2$OCH$_3$, and —O—$C_{1-3}$ alkyl, such as —O—CH$_3$. In such embodiments, optionally $R^4$ is hydrogen.

In some embodiments, the nucleoside is a LNA nucleoside (also known as a bicyclic nucleoside) comprising a 2'-4' bridge (biradicle).

In some embodiments, $R^2$ and $R^4$ together designate a bivalent bridge selected from the group consisting of bridge —C($R^a R^b$)—O—, —C($R^a R^b$) C($R^a R^b$)—O—, —CH$_2$—O—, —CH$_2$ CH$_2$—O—, —CH(CH$_3$)—O—. In some embodiments, $R^2$ and $R^4$ designate the bivalent bridge —CH$_2$—O— (methylene-oxy also known as oxy-LNA) or —CH(CH$_3$)—O— (methyl-methylene-oxy). The —CH(CH$_3$)—O— bridge introduces a chiral center at the carbon atom within the bridge, in some embodiments this is in the S position (for example a nucleoside known in the art as (S)cET—see EP1984381)). In some embodiments. $R^2$ and $R^4$ designate the bivalent bridge —CH$_2$—O— wherein the bridge is in the beta-D position (beta-D-oxy LNA). In some embodiments, $R^2$ and $R^4$ designate the bivalent bridge —CH$_2$—O— wherein the bridge is in the alpha-L position (alpha-L-D-oxy LNA). In some embodiments, $R^2$ and $R^4$ designate the bivalent bridge —CH$_2$—S— (thio LNA), or —CH$_2$—NH$_2$— (amino LNA). In the embodiments where $R^2$ and $R^4$ together designate a bivalent bridge, $R^3$ may, for example be CH$_2$-O-DMTr or CH$_2$—O-MMTr.

In some embodiments where the nucleoside (Z) is a bicyclic nucleotides (LNA) such as beta-D-oxy LNA, R is aryl, such as phenyl, and $R^1$ is hydrogen or $C_{1-3}$ alkyl. In such am embodiment, $R^5$ and $R^6$ may together form a heterocylic ring, such as a five membered heterocyclic ring, as described herein (e.g. see formula 2a and 2b).

In some embodiments, the oxazaphospholidine phosphoramidite monomer is selected from the group consisting of formula 4a, 4b, 5a, 5b, 6a, 6b, 7a and 7b.

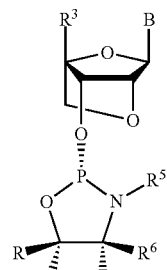

Formula 4a

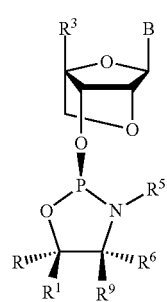

Formula 4b

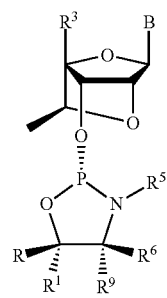

Formula 5a

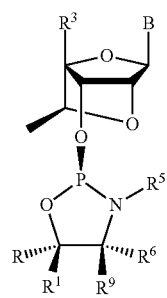

Formula 5b

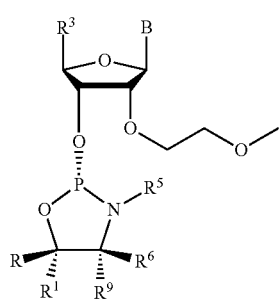

Formula 6a

Formula 6b
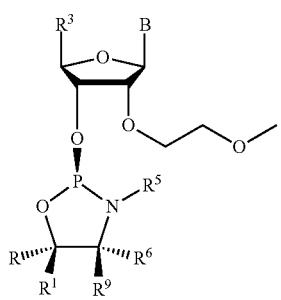
Formula 7a
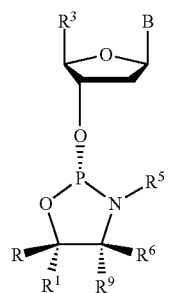
Formula 7b
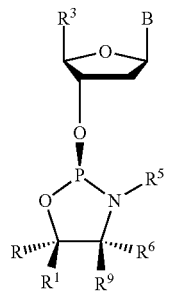
In some embodiments, the oxazaphospholidine phosphoramidite monomer is selected from the group consisting of formula 8a, 8b, 8c or 8d; or 9a, 9b, 9c or 9d:
formula 8a
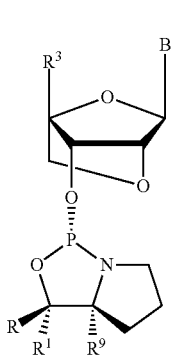
formula 8b
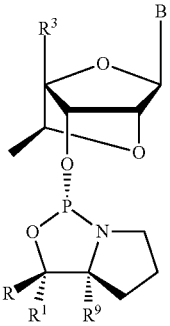
formula 8c
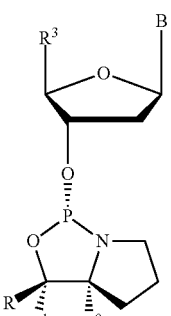
formula 8d
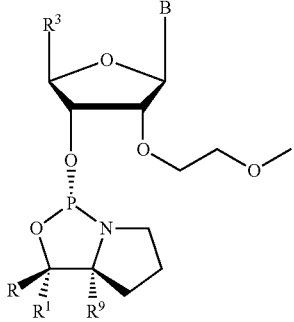
formula 9a
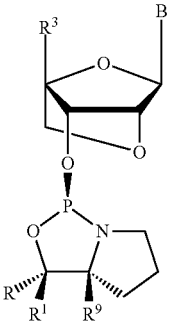
formula 9b
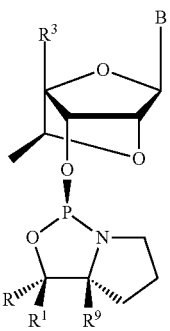

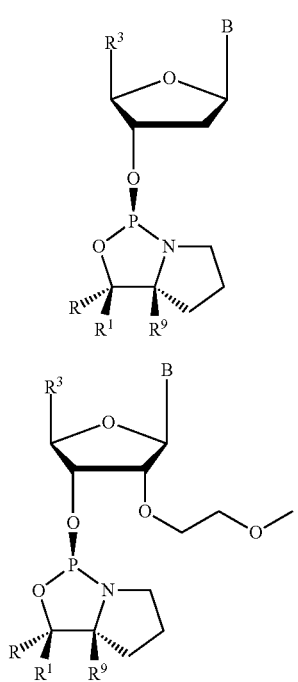

formula 9c formula 9d

In some embodiments, the nucleobase B is 9-adeninyl, such as Bz protected 9-adeninyl. In some embodiments, the nucleobase B is 1-thyminyl. In some embodiments, the monomer is a D-DNA-A monomer (e.g. the monomer is of formula 9c and the nucleobase B is 9-adeninyl, such as Bz protected 9-adeninyl). The examples illustrate that D-DNA-A monomers (e.g. of formula 9c), L-LNA-A monomers and L-LNA-T monomers (e.g. of formula 8a or 8b) show improved coupling when used in acetonitrile/aromatic heterocyclic solvents, as according to the invention.

DMF Protected L-LNA-G

As illustrated in PCT/EP2017/060985, DMF protected L-LNA-G monomers are poorly soluble in acetonitrile solvents. An L-LNA monomer can be defined either by the stereochemistry of chiral auxiliary of the monomer, or the stereochemistry of the internucleoside linkage which the monomer forms when it is incorporated into an oligonucleotide (the two features are structurally linked, and L monomer results in the creation of a Sp phosphorothioate linkage). A L-LNA monomer is represented by formula 3a, wherein in $R^4$ and $R^2$ form $R^2$ and $R^4$ together designate a bivalent bridge. See for example the monomers of formula 4a, 5a, 8a and 8b.

In some embodiments, the oxazaphospholidine phosphoramidite monomer is not an L-LNA monomer comprising a DMF protected guanine nucleobase.

In some embodiments the DMF protected guanine group (B) has the following structure:

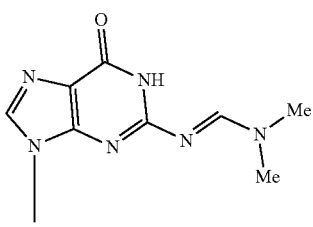 [SMILES: CN(C)/C=N/c1nc2c(ncn2C)c(=O)[nH]1]

In some embodiments, the oxazaphospholidine phosphoramidite monomer is not a monomer of formula 11 or 12:

Formula 11

Formula 12 wherein R, $R^1$, $R^3$, $R^5$, $R^6$ & $R^9$ are as according to the monomer of formula 1, and wherein for the monomer of formula 11, X and Y together designate a bivalent bridge (e.g. as per $R^2$ and $R^4$ herein, such as a bridge selected from the group consisting of bridge —C($R^aR^b$)—O—, —C($R^aR^b$) C($R^aR^b$)—O—, —CH$_2$—O—, —CH$_2$ CH$_2$—O—, —CH(CH$_3$)—O—. In some embodiments, X and Y designate the bivalent bridge —CH$_2$—O— (methylene-oxy also known as oxy-LNA) or —CH(CH$_3$)—O— (methyl-methylene-oxy). The —CH(CH$_3$)—O— bridge introduces a chiral center at the carbon atom within the bridge, in some embodiments this is in the S position (for example a nucleoside known in the art as (S)cET—see EP1984381)). In some embodiments, X and Y designate the bivalent bridge —CH$_2$—O— wherein the bridge is in the beta-D position (beta-D-oxy LNA). In some embodiments, X and Y designate the bivalent bridge —CH$_2$—O— wherein the bridge is in the alpha-L position (alpha-L-D-oxy LNA). In some embodiments, X and Y designate the bivalent bridge —CH$_2$—S— (thio LNA), or —CH$_2$—NH$_2$— (amino LNA). In the embodiments where X and Y together designate a bivalent bridge, $R^3$ may, for example be CH$_2$—O-DMTr or CH$_2$—O-MMTr. In some embodiments, the oxazaphospholidine phosphoramidite monomer is not a monomer of formula 13 or 14:

formula 13

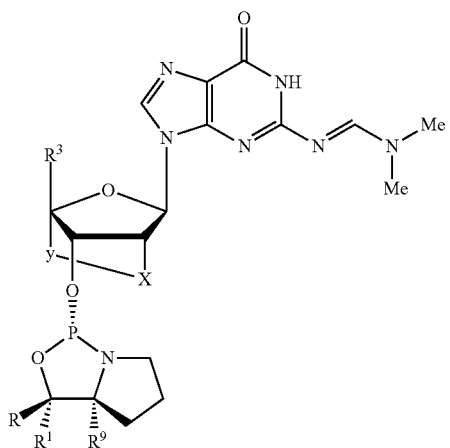

formula 14

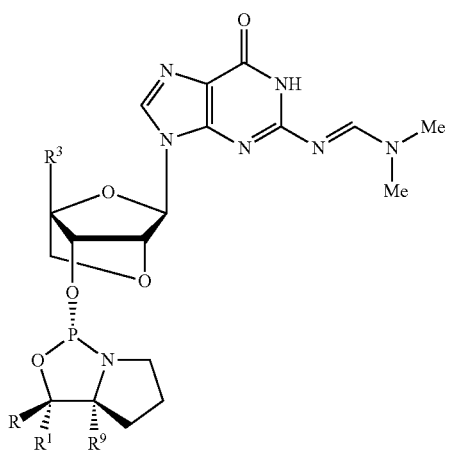

Wherein X, Y, R, $R^1$, $R^9$ and $R^3$ are as per formula 11 and 12. The exocyclic oxygen of the guanine base may optionally be protected, e.g. with a cyano group.

In some embodiments, the oxazapholidine phosphoramidite monomer is not a monomer of formula 15 or 16:

formula 15

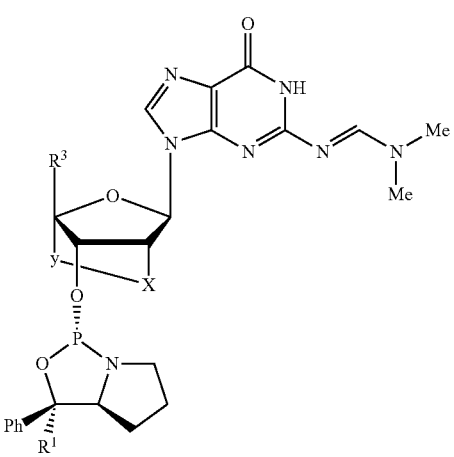

formula 16

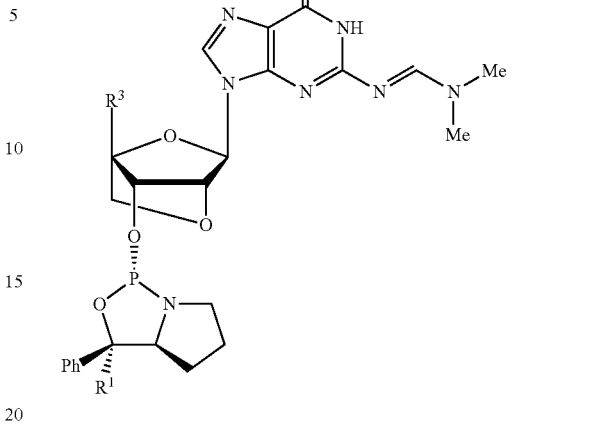

Wherein X, Y, $R^1$ and $R^3$ are as per formula 11 and 12. The exocyclic oxygen of the guanine base may optionally be protected, e.g. with a cyano group. In some embodiments of formula 15 or 16, $R^1$ is hydrogen. In some embodiments of formula 15 or 16, $R^3$ is $CH_2$—O-DMTr or $CH_2$—O-MMTr. In some embodiments, the oxazaphospholidine phosphoramidite monomer of the invention comprises an acyl protected nucleoside (Z).

Acyl Protected L-LNA-G

As illustrated in the examples, DMF protected L-LNA-G monomers are poorly soluble in acetonitrile solvents. However, we have previously identified that the use of acyl protection groups on the guanine nucleoside of L-LNA-G monomers overcomes the solubility problem.

In some embodiments, the oxazaphospholidine phosphoramidite monomer is an L-LNA monomer comprising an acyl protected guanine nucleobase, such as an isobutyryl protected guanine.

In some embodiments, the oxazaphospholidine phosphoramidite monomer is an L-LNA-G monomer of formula 23, 24, 25, 26, 27, 28, 29 or 30:

Formula 23

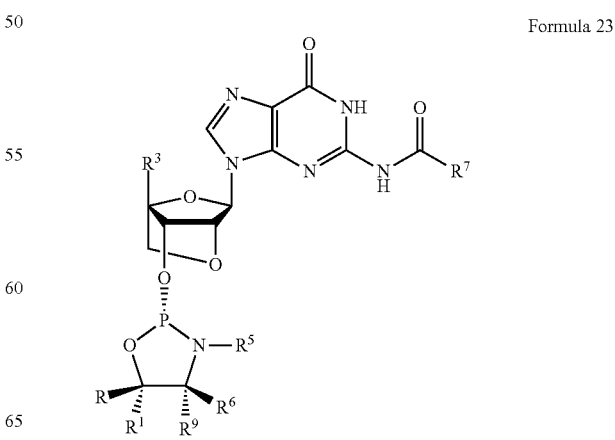

-continued
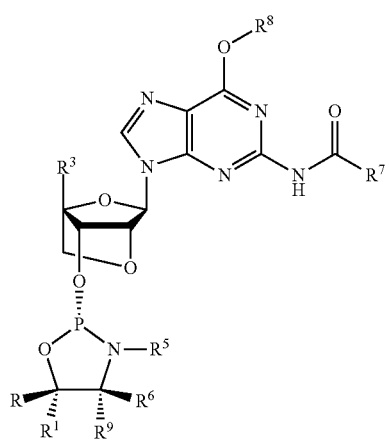
formula 24
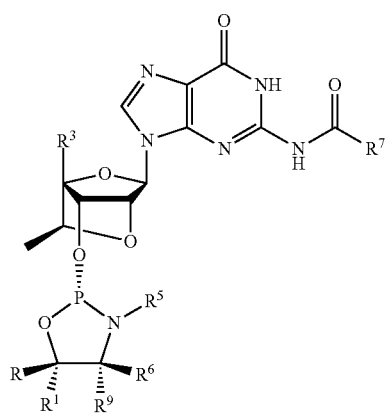
formula 25
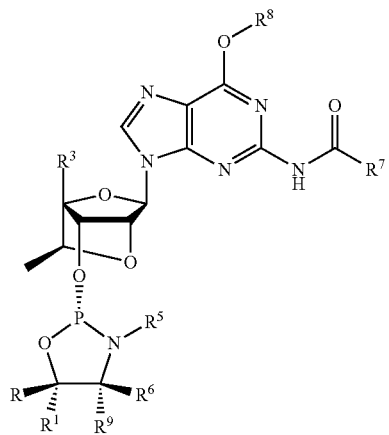
formula 26
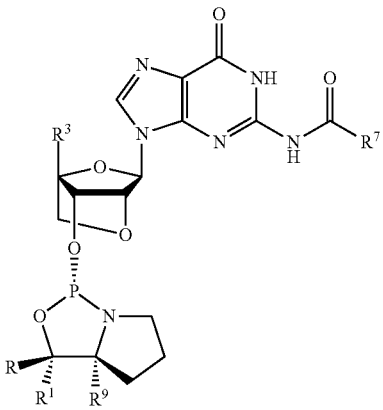
Formula 27
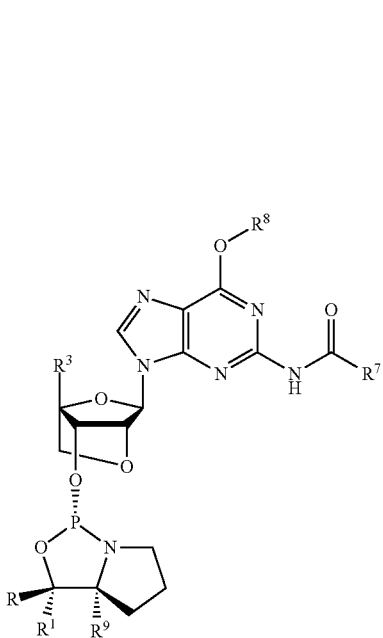
formula 28
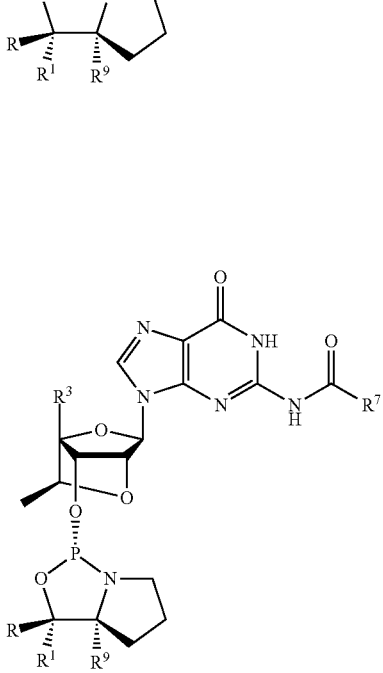
formula 29

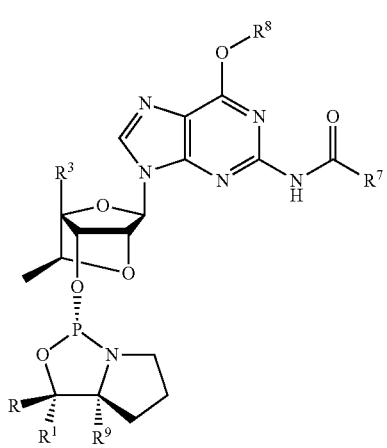

formula 30

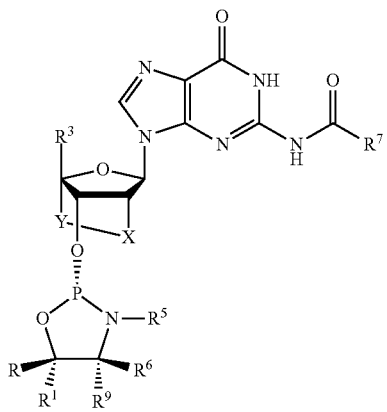

formula 31

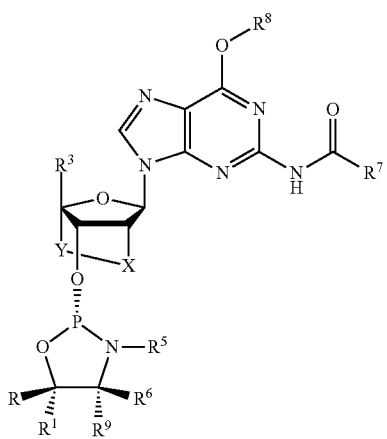

formula 32 wherein, R, $R^1$, $R^2$, $R^3$, $R^4$, $R^5$, $R^9$ and $R^6$ are as per the compound of the invention, and —C(=O)—$R^7$ is the acyl protecting group on the exocyclic nitrogen of the guanine base, and $R^8$ when present is a protecting group on the guanine exocyclic oxygen. In some embodiments $R^a$ is cyanoethyl. In some embodiments, R is phenyl, $R^1$ is hydrogen or methyl, and $R^3$ is optionally $CH_2$—O-DMTr or $CH_2$—O-MMTr. In some embodiments, $R^7$ is isobutyryl. In formula's 31 and 32, Y and X are as per formula 11.

In some embodiments, the oxazaphospholidine phosphoramidite monomer is selected from the group consisting of an L-LNA-T, D-DNA-A, D-DNA-C, L-LNA-C, and L-LNA-G (other than DMF protected L-LNA-G) or a L-DNA-C and L-DNA-T oxazaphospholidine phosphoramidite monomer. As illustrated in the examples, these monomers show an improved coupling efficacy when used in the coupling solvent compositions of the invention, in addition to the solubility and stability benefits seen with in general for oxazaphospholidine phosphoramidite monomers.

Solvent Compostions (Solutions)

In some embodiments, the coupling step b) of the method of the invention uses an acetonitrile solution comprising an oxazaphospholidine phosphoramidite monomer, acetonitrile and an aromatic heterocyclic solvent.

In some embodiments the acetonitrile solution further comprises an activator. Numerous activators for use in phosphoramidite oligonucleotide synthesis are known—they typically comprise acidic azole catalysts, such as 1H-tetrazole, 5-ethylthio-1H-tetrazole, 2-benzylthiotetrazole, and 4,5-dicyanoimidazole.

In some embodiments, the aromatic heterocyclic solvent has a pKa of about 4-about 7. In some embodiments, the aromatic heterocyclic solvent has a pKa of about 7-about 17 in water at 20° C.

In some embodiments, the aromatic heterocyclic solvent is an aromatic heterocyclic base.

In some embodiments, the aromatic heterocyclic solvent is an aromatic heterocyclic acid.

In some embodiments, the aromatic heterocyclic solvent is selected from the group consisting of pyridine, 2-picoline, 4-picoline, 3-picoline, lutidine, and pyrrole.

In some embodiments, the aromatic heterocyclic solvent is pyridine.

In some embodiments, the aromatic heterocyclic solvent is pyrrole.

In some embodiments, the aromatic heterocyclic solvent is 3-picoline.

In some embodiments, the concentration (v/v), of aromatic heterocyclic solvent in acetonitrile is between about 0.1% and about 50% (v/v). In some embodiments, the concentration (v/v), of aromatic heterocyclic solvent in acetonitrile is between about 0.5% and about 40% (v/v). In some embodiments, the concentration (v/v), of aromatic heterocyclic solvent in acetonitrile is between about 0.5% and about 30% (v/v). In some embodiments, the concentration (v/v), of aromatic heterocyclic solvent in acetonitrile is between about 0.5% and about 25% (v/v). In some embodiments, the concentration (v/v), of aromatic heterocyclic solvent in acetonitrile is between about 0.5% and about 10% (v/v). In some embodiments, the concentration (v/v), of aromatic heterocyclic solvent in acetonitrile is between about 0.5% and about 5% (v/v). In some embodiments, the concentration (v/v), of aromatic heterocyclic solvent in acetonitrile is between about 1% and about 5% (v/v). In some embodiments, the concentration (v/v), of aromatic heterocyclic solvent in acetonitrile is between about 1% and about 4% (v/v). In some embodiments, the concentration (v/v), of aromatic heterocyclic solvent in acetonitrile is between about 0.5% (v/v) and about 10% (v/v), such as between about 1% (v/v) and about 5% (v/v), such as between about 2-3% (v/v), such as about 2.5% (v/v). In these embodiments, optionally the aromatic heterocyclic base solvent is pyridine.

In some embodiments, wherein the aromatic heterocyclic solvent is pyridine, the concentration (v/v), of aromatic heterocyclic solvent in acetonitrile is between about 0.5% and about 10%, such as between about 1% and about 5%, such as between about 2-3%, such as about 2.5% or about 3.5%, or between about 2-4%.

In some embodiments, wherein the aromatic heterocyclic solvent is pyrrole, the concentration (v/v), of aromatic heterocyclic solvent in acetonitrile is between about 0.5% and about 10%, such as between about 1% and about 5%, such as between 2-4% or about 2-3%, such as about 2.5%.

In some embodiments, wherein the aromatic heterocyclic solvent is 3-picoline, the concentration (v/v), of aromatic heterocyclic solvent in acetonitrile is between about 0.5% and about 10%, such as between about 1% and about 5%, such as between 2-4%, or about 2-3%, such as about 2.5%.

Activators

Activators are reagents used prior to or during the coupling step of oligonucleotide synthesis which activate the phosphoramidite monomer to allow coupling of the monomer to the 5' terminal group attached to the solid support or oligonucleotide chain.

In some embodiments, the coupling solvent used in step b) further comprises an activator.

In some embodiments, the activator is selected from the group consisting of CMPT (N-(Cyanomethyl)pyrrolidinium triflate (CMPT), N-(phenyl)imidazolium triflate (PhIMT), benzimidazolium triflate (BIT), 4,5-dicyanoimidazole (DCI), tetrazole, and 5-(Benzylthio)-1H-tetrazole.

In some embodiments, the activator is 4,5-dicyanoimidazole (DCI).

In some embodiments, the solvent composition comprises about 0.5-about 2M DCI, such as about 1M DCI.

In some embodiments, the solvent composition further comprises N-methylimidazole, such as N-methylimidazole in a concentration of 0.01-about 1M N-methylimidazole, such as about 0.1M N-methylimidazole.

In some embodiments, the activator comprises N-methylimidazole. In some embodiments, the activator comprises 4,5-dicyanoimidazole (DCI), tetrazole, or 5-(Benzylthio)-1H-tetrazole. In some embodiments, the activator comprises 4,5-dicyanoimidazole (DCI), tetrazole, or 5-(Benzykthio)-1H-tetrazole and N-methylimidazole.

In some embodiments, the concentration of N-methylimidazole used is 0.01M-about 1M N-methylimidazole, such as about 0.1M N-methylimidazole. In some embodiments, the acetonitrile solution comprises N-methylimidazole in a concentration of 0.01M-about 1M N-methylimidazole, such as about 0.1M N-methylimidazole.

In some embodiments, the activator is DCI or tetrazole, or 5-(Benzylthio)-1H-tetrazole, which may be used at a concentration (e.g. in the acetonitrile solution of the invention) of about 0.5-about 2M, such as about 1M.

In some embodiments the activator is 4,5-dicyanoimidazole (DCI). In some embodiments, the solvent composition comprises about 0.5-about 2M DCI, such as about 1M DCI. It will be recognised that in order to optimise coupling efficacy, it may be necessary to optimize the amount of activator used, as is illustrated in the examples. In some embodiments the concentration of DCI activator uses is between 0.5M and 1M DCI. In some embodiments when the activator is DCI, the solvent composition further comprises N-methylimidazole (NMI), such as N-methylimidazole in a concentration of 0.01-about 1M N-methylimidazole, such as about 0.1M N-methylimidazole. NMI is an agent which can enhance the solubility of other activators such as DCI.

Oligonucleotide Synthesis Method

The invention provides for a method for the synthesis of an oligonucleotide, said method comprising the steps of coupling an oxazaphospholidine phosphoramidite monomer to a 5'-terminus of a solid support, a nucleoside or an oligonucleotide, to form a phosphite triester intermediate (C) followed by the step of oxidising the phosphite triester intermediate with a sulfurizing reagent (O), wherein these two steps are repeated at least once (i.e. COCO . . . ) prior to the addition of a further phosphoramidite monomer, wherein optionally there is a washing step between each coupling and oxidation step (i.e. COWCOW . . . ).

The invention provides for a method for the synthesis of a stereodefined phosphorothioate oligonucleotide, comprising the step of:
a) deprotecting a protected 5'-hydroxy terminus of a nucleoside, or oligonucleotide, attached to a solid support,
b) coupling an oxazaphospholidine phosphoramidite monomer to the deprotected 5'-hydroxy terminus of a nucleoside or oligonucleotide, to form a phosphite triester intermediate
c) oxidizing the phosphite triester intermediate with a sulfurizing reagent, followed by an optional washing step,
d) repeating steps b) and c) within the same elongation cycle,
e) optionally repeating steps a)-d) for one or more further elongation cycles,
f) deprotecting and cleavaging the oligonucleotide from the solid support.

Optionally after step d) and before step e) a capping step is performed.

An elongation cycle refers to the series of steps from deprotection, coupling, and oxidation, which results in the addition of a single nucleotide to an oligonucleotide. According to the present invention, an elongation cycle may include repeated coupling and oxidation steps within the same elongation cycle, i.e. prior to the addition of a further nucleotide (or alternatively the deprotection of the protected 5'-OH group at the start of the next elongation cycle).

In some embodiments, steps b) and c) are repeated at least three, four or five times within the same elongation cycle, optionally with a wash step after each oxidation step. Alternatively stated, in some embodiments step d) is repeated at least twice, such as at least three or four times, optionally with a wash step after each oxidation step.

The invention provides for a method for the synthesis of a stereodefined phosphorothioate oligonucleotide, comprising the step of:
a) deprotecting a protected 5'-hydroxy terminus of a nucleoside, or oligonucleotide, attached to a solid support,
b) coupling an oxazaphospholidine phosphoramidite monomer to the deprotected 5'-hydroxy terminus of a nucleoside or oligonucleotide, to form a phosphite triester intermediate and
c) oxidizing the phosphite triester intermediate with a sulfurizing reagent,
d) repeating steps b) and c) within the same elongation cycle,
e) optionally repeating steps a)-d) for one or more further elongation cycles,
f) deprotecting and cleavaging the oligonucleotide from the solid support.

The method of the invention may comprise multiple further elongation cycles e), such as 2, 3, 4, 5, 6, 7, 8, 9, 10, 11, 12, 13, 14, 15, 16, 17, 18, 19, 20 or more further elongation cycles.

In some embodiments after each coupling/oxidation steps a washing step is performed. Acetonitrile may be used as the washing solvent.

Optional Capping Step

In some embodiments after the repeated coupling and oxidation steps, such as step d), a capping step is performed. After the completion of the coupling reaction, a small percentage of the (e.g. solid support-bound) 5'-OH groups (0.1 to 1%) may remain unreacted and these can to be permanently blocked from further chain elongation to prevent the formation of oligonucleotides with an internal base deletion commonly referred to as (n−1) shortmers. Capping typically involves the acetylation of the unreacted 5'-OH groups. Therefore, capping results in the blocking of any unreacted 5'-OH groups prior to the next elongation cycle. In some embodiments, capping is performed using an anhydride such as acetic anhydride or phenoxyacetic anhydride.

The capping step can in some instances also be used for capping the secondary amine from the chiral auxiliary.

In some embodiments, after step e), an optional amine wash step is performed. The amine wash step refers to an optional procedure used in oligonucleotide synthesis wherein prior to exposure of the oligonucleotide to the strong basic conditions used in the cleavage step the oligonucleotide is treated with a solution of a weak base in an organic solvent, such as treatment with 20% diethylamine in acetonitrile, or 1:1 triethylamine/acetonitrile. The amine wash results in the removal of cyanoethyl phosphate protection groups without cleavage of the oligonucleotide from the solid support. The benefit of including an amine wash results in the avoidance of unwanted cyanothyl adducts, such as acrylonitrile, which form due to a side reaction of the cyanoethyl phosphate protection group, and heterocyclic bases, particularly thymine.

Typically, the chiral auxiliary is cleaved from the oligonucleotide during the deprotection and cleavage from the solid support. Suitable deprotection/cleavage may performed at a temperature of about 55° C. in concentrated ammonium hydroxide, for example.

In some embodiments, after step f) the oligonucleotide may be purified. The purification step may use any suitable method for oligonucleotide purification such as ion exchange purification or reversed phase chromatography, or both ion exchange purification and reversed phase chromatography. In some embodiments purification comprises the sequential steps: A) ion exchange purification, B) desalting, e.g. via diafiltration, followed by C) lyophilisation and D) reversed phase chromatography. Prior to purification it is typical that the ammonium hydroxide is either removed or at least diluted. Alternatively, DMT-ON reversed phase purification followed by detritylation is also an option for purifying oligonucleotides (see Capaldi and Scozzari, Chapter 14, Antisense Drug Technology: Principles, Strategies, and Applications. CRC Press 2008.

Detritylation can be performed using dichloroacetic or trichloroacetic acid in dichloromethane in the solid phase synthesis. Detritylation after the synthesis, cleavage, deprotection and purification can be performed using an aqueous solution of acids, due to solubility of the oligonucleotide in water.

In some embodiments, after step f) or after the optional purification step, the oligonucleotide may be conjugated. Alternatively conjugation may be performed during oligonucleotide synthesis.

Coupling Step Optimisation

The coupling step b) involves the coupling an oxazaphospholidine phosphoramidite monomer to the deprotected 5'-hydroxy terminus of a nucleoside or oligonucleotide, to form a phosphite triester intermediate. Prior to oxidation, the phosphite triester intermediate is unstable, and as such the time for the coupling step should be optimised to avoid detrimental levels of side products which can severely restrict the yield and purity of the oligonucleotide product. It appears that the side products result in the production of truncated oligonucleotides. According to the method of the invention, this problem may be reduced or avoided by performing repeated coupling and oxidation steps within one elongation cycle. The use of repeated coupling and oxidation steps results in the rapid stabilisation of the phosphite triester intermediate, by oxidation. As such the duration of each individual coupling step may be reduced. The invention therefore provides an improved method of oligonucleotide synthesis providing an enhanced yield and/or purity of the oligonucleotide product. The optimal duration of each coupling step can easily be optimised by the skilled person by measuring the level of truncated oligonucleotide products. The skilled person can then increase the number of coupling/oxidation step repeats within each elongation cycle, resulting in the improved yield and/or purity. By way of example, for small scale oligonucleotide synthesis (about 1 µM scale), a coupling time of 2-4 minutes, such as about 3 minutes, may be suitable. For larger scale synthesis longer coupling times may be employed, for example about 5 minutes for a 20 µM synthesis.

As disclosed in PCT/EP2017/060985, the use of coupling solvents comprising acetonitrile and a heterocyclic base solvent in step b) provides numerous benefits, such as enhanced solubility of the monomers, as compared to acetonitrile solutions of the monomers without the aromatic heterocyclic solvent; or the provision of more stable solutions of oxazaphospholidine phosphoramidite monomers, such as those described herein, with enhanced stability of the solutions of the monomers, as compared to acetonitrile solutions of the monomers without the aromatic heterocyclic solvent; or the provision of more reactive solutions of oxazaphospholidine phosphoramidite monomers, such as those described herein, with enhanced reactivity of the monomers, as compared to acetonitrile solutions of the monomers without the aromatic heterocyclic solvent. The skilled person will appreciate that the single of combined benefits of having higher solubility, more stable solutions, and higher reactivity, will result in a more effective synthesis and a more reliable and enhanced yield of oligonucleotide product. The benefits may also include the avoidance or reduction of unwanted side-reactions, resulting in a higher product purity.

In some embodiments, the 5' terminus is a —OH group attached to a solid support. The —OH group may be directly attached to the solid support e.g. via a linker, such as unilinker, or may be part of a nucleoside or oligonucleotide which is attached to the linker or solid support.

In some embodiments the oligonucleotide synthesis method is a solid phase phosphoramidite synthesis, wherein at least one of the coupling steps is as according to the coupling method of the invention.

In some embodiments the oligonucleotide produced by the method of the invention, stereodefined phosphorothioate oligonucleotide, is an antisense oligonucleotide or a mixed sequence oligonucleotide. In some embodiments the stereodefined phosphorothioate oligonucleotide comprises both stereodefined phosphorothioate internucleoside linkages and stereorandom phosphorothioate internucleoside linkages.

Stereorandom internucleoside linkages can be introduced via β-cyanoethyl phosphoramidites. β-cyanoethyl phosphoramidites can for example be dissolved in acetonitrile, for example at a concentration of 0.1M.

As the oxazaphospholidine phosphoramidite monomer introduce either a Sp or Rp phosphorothioate internucleoside linkage the method of the invention may be used to synthesize a stereodefined oligonucleotide. The invention therefore provides for improved methods of synthesising stereodefined phosphorothioate oligonucleotides. Typically the methods of the invention provide a yield enhancement and/or increased purity. The method of the invention may furthermore provide a more efficient use of the oxazaphospholidine phosphoramidite monomers.

In some embodiments the sequence of steps coupling (C) and oxidation (O) (step d) is performed at least twice, which may be represented as COCOCO (i.e. at least three repeat coupling/oxidation steps within the same elongation cycle). Suitable there may be a washing step (W) after each oxidation, which may be represented as COWCOWCOW.

In some embodiments the sequence of steps coupling (C) and oxidation (O) (step d) is performed at least three times, which may be represented as COCOCOCO (i.e. at least four repeat coupling/oxidation steps within the same elongation cycle). Suitable there may be a washing step (W) after each oxidation, which may be represented as COWCOWCOW-COW.

In some embodiments the sequence of steps coupling (C) and oxidation (O) (step d) is performed at least four times, which may be represented as COCOCOCOCO (i.e. at least five repeat coupling/oxidation steps within the same elongation cycle). Suitable there may be a washing step (W) after each oxidation, which may be represented as COWCOW-COWCOW.

In some embodiments the sequence of steps coupling (C) and oxidation (O) (step d) is performed at least five times, which may be represented as COCOCOCOCOCO (i.e. at least six repeat coupling/oxidation steps within the same elongation cycle). Suitable there may be a washing step (W) after each oxidation, which may be represented as COW-COWCOWCOWCOWCOW.

In some embodiments the coupling reaction takes place in an acetonitrile solvent composition. In some embodiments the acetonitrile solvent comprises acetonitrile and an aromatic heterocyclic solvent. In some embodiments the aromatic heterocyclic solvent has a pKa of 4-7 or from 7-17 in water at 20° C. In some embodiments the aromatic heterocyclic solvent is an aromatic heterocyclic base. In some embodiments the aromatic heterocyclic solvent is an aromatic heterocyclic acid. In some embodiments the aromatic heterocyclic solvent is selected from the group consisting of pyridine, 2-picoline, 4-picoline, 3-picoline, lutidine, and pyrrole. In some embodiments the aromatic heterocyclic solvent is pyridine. In some embodiments the concentration (v/v), of aromatic heterocyclic solvent in acetonitrile is between about 0.1% and about 50% (v/v), such as between about 0.5% and about 25%. In some embodiments the concentration (v/v), of aromatic heterocyclic solvent in acetonitrile is between about 0.5% and about 10%, such as between about 1% and about 5%, such as between about 2-4%, such as about 2.5%, or about 3.5%.

In some embodiments the method comprises multiple further elongation cycles (e).

In some embodiments the oxazaphospholidine phosphoramidite monomer is of formula I

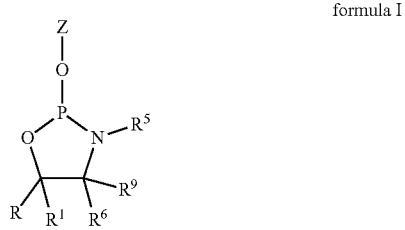

formula I wherein Z is a nucleoside,
$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula 1;
$R^9$ is hydrogen;
$R^1$ is selected from the groups consisting of hydrogen and $C_{1-3}$alkyl; and,
R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;
wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$alkoxy, $C_{6-14}$ aryl group, or $C_{6-14}$ aryl $C_{1-4}$ alkyl group.

In some embodiments the oxazaphospholidine phosphoramidite monomer is an L-LNA guanine monomer, such as a LNA-G monomer of formula selected from the group consisting of 3a, 4a, 5a, 8a and 8b, wherein the exocyclic nitrogen on the guanine residue is protected with an acyl group, such as isobutyryl.

The oligonucleotide synthesis method of the invention may comprise the steps of:
a) providing a solid support with a free 5'-OH group,
b) activation of an oxazaphospholidine phosphoramidite monomer,
c) coupling the activated oxazaphospholidine phosphoramidite monomer to the free '5-OH, to form a phosphotriester intermediate,
d) oxidizing the phosphotriester intermediate with a sulfurizing reagent, such as xanthan hydride,
e) capping any free —OH groups, for example using acetic anhydride,
f) optionally repeating steps b)-e),
g) deprotecting any remaining protection groups (global deprotection) and cleaving the oligonucleotide from the solid support, for example by treatment with ammonium hydroxide at 60° C.;
wherein the free —OH group of the solid support may optionally be attached to a nucleoside or oligonucleotide chain attached to said solid support; and wherein steps c) and d) are repeated at least once prior to step e), wherein optionally after step d) oxidation, and prior to step e), a washing step is performed. In some embodiments, steps c) and d) (CO) and when present the optional washing step (COW) are repeated once, twice, three times, four times, five times or six times, or more, prior to step e).

The solid support may be provided in a protected from, with the 5'OH group protected e.g. by a DMT group. Prior to step a), the solid support (or the terminal nucleoside attached thereto) may be be-blocked (de-tritylated) to provide the free 5'-OH group.

In some embodiments, steps b) to f) are repeated 7-25 times in the oligonucleotide synthesis, such as 7-16 times. In some embodiments the reiteration of steps b)-f) are consecutive cycles in the oligonucleotide synthesis.

Exemplary scheme for phosphoramidite oligonucleotide synthesis using oxazaphospholidine phosphoramidite monomers is shown in FIG. 24:

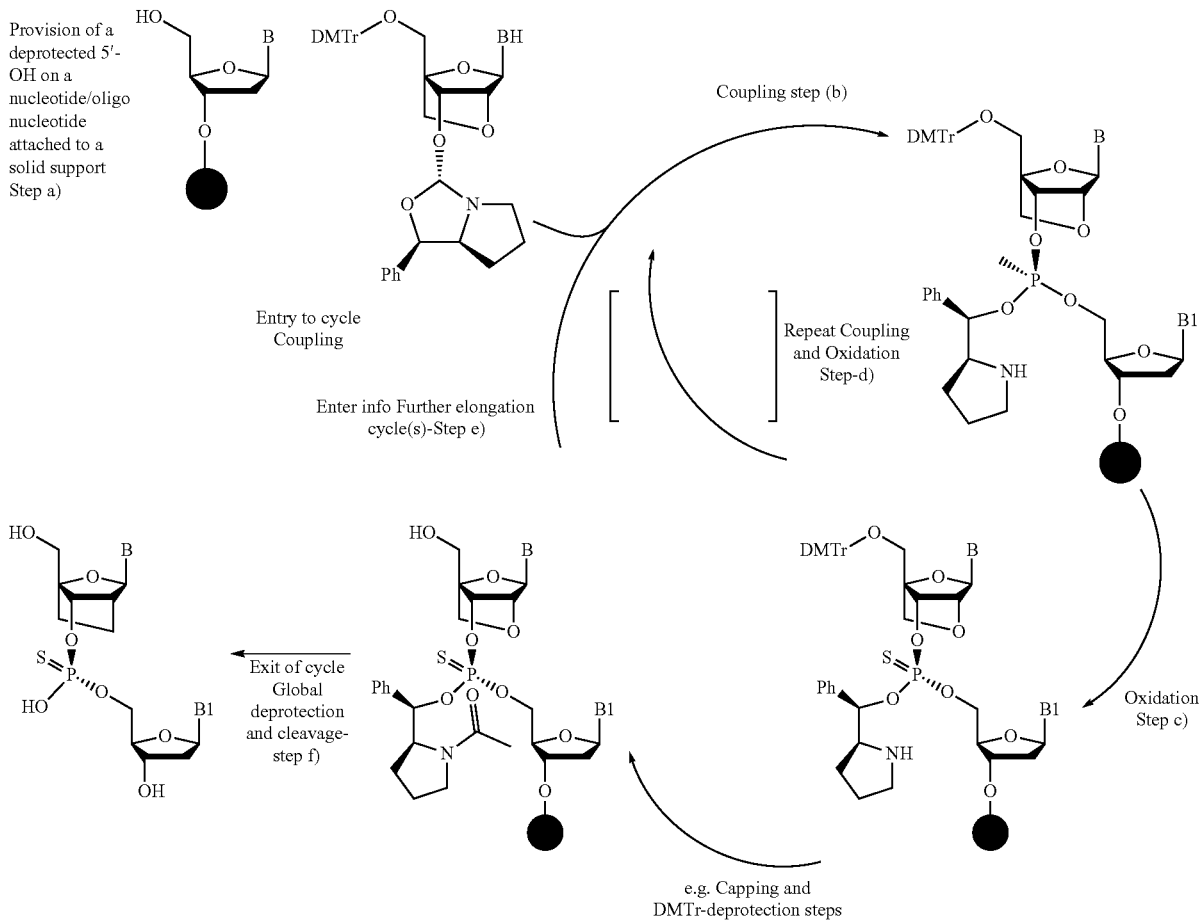

The coupling step may, for example be performed using an acetonitrile coupling solvent composition comprising acetonitrile solvent, the DMTr protected oxazaphospholidine phosphoramidite monomer (a beta-D-oxy LNA monomer is shown for illustrative purposes), a heterocyclic base solvent, such as pyridine, and a suitable activator such as DCI (1M), optionally in the presence of 0.1M NMI.

The oxidation step may, for example, be performed using Xanthan hydride 0.1M. After each oxidation step an optional washing step may be performed, e.g. using acetonitrile.

In the above scheme (also shown in FIG. 24), the optional capping step is shown, which precedes a DMTr-deprotection, prior to either exit from the cycle (step f) or a further elongation round (step e). Capping may be performed using acetic anhydride.

It will be noted that, depending on the oxazaphospholidine phosphoramidite monomer used, the capping step may also result in the protection of amine group present on the chiral auxiliary of the monomer. It will be understood that the amine group of the chiral auxiliary of the monomer, may be protected using other protection groups, for example the orthogonal protection groups disclosed in EP17163506.3.

In some embodiments, in addition to incorporation of stereodefined phosphorothioate internucleoside linkages, the method of synthesis may, through use of standard phosphoramidite monomers, incorporate stereorandom internucleoside linkages.

Step d) may be performed once, twice, three times, four times, five times or more. The length of each capping step, and the number of repeated coupling and oxidation steps (step d) may be optimised to reduce unwanted side reaction and to maximize the yield or purity of the oligonucleotide produced by the method.

Stereodefined Phosphorothioate Oligonucleotides

Typically, oligonucleotide phosphorothioates are synthesised as a random mixture of Rp and Sp phosphorothioate linkages (also referred to as a diastereomeric mixture). In the method of the present invention, phosphorothioate oligonucleotides are provided where at least one of the phosphorothioate linkages of the oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Stereodefined oligonucleotides comprise at least one phosphorothioate linkage which is stereodefined. The term stereodefined, may be used to describe a defined chirality of one or more phosphorothioate internucleoside linkages as either Rp or Sp, or may be used to described a oligonucleotide which comprises such a (or more) phosphorothioate internucleoside linkage. It is recognised that a stereodefined oligonucleotide may comprise a small amount of the alternative stereoisomer at any one position, for example Wan et al reports a 98% stereoselectivity for the gapmers reported in NAR, November 2014.

LNA Oligonucleotide

An LNA oligonucleotide is an oligonucleotide which comprises at least one LNA nucleoside. The LNA oligonucleotide may be an antisense oligonucleotide.

The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length.

The term "antisense oligonucleotide" as used herein is refers to oligonucleotides capable of modulating expression of a target gene by hybridizing to a target nucleic acid, in particular to a contiguous sequence on a target nucleic acid. An antisense oligonucleotide can also be defined by it's complementary to a target nucleic acid. Antisense oligonucleotides are single stranded. Antisense oligonucleotides are not essentially double stranded and are not therefore siRNAs. An antisense oligonucleotide comprises a contiguous nucleotide which is complementary to a target nucleic acid. Antisense oligonucleotides typically comprise one or more modified internucleoside linkages, and may by way of a non-limiting example be in the form of a LNA gapmer or a mixed wing gapmer. In other embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'-MOE nucleotides), or a LNA totalmers (only LNA nucleotides—see. E.g. WO2009/043353 hereby incorporated by reference).

The term "modified internucleoside linkage" is defined as generally understood by the skilled person as linkages other than phosphodiester (PO) linkages, that covalently couples two nucleosides together. Modified internucleoside linkages are particularly useful in stabilizing oligonucleotides for in vivo use, and may serve to protect against nuclease cleavage. A phosphorothioate internucleoside linkage is particularly useful due to nuclease resistance, beneficial pharmacokinetics and ease of manufacture. In some embodiments at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate, wherein at least one of the phosphorothioate internucleoside linkages is a stereodefined phosphorothioate internucleoside linkage (originating from the incorporation of the oxazaphospholidine phosphoramidite monomer into the oligonucleotide during oligonucleotide synthesis). Further internucleoside linkers are disclosed in WO2009/124238 (incorporated herein by reference).

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In some embodiments the nucleobase moiety is modified by modifying or replacing the nucleobase. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Modified nucleosides and nucleotides are modified as compared to the equivalent DNA or RNA nucleoside/tide by the introduction of a modification to the ribose sugar moiety, the nucleobase moiety, or in the case of modified nucleotides, the internucleoside linkage. Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. The term modified nucleoside may also be used herein interchangeably with the term "nucleoside analogue" or modified "units" or modified "monomers". Examples of modified nucleosides are described in the separate section "Oligomer modifications" and its sub-sections.

Acyl Protected Exocyclic Nitrogen

The exocyclic nitrogen group of guanine is illustrated below (encircled). This group is protected by an acyl group in the monomer used in the invention. The oxygen group may optionally also be protected, e.g. with a cyano group.

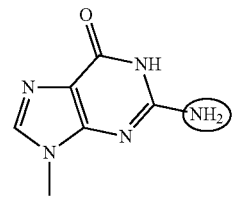

Locked Nucleic Acid Nucleosides (LNA).

LNA nucleosides are modified nucleosides which comprise a linker group (referred to as a biradicle or a bridge) between C2' and C4' of the ribose sugar ring of a nucleotide (i.e. the embodiment where $R^2$ and $R^4$ together designate a bivalent bridge).

These nucleosides are also termed bridged nucleic acid or bicyclic nucleic acid (BNA) in the literature.

In some embodiments, the oxazaphospholidine phosphoramidite monomer is or comprises a LNA nucleoside, for example the monomer may be of formula 17 or formula 18

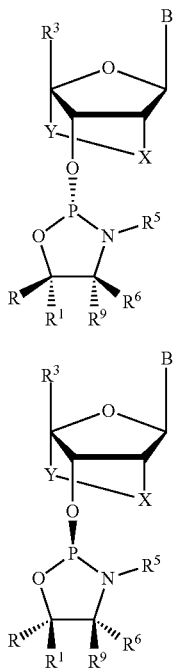

Formula 17

Formula 18

Wherein B designates the nucleobase; R, $R^1$, $R^6$, $R^3$, $R^9$, $R^5$ are as according to formula 1.

In some embodiments of formula 17, B is other than DMF protected guanine. In some embodiments B is either adenine or thymine. In some embodiments B is DMF protected adenine.

X designates a group selected from the list consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, $NR^a R^b$, —CH$_2$—, $CR^a R^b$, —C(=CH$_2$)—, and —C(=$CR^a R^b$)—

In some embodiments, X is —O—

Y designates a group selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C($R^a R^b$)—, —CH$_2$CH$_2$—, —C($R^a R^b$)—C($R^a R^b$)—, —CH$_2$CH$_2$CH$_2$—, —C($R^a R^b$)C($R^a R^b$)C($R^a R^b$)—, —C($R^a$)=C($R^b$)—, and —C($R^a$)=N—

In some embodiments, Y is selected from the group consisting of: —CH$_2$—, —CHR$^a$—, —CHCH$_3$—, $CR^a R^b$— or —X—Y— together designate a bivalent linker group (also referred to as a radicle) together designate a bivalent linker group consisting of 1, 2, or 3 groups/atoms selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, In some embodiments, —X—Y— designates a biradicle selected from the groups consisting of: —X—CH$_2$—, —X—$CR^a R^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$—, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—$CR^a R^b$— and —S—CHR$^a$—.

In some embodiments —X—Y— designates —O—CH$_2$— or —O—CH(CH$_3$)—.

and R$^a$ and, when present R$^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation.

$R^{10}$ may be hydrogen or in some embodiments may be selected from the group consisting of: optionally substituted $C_{1-6}$-alkyl, optionally substituted $C_{2-6}$-alkenyl, optionally substituted $C_{2-6}$-alkynyl, hydroxy, $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted, and where two geminal substituents together may designate oxo, thioxo, imino, or optionally substituted methylene.

In some embodiments $R^{10}$ is selected from $C_{1-6}$ alkyl, such as methyl, and hydrogen.

In some embodiments $R^{10}$ is hydrogen.

In some embodiments, R$^a$ is either hydrogen or methyl. In some embodiments, when present, R$^b$ is either hydrogen or methyl.

In some embodiments, one or both of R$^a$ and R$^b$ is hydrogen

In some embodiments, one of R$^a$ and R$^b$ is hydrogen and the other is other than hydrogen In some embodiments, one of R$^a$ and R$^b$ is methyl and the other is hydrogen In some embodiments, both of R$^a$ and R$^b$ are methyl.

In some embodiments, the biradicle —X—Y— is —O—CH$_2$—, and $R^{10}$ is hydrogen. In some embodiments, the biradicle —X—Y— is —S—CH$_2$—, and $R^{10}$ is hydrogen.

In some embodiments, the biradicle —X—Y— is —NH—CH$_2$—, and $R^{10}$ is hydrogen.

In some embodiments, the biradicle —X—Y— is —O—CH$_2$—CH$_2$— or —O—CH$_2$—CH$_2$—CH$_2$—, and $R^{10}$ is hydrogen.

In some embodiments, the biradicle —X—Y— is —O—CH$_2$—, and $R^{10}$ is $C_{1-6}$ alkyl, such as methyl.

In some embodiments, the biradicle —X—Y— is —O—$CR^a R^b$, wherein one or both of R$^a$ and R$^b$ are other than hydrogen, such as methyl, and $R^{10}$ is $C_{1-6}$ alkyl, such as methyl.

In some embodiments, the biradicle —X—Y— designate the bivalent linker group —O—CH(CH$_2$OCH$_3$)— (2'

O-methoxyethyl bicyclic nucleic acid—Seth at al., 2010, J. Org. Chem., 2010. 75 (5), pp 1569-1581). In some embodiments, the biradicle —X—Y— designate the bivalent linker group —O—CH(CH$_2$CH$_3$)— (2'O-ethyl bicyclic nucleic acid—Seth at al., 2010, J. Org. Chem). In some embodiments, the biradicle —X—Y— is —O—CHR$^a$—, and R$^{10}$ is hydrogen.

In some embodiments, the biradicle —X—Y— is —O—CH(CH$_2$OCH$_3$)—, and R$^{10}$ is hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)— in either the R- or S-configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, and R$^{10}$ is hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L).

In some embodiments, the biradicle —X—Y— is —O—CR$^a$R$^b$—, wherein in neither R$^a$ or R$^b$ is hydrogen, and R$^{10}$ is hydrogen. In some embodiments, R$^a$ and R$^b$ are both methyl.

In some embodiments, the biradicle —X—Y— is —S—CHR$^a$—, and R$^{10}$ is hydrogen.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—, and R$^{10}$ is hydrogen.

In some embodiments the biradicle —X—Y— is —N(OR$^a$)—, and R$^{10}$ is hydrogen. In some embodiments R$^a$ is C$_1$, alkyl such as methyl. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^a$)—, and R$^{10}$ is hydrogen. In some embodiments R$^a$ is C$_{1-6}$ alkyl such as methyl.

In some embodiments, and R$^{10}$ is C$_{1-6}$ alkyl such as methyl. In such an embodiment, the biradicle —X—Y— may be selected from —O—CH$_2$— or —O—C(HCR$^a$)—, such as —O—C(HCH$_3$)—.

In some embodiments, the biradicle is —CR$^a$R$^b$O—CR$^a$R$^b$—, such as CH$_2$—O—CH$_2$—, and R$^{10}$ is hydrogen. In some embodiments R$^a$ is C$_{1-6}$ alkyl such as methyl.

In some embodiments, the biradicle is —O—CR$^a$R$^b$—O—CR$^a$R$^b$—, such as O—CH$_2$—O—CH$_2$—, and R$^{10}$ is hydrogen. In some embodiments R$^a$ is C$_{1-6}$ alkyl such as methyl.

It will be recognized than, unless specified, the LNA nucleosides may be in the beta-D or alpha-L stereoisoform.

As illustrated in the examples, in some embodiments of the invention the LNA nucleosides are or comprise beta-D-oxy-LNA nucleosides, such as where the 2'-4' bridge is as per formula I, and where X is oxygen, Y is CH$_2$, and R$^{10}$ is hydrogen.

DNA Nucleosides

In some embodiments, the oxazaphospholidine phosphoramidite monomer is or comprises a DNA nucleoside, for example the monomer may be of formula 19 or formula 20:

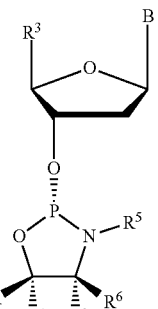

Formula 19

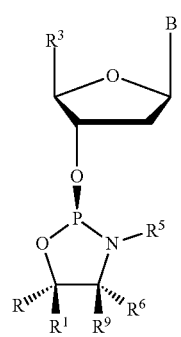

Formula 20

Wherein B designates the nucleobase; R, R$^1$, R$^6$, R$^3$, R$^9$, R$^5$ are as according to formula 1. In some embodiments of formula 20, B is adenine, such as protected adenine, such as Bz protected adenine.

In some embodiments, the oxazaphospholidine phosphoramidite monomer is as according to formula 21 and 22:

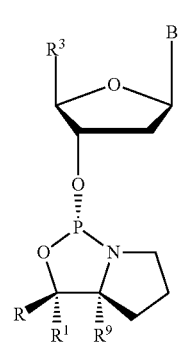

formula 21

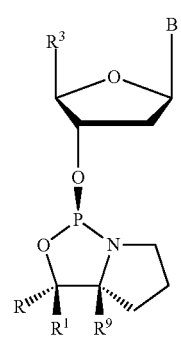

formula 22

Wherein B designates the nucleobase; R, R$^1$, R$^3$, R$^9$, are as according to formula 1. In some embodiments of formula 20 or 22, B is adenine, such as protected adenine, such as Bz protected adenine. In some embodiments of the monomer of formula 19, 20, 21, or 22, R is phenyl, and $R^1$ is either hydrogen or methyl. In some embodiments of the monomer of formula 19, 20, 21 or 22, $R^3$ is $CH_2$—O-DMTr or $CH_2$—O-MMTr.

Oligonucleotides Comprising DNA and/or Affinity Enhancing Nucleosides

In some embodiments, the oligonucleotide is a DNA phosphorothioate oligonucleotide. DNA phosphorothioate oligonucleotides comprise only DNA nucleosides, and in some embodiments may comprise only stereodefined phosphorothioate internucleoside linkages. DNA phosphorothioates may for example be 18-25 nucleotides in length.

In some embodiments, the oligonucleotide comprises one or more affinity enhancing nucleosides, such as LNA or 2' substituted nucleosides described herein. Affinity enhancing nucleosides, such as 2'-O-MOE or 2'-Omethyl are often used in antisense oligonucleotides, either in combination with other nucleosides, such as DNA nucleosides, in the form of, e.g. mixmers or gapmers, or may be used in fully sugar modified oligonucleotides, where all of the nucleosides are other than DNA or RNA.

In some embodiments the oligonucleotide synthesised by the method of the invention may be a gapmer, and LNA gapmer, or a mixed wing gapmer.

In some embodiments of the method of the invention, the oxazapholidine phosphoramidite monomer is of formula 33 (FIG. 17).

In some embodiments of the method of the invention, the oxazapholidine phosphoramidite monomer is of formula 34 (FIG. 17).

In some embodiments of the method of the invention, the oxazapholidine phosphoramidite monomer is of formula 35 (FIG. 17).

In some embodiments of the method of the invention, the oxazapholidine phosphoramidite monomer is of formula 36 (FIG. 17).

In some embodiments of the method of the invention, the oxazapholidine phosphoramidite monomer is of formula 37 (FIG. 17).

In some embodiments of the method of the invention, the oxazapholidine phosphoramidite monomer is of formula 38 (FIG. 17).

In some embodiments of the method of the invention, the oxazapholidine phosphoramidite monomer is of formula 39 (FIG. 17).

In some embodiments of the method of the invention, the oxazapholidine phosphoramidite monomer is of formula 40 (FIG. 17).

In some embodiments of the method of the invention, the oxazapholidine phosphoramidite monomer is of formula 41 (FIG. 18).

In some embodiments of the method of the invention, the oxazapholidine phosphoramidite monomer is of formula 42 (FIG. 18).

In some embodiments of the method of the invention, the oxazapholidine phosphoramidite monomer is of formula 43 (FIG. 18).

In some embodiments of the method of the invention, the oxazapholidine phosphoramidite monomer is of formula 44 (FIG. 18).

In some embodiments of the method of the invention, the oxazapholidine phosphoramidite monomer is of formula 45 (FIG. 18).

In some embodiments of the method of the invention, the oxazapholidine phosphoramidite monomer is of formula 46 (FIG. 18).

In some embodiments of the method of the invention, the oxazapholidine phosphoramidite monomer is of formula 47 (FIG. 18).

In some embodiments of the method of the invention, the oxazapholidine phosphoramidite monomer is of formula 48 (FIG. 18).

In some embodiments the oxazapholidine phosphoramidite monomer is a DNA monomer.

In some embodiments the oxazapholidine phosphoramidite monomer is a LNA monomer.

In some embodiments, the oxazapholidine phosphoramidite monomer is a LNA-A (either a D-LNA-A or an L-LNA-A) monomer.

In some embodiments, the oxazapholidine phosphoramidite monomer is a LNA-C (either a D-LNA-A or an L-LNA-A) monomer.

In some embodiments, the oxazapholidine phosphoramidite monomer is an L-LNA-G (either a D-LNA-A or an L-LNA-A) monomer, such as a L-LNA-G wherein the exocyclic nitrogen of the guanine residue is protected with an acyl protection group such as isobutyryl.

In some embodiments, oxazapholidine phosphoramidite monomer is other than an L-LNA-G monomer wherein the exocyclic nitrogen on the guanine residue is protected with a DMF protection group. In some embodiments, oxazapholidine phosphoramidite monomer is other than a D-LNA-G monomer.

In some embodiments, the oxazapholidine phosphoramidite monomer is other than a LNA-T monomer, such as D-LNA-T or L-LNA-T.

In some embodiments, the oxazapholidine phosphoramidite monomer is other than a LNA-T monomer, such as D-LNA-T or L-LNA-T or a D-LNA-G monomer.

In some embodiments, the oxazapholidine phosphoramidite monomer is a DNA monomer, or is a LNA monomer selected from the group consisting of a LNA-A monomer, a LNA-C monomer and an acyl protected L-LNA-G monomer.

In some embodiments, the oxazapholidine phosphoramidite monomer is other than a LNA-T monomer, a D-LNA-G monomer, or a DMF protected L-LNA-G monomer.

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides). In some embodiments the stereodefined phosphorothioate oligonucleotide is a gapmer oligonucleotide such as an LNA gapmer oligonucleotide.

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-DNA, arabino nucleic acid (ANA), 2'-fluoro-ANA and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The method of the present invention is particularly suitable for the purification of short oligonucleotides, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

Mixed Sequence Oligonucleotides

The oligonucleotide synthesised using the method of the invention may be a mixed sequence oligonucleotide. The invention provides for a method for the synthesis of manufacture of a mixed sequence oligonucleotide. A mixed sequence oligonucleotide comprises at least two such as at least three of at least four different base moieties (e.g. selected from the group consisting of A, T, C, or G, wherein C is optionally 5-methyl-cytosine). Antisense oligonucleotides are typically mixed sequence oligonucleotides.

Further Embodiments of the Invention

The invention provides

1. A method for the synthesis of a stereodefined phosphorothioate oligonucleotide, comprising the step of:
   a) deprotect a protected 5'-hydroxy terminus of a nucleoside, or oligonucleotide, attached to a solid support.
   b) coupling (C) an oxazaphospholidine phosphoramidite monomer to the deprotected 5'-hydroxy terminus of a nucleoside or oligonucleotide, wherein optionally said coupling reaction takes place in an acetonitrile solvent composition comprising acetonitrile and an aromatic heterocyclic solvent, to form a phosphite triester intermediate and
   c) oxidizing (O) the phosphite triester intermediate with a sulfurizing reagent.
   d) optionally repeating steps a)-c) for one or more further elongation cycles,
   e) deprotection and cleavage of the oligonucleotide from the solid support; wherein steps b) and c) are repeated at least once in each elongation cycle.

2. A method according to embodiment 2, wherein said method comprises multiple further elongation cycles (d).

3. The method according to embodiment 3, wherein the stereodefined phosphorothioate oligonucleotide is an antisense oligonucleotide.

4. The method according to any one of embodiments 1-3, wherein after steps b) and c) a washing step (W) is performed (i.e. the method comprises the steps COWCOW in the same elongation cycle).

5. The method according to any one of embodiments 1-3, wherein the aromatic heterocyclic solvent has a pKa of 4-7 or from 7-17 in water at 20° C.

6. The method according to any one of embodiments 1-5, wherein the aromatic heterocyclic solvent is an aromatic heterocyclic base.

7. The method according to any one of embodiments 1-5, wherein the aromatic heterocyclic solvent is an aromatic heterocyclic acid.

8. The method according to any one of embodiments 1-5, wherein the aromatic heterocyclic solvent is selected from the group consisting of pyridine, 2-picoline, 4-picoline, 3-picoline, lutidine, and pyrrole.

9. The method according to any one of embodiments 1-8, wherein the aromatic heterocyclic solvent is pyridine.

10. The method according to any one of embodiments 1-9, wherein the concentration (v/v), of aromatic heterocyclic solvent in acetonitrile is between about 0.1% and about 50% (v/v), such as between about 0.5% and about 25%.

11. The method according to any one of embodiments 1-9, wherein the concentration (v/v), of aromatic heterocyclic solvent in acetonitrile is between about 0.5% and about 10%, such as between about 1% and about 5%, such as between about 2-4%, such as about 2.5%, or about 3.5%.

12. The method according to any one of embodiments 1-11, wherein the acetonitrile solvent composition further comprises an activator.

13. The method according to embodiment 12, wherein the activator is selected from the group consisting of CMPT (N-(Cyanomethyl)pyrrolidinium triflate (CMPT), N-(phenyl)imidazolium triflate (PhIMT), benzimidazolium triflate (BIT), 4,5-dicyanoimidazole (DCI), tetrazole, and 5-(Benzylthio)-1H-tetrazole.

14. The method according to embodiment 13, wherein the activator is 4,5-dicyanoimidazole (DCI).

15. The method according to any one of embodiments 1-14, wherein the solvent composition comprises about 0.5-about 2M DCI (or the other activators of embodiment 13), such as about 1M DCI (or the other activators of embodiment 13).

16. The method according to any one of embodiments 12-15, wherein the solvent composition further comprises N-methylimidazole, such as N-methylimidazole in a concentration of 0.01-about 1M N-methylimidazole, such as about 0.1M N-methylimidazole.

17. The method according to any one of embodiments 1-16, wherein the oxazaphospholidine phosphoramidite monomer is a compound of formula I

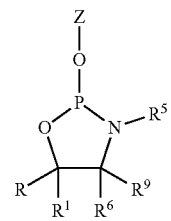

formula I wherein Z is a nucleoside, $R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula 1;

$R^9$ is hydrogen;

$R^1$ is selected from the groups consisting of hydrogen and $C_{1-3}$ alkyl; and, R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

18. The method according to any one of embodiments 1-17, wherein the oxazaphospholidine phosphoramidite monomer is a compound of

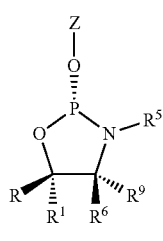

Formula 1a

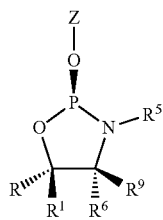

Formula 1b wherein Z, R, $R^1$, $R^6$, $R^9$ and $R^5$ are all as according to embodiment 17.

19. The method according to embodiment 17 or 18, wherein R is selected from the group consisting of aryl, heteroaryl, substituted aryl and substituted heteroaryl.

20. The method according to any one of embodiments 17-19, wherein R is aryl, such as phenyl.

21. The method according to any one of embodiments 17-20, wherein $R^1$ is hydrogen.

22. The method according to any one of embodiments 17-21, wherein $R^1$ is $C_{1-3}$ alkyl, such as methyl.

23. The method according to any one of embodiments 17-22, wherein $R^5$ and $R^6$ together form a heterocyclic ring comprising 3-16 (e.g. 4) carbon atoms, together with the N atom of formula (I), (Ia) or (Ib).

24. The method according to any one of embodiments 17-22, wherein $R^5$ and $R^6$ together form a heterocyclic ring comprising 4 carbon atoms, together with the N atom of formula (I), (Ia) or (Ib).

25. The method according to any one of embodiments 1-24 wherein, the phosphoramidite monomer compound is of formula 2a or 2b

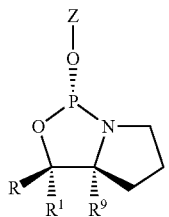

Formula 2a

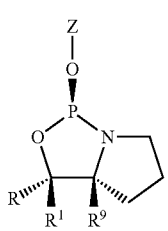

Formula 2b wherein Z, R, and $R^1$ are as according to any one of embodiments 17-24.

26. The method according to any one of embodiments 1-25, wherein the oxazaphospholidine phosphoramidite monomer compound is of formula 3a or 3b

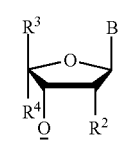

Formula 3a

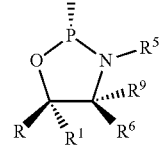

Formula 3b wherein,

R, $R^1$, $R^5$, $R^6$ and $R^9$ are as according to any one of embodiments 2-18;

B is the a nucleobase group;

$R^3$= is selected from the group consisting of CH$_2$ODMTr, CH$_2$-Alkyl-O-DMTr, CH-Me-O-DMTr, CH$_2$OMMTr, CH$_2$-Alkyl-O-MMTr, CH(Me)-O-MMTr, CH—$R^a$—O-DMTrR$^b$, and CH—$R^a$—O-MMTrR$^b$; $R^2$ is selected from the groups consisting of halo, such as —F, amino, azido, —SH, —CN, —OCN, —CF$_3$, —OCF$_3$, —O($R_m$)-alkyl, —S($R_m$)-alkyl, —N($R_m$)-alkyl, —O($R_m$)-alkenyl, —S($R_m$)-alkenyl, —N($R_m$)-alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$O—N (R$_m$)(R$_n$) or O—CH$_2$C(=O)—N(R$_m$)(R$_n$), —O—

(CH$_2$)$_2$OCH$_3$, and —O—CH$_3$, where each R$_m$ and R$_n$ are independently, H, an amino protecting group or substituted or unsubstituted C$_{1-10}$ alkyl;

R$^4$=is selected from the group consisting of alkyl, cyclo-alkyl, cyclo-heteroalkyl, O-alkyl, S-alkyl, NH-alkyl, and hydrogen;

or R$^2$ and R$^4$ together designate a bivalent bridge consisting of 1, 2, 3 groups/atoms selected from the group consisting of —C(R$^a$R$^b$)—, —C(R$^a$)=C(R$^b$), —C(R$^a$)=N, O, —Si(R$^1$)$_2$—, S—, —SO$_2$—, —N(R$^a$)—,
and >C=Z;

wherein R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryl¬oxy-carbonyl, aryloxy, arylcarbonyl, heteroaryl, hetero¬aryloxy-carbonyl, heteroaryloxy, heteroarylcarbonyl, amino, mono- and di(C$_{1-6}$-alkyl) amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulpha-nyl, C$_{1-6}$-alkylthio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation.

27. The method according to any one of embodiments 1-26, wherein the oxazaphospholidine phosphoramidite monomer is selected from the group consisting of formula 4a, 4b, 5a, 5b, 6a, 6b, 7a and 7b.

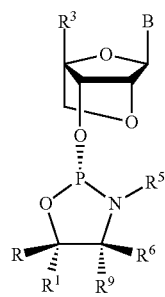

Formula 4a

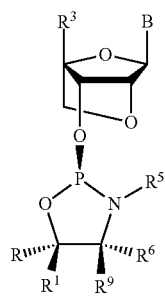

Formula 4b

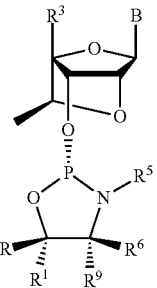

Formula 5a

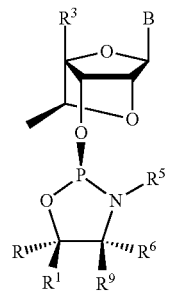

Formula 5b

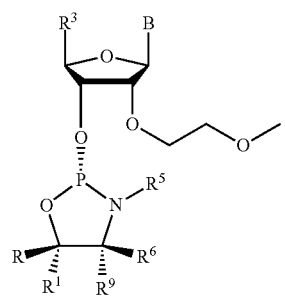

Formula 6a

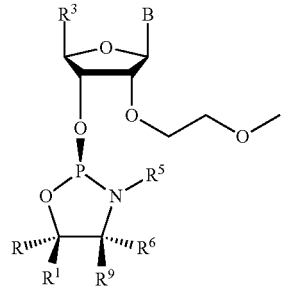

Formula 6b

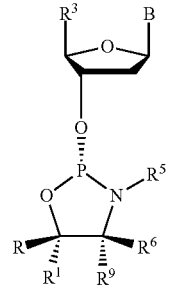

Formula 7a

Formula 7b

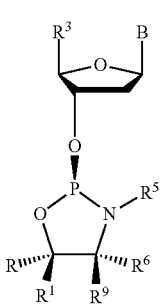

wherein R, $R^1$, $R^3$, $R^9$, $R^5$, $R^6$ and B are as according to embodiment 26.

28. The method according to any one of embodiments 1-27, wherein the oxazaphospholidine phosphoramidite monomer comprises a nucleobase moiety is a purine or a pyrimidine, such as a nucleobase selected from the group consisting of 9-adeninyl, 9-guaninyl, 1-uracil, 1-thyminyl, 1-cytosinyl, 1-isocytosinyl, 1-pseudoisocytosinyl, 1-5-methyl-cytosinyl, 1-5-thiozolyl-cytosinyl, 1-5-propynyl-cytosinyl, 1-5-propynyl-uracil, 1-5-bromo-uracil, 1-5-thiozolyl-uracil, 1-2-thio-uracil, 1-2-thio-thyminyl, 9-diaminopurinyl, 9-6-aminopurinyl, 9-2-aminopurinyl, and 9-2-chloro-6-aminopurinyl.

29. The method according to any one of embodiments 1-28, wherein the oxazaphospholidine phosphoramidite monomer is selected from the group consisting of M1-M40.

30. The method according to any one of embodiments 1-29, wherein the base moiety (B) in the oxazaphospholidine phosphoramidite monomer comprises an adenine base.

31. The method according to any one of embodiments 1-30, wherein the base moiety (B) in the oxazaphospholidine phosphoramidite monomer comprises a thymine base.

32. The method according to any one of embodiments 1-30, wherein the base moiety (B) in the oxazaphospholidine phosphoramidite monomer comprises a guanine base.

33. The method according to any one of embodiments 1-30, wherein the base moiety (B) in the oxazaphospholidine phosphoramidite monomer comprises a cytosine base.

34. The method according to any one embodiments 1-33, wherein the oxazaphospholidine phosphoramidite monomer is a L monomer.

35. The method according to any one embodiments 1-33, wherein the oxazaphospholidine phosphoramidite monomer is a D monomer.

36. The method according to any one of embodiments 1-35, wherein the oxazaphospholidine phosphoramidite monomer is an LNA monomer, such as a beta-D-oxy LNA monomer.

37. The method according to any one of embodiments 1-36, wherein the oxazaphospholidine phosphoramidite monomer is a DNA monomer.

38. The method according to any one of embodiments 1-28, wherein the oxazaphospholidine phosphoramidite monomer is selected from the group consisting of formula 8a or formula 8b Formula 8a

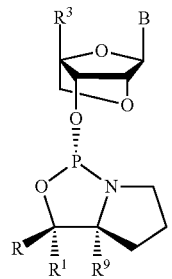

Formula 8b

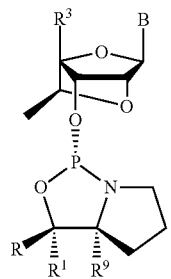

wherein B is thymine, and wherein R, $R^1$, $R^3$ and $R^9$ are as according to any one of embodiments 17-24.

39. The method according to any one of embodiments 1-28, wherein the oxazaphospholidine phosphoramidite monomer is selected from the group consisting of formula 8a or formula 8b Formula 8a

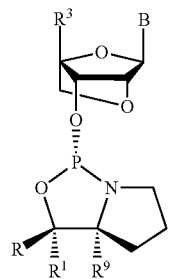

Formula 8b

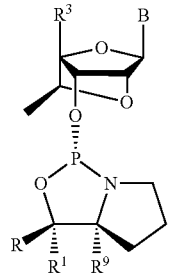

wherein B is adenine, and wherein R, $R^1$, $R^3$ and $R^9$ are as according to any one of embodiments 17-24, wherein the adenine it may optionally be protected, e.g. with benzoyl).

40. The method according to any one of embodiments 1-28, wherein the oxazaphospholidine phosphoramidite monomer is selected from the group consisting of a D-DNA-A or a L-DNA-A monomer, such as a oxazaphospholidine phosphoramidite monomer of formula

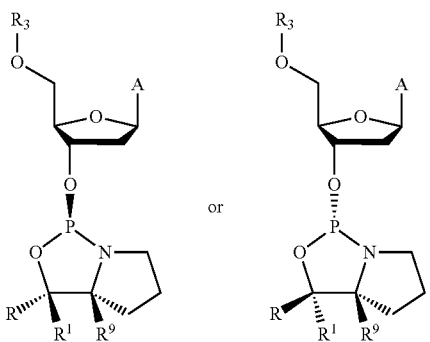

wherein A is adenine, and wherein R, $R^1$, $R^3$ and $R^9$ are as according to any one of embodiments 1-24, wherein the base adenine may be protected. e.g. with benzoyl.

41. The method according to any one of embodiments 1-28, wherein the oxazaphospholidine phosphoramidite monomer is selected from the group consisting of a D-DNA-T or a L-DNA-T monomer, such as a oxazaphospholidine phosphoramidite monomer of formula

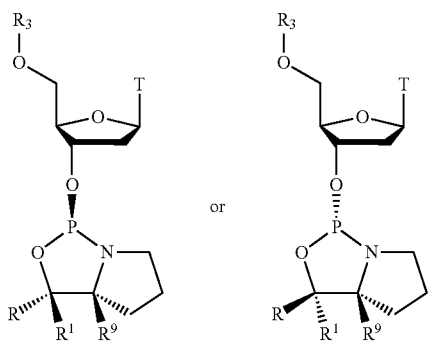

wherein T is thymine, and wherein R, $R^1$, $R^3$ and $R^9$ are as according to any one of embodiments 1-24.

42. The method according to any one of embodiments 1-28, wherein the oxazaphospholidine phosphoramidite monomer is selected from the group consisting of a D-DNA-C or a L-DNA-C monomer, such as a oxazaphospholidine phosphoramidite monomer of formula

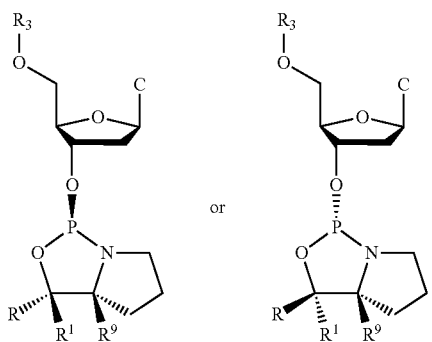

wherein C is cytosine, and wherein R, $R^1$, $R^3$ and $R^9$ are as according to any one of embodiments 1-24, and wherein the base cytosine may be protected, e.g. with acetyl or benzoyl, and wherein optionally cytosine is 5-methyl cytosine.

43. The method according to any one of embodiments 1-28, wherein the oxazaphospholidine phosphoramidite monomer is selected from the group consisting of a D-DNA-G or a L-DNA-G monomer, such as a oxazaphospholidine phosphoramidite monomer of formula

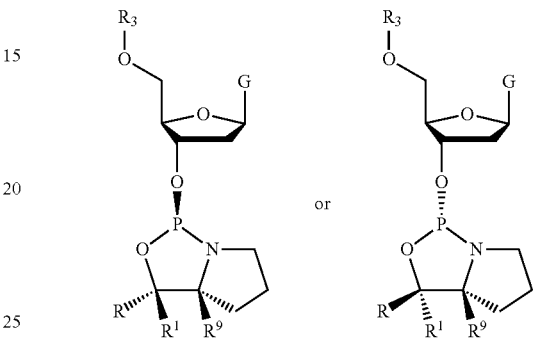

wherein G is guanine, and wherein R, $R^1$, $R^3$ and $R^9$ are as according to any one of embodiments 1-24, and wherein the base guanine may be protected, e.g. with DMF or acyl such as iBu.

44. The method according to any one of embodiments 1-28, wherein the oxazaphospholidine phosphoramidite monomer is selected from the group consisting of a D-LNA-A or a L-LNA-A monomer, such as a oxazaphospholidine phosphoramidite monomer of formula

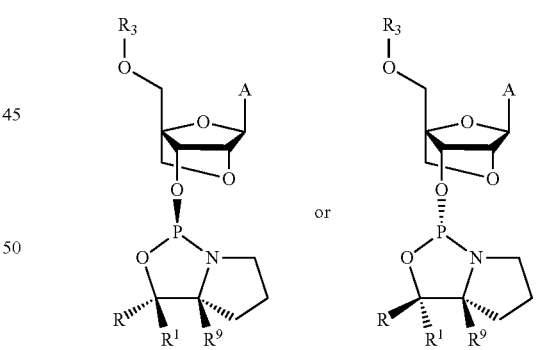

wherein A is adenine, and wherein R, $R^1$, $R^3$ and $R^9$ are as according to any one of embodiments 1-24, wherein the base adenine may be protected, e.g. with benzoyl.

45. The method according to any one of embodiments 1-28, wherein the oxazaphospholidine phosphoramidite monomer is selected from the group consisting of a D-LNA-T or a L-LNA-T monomer, such as a oxazaphospholidine phosphoramidite monomer of formula

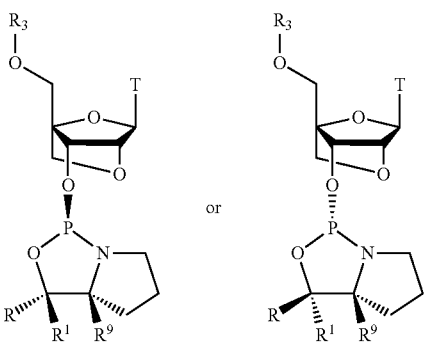

wherein T is thymine, and wherein R, $R^1$, $R^3$ and $R^9$ are as according to any one of embodiments 1-24.

46. The method according to any one of embodiments 1-28, wherein the oxazaphospholidine phosphoramidite monomer is selected from the group consisting of a D-LNA-C or a L-LNA-C monomer, such as a oxazaphospholidine phosphoramidite monomer of formula

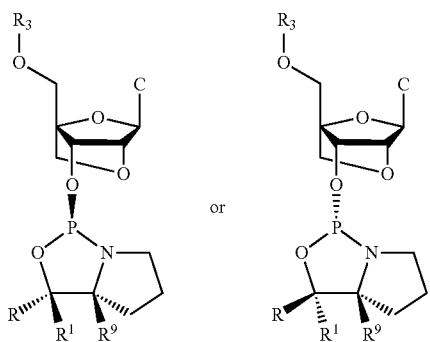

wherein C is cytosine, and wherein R, $R^1$, $R^3$ and $R^9$ are as according to any one of embodiments 1-24, and wherein the base cytosine may be protected, e.g. with benzoyl or acetyl, and wherein optionally cytosine is 5-methyl cytosine.

47. The method according to any one of embodiments 1-28, wherein the oxazaphospholidine phosphoramidite monomer is selected from the group consisting of a D-LNA-G or a L-LNA-G monomer, such as a oxazaphospholidine phosphoramidite monomer of formula

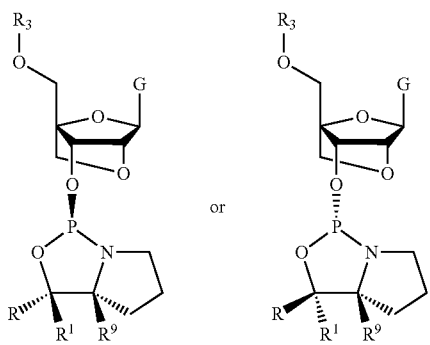

wherein G is guanine, and wherein R, $R^1$, $R^3$ and $R^9$ are as according to any one of embodiments 1-24, and wherein the base guanine is protected with acyl such as iBu for the L-LNA-G monomer, or either acyl (such as iBu) or DMF for the D-LNA-G monomer.

48. The method according to any one of embodiments 1-47 wherein the oxazaphospholidine phosphoramidite monomer is a DNA monomer, or is a LNA monomer selected from the group consisting of a LNA-A monomer, a LNA-C monomer and an acyl protected L-LNA-G monomer.

49. The method according to any one of embodiments 1-47 wherein the oxazaphospholidine phosphoramidite monomer is other than a LNA-T monomer, a D-LNA-G monomer, or a DMF protected L-LNA-G monomer.

50. The method according to any one of embodiments 17-49, wherein R is phenyl, $R^1$ is hydrogen or methyl, $R^9$ is hydrogen, and $R^3$ is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—R—O-MMTr$R^b$, such as $CH_2$—O-DMTr or $CH_2$—O-MMTr.

51. The method according to any one of embodiments 17-49, wherein R is phenyl, $R^1$ is hydrogen or methyl, $R^9$ is hydrogen, and $R^3$ is —$CH_2$—O-DMTr.

52. Use of an acetonitrile solution comprising the oxazaphospholidine phosphoramidite monomer according to any one of embodiments 17-51, acetonitrile and an aromatic heterocyclic solvent, in the coupling step of the method of the invention.

53. The acetonitrile solution according to embodiment 52, wherein the concentration of the oxazaphospholidine phosphoramidite monomer is between about 0.05 M and about 2 M, such as about 0.1 M to about 1 M, such as about 0.1 M-about 0.2M, such as about 0.15 M, or about 0.175 M. or about 0.2 M.

54. The acetonitrile solution according to embodiment 52 or 53, wherein the aromatic heterocyclic solvent is as according to any one of embodiments 1-16.

55. The acetonitrile solution according to any one of embodiments 52-54, wherein the concentration of aromatic heterocyclic solvent in acetonitrile is between about 0.1% and about 50% (v/v), such as between about 0.5% and about 25% (v/v).

56. The acetonitrile solution according to any one of embodiments 52-55, wherein the concentration of aromatic heterocyclic solvent in acetonitrile is between about 0.5% and about 10%, such as between about 1% and about 5% (v/v), such as between about 2-4%, such as about 2.5%, such as about 3.5%.

EXAMPLES

Example 1—General Synthesis Method

To a solution of N-methylmorpholine in toluene (50 mL) $PCl_3$ (2.93 mL 33.4 mmol) was added at −70° C. over a time course of 10 min. Hereafter, proline (PS-D or P5-L) auxillary (6.24 g 35.2 mmol) in toluene (50 mL) was added over 30 min (see J. Am. Chem. Soc., 2008, 130, 16031-16037 for synthesis of P5-D and P5-L). The resulting mixture was stirred at room temperature for 1.5 h after which solvent and volatiles were removed in vacuo (40° C. and 15 mbar). Then, the remaining residue was dissolved in THF (50 mL) and hereafter cooled to −70° C. followed by the addition of first $NEt_3$ (17.8 mL 128 mmol) and then, over 30 min, 5'-ODMT-DNA-Nucleoside (16 mmol) as a solution in THF (50 mL). The reaction mixture was stirred at −77° C. for 30 min and then for 2 h at room temperature. Hereafter, cold EtOAc (200 mL) was added and mixture was washed with cold $NaHCO_3$ (150 mL), brine (150 mL), dried ($Na_2SO_4$), filtered, and evaporated to dryness. The crude product was purified by flash column chromatography under argon with 7% NEt₃ included in the eluent to avoid degradation on silica.

The product was obtained as a solid potentially containing small amounts of residual solvents from e.g. EtOAc, THF, and NEt₃.

Using the above procedure, the following monomers were synthesized:

D-DNA A: 31P NMR (160 MHz, DMSO-d6): δ 150.3
L-DNA A: 31P NMR (160 MHz, DMSO-d6): δ 148.5
D-DNA T: 31P NMR (160 MHz, DMSO-d6): δ 151.0
L-DNA T: 31P NMR (160 MHz, DMSO-d6): δ 149.1
D-DNA C: 31P NMR (160 MHz, DMSO-d6): δ 151.7
L-DNA C: 31P NMR (160 MHz, DMSO-d6): δ 149.8
D-DNA G-DMF: 31P NMR (160 MHz, DMSO-d6): δ 151.7
L-DNA G-DMF: 31P NMR (160 MHz, DMSO-d6): δ 150.3

Example 2

Synthesis of D-LNA-G-DMF

5'-ODMT-LNA-G (3.51 g 5.00 mmol) was co-evaporated with pyridine and then with toluene to remove any residual water or other solvents. Then the residue was dissolved in pyridine (10 mL) and THF (10 mL). This solution was added to solution of D-oxazaphospholidine (3.51 g 5.00 mmol), PCl₃ (0.88 mL 10.0 mmol), and NEt₃ (3.50 mL 25.0 mmol) at −77° C. The resulting reaction mixture was then stirred at −77° C. for 15 min and then at 1.5 h at room temperature. Hereafter, EtOAc (150 mL) was added and mixture was washed with cold NaHCO₃ (100 mL) and brine (100 mL), dried using Na₂SO₄, filtered, and finally evaporated together with toluene. The resulting residue was purified by column chromatography (eluent THF in EtOAc form 10% to 30%+ 7% NEt₃) giving D-LNA-G-DMF (3.91 g, estimated yield 84%).

$^1$H NMR (400 MHz, DMSO-d₆): δ 11.42 (1H, s), 8.56 (1H, s), 7.95 (1H, s), 7.49-7.16 (14H, m), 6.90-6.83 (4H, m), 5.96 (1H, s), 5.58 (1H, d, J=6.7 Hz), 3.87 (1H, d, J=8.1 Hz), 3.72 (6H, s), 3.62-3.54 (1H, m), 3.45 (2H, s), 3.40-3.33 (1H, m), 3.08 (3H, s), 2.99 (3H, s), 2.93-2.84 (1H, m), 1.53-1.39 (2H, m), 1.06-0.97 (1H, m), 0.79-0.63 (1H, m).
$^{31}$P NMR (160 MHz, DMSO-d₆): δ 151.6
LRMS (ESI) m/z [M+H]⁺ calcd for C₄₆H₄₉N₇O₈P: 858.3. Found: 858.7.

Example 3

Synthesis of L-LNA-G-DMF

5'-ODMT-LNA-G (4.91 g 7.00 mmol) was co-evaporated with pyridine and then with toluene to remove any residual water or other solvents. Then the residue was dissolved in pyridine (10 mL) and THF (15 mL). This solution was added to solution of L-oxazaphospholidine (2.48 g 14.0 mmol), PCl₃ (1.22 mL 14.0 mmol), and NEt₃ (4.90 mL 35.0 mmol) at −77° C. The resulting reaction mixture was then stirred at −77° C. for 15 min and then at 1.5 h at room temperature. Hereafter, EtOAc (150 mL) was added and mixture was washed with cold NaHCO₃ (100 mL) and brine (100 mL), dried using Na₂SO₄, filtered, and finally evaporated together with toluene. The resulting residue was purified by column chromatography (eluent THF in EtOAc/DCM 1:1 using a gradient from 15% to 25%+7% NEt₃) giving D-LNA-G-DMF (3.41 g, estimated yield 84%). The product was purified by column chromatography as described above.

$^1$H NMR (400 MHz, DMSO-d₆): δ 12.3-11.9 (1H, br s), 11.8-11.5 (1H, br s), 8.05 (1H, s), 7.45-7.40 (2H, m), 7.35-7.21 (10H, m), 7.02-6.97 (2H, m), 6.92-6.86 (4H, m), 5.94 (1H, s), 5.09 (1H, d, J=6.5 Hz), 4.88 (1H, d, J=7.5 Hz), 4.69 (1H, s), 3.89-3.81 (2H, m), 3.74 (3H, s), 3.73 (3H, s), 3.71-3.64 (1H, m), 3.48-3.38 (3H, m), 2.83-2.73 (1H, m), 2.71-2.64 (1H, m), 1.55-1.45 (2H, m), 1.14-1.05 (1H, m), 1.08 (3H, d, J=6.9 Hz), 1.05 (3H, d, J=6.9 Hz), 0.76-0.66 (1H, m).
$^{31}$P NMR (160 MHz, DMSO-d₆): δ 148.7
LRMS (ESI) m/z [M+H]⁺ calcd for C₄₇H₅₀N₆O₉P: 873.3. Found: 873.7.

Example 4

Synthesis of D-DNA G-DMF

To a solution of N-methylmorpholine in toluene (50 mL) was PCl₃ (2.93 mL 33.4 mmol) added at −70° C. over a time course of 10 min. Hereafter P5-D (6.24 g 35.2 mmol) in toluene (50 mL) was added over 30 min. The resulting reaction mixture was stirred at room temperature for 1.5 h after which solvent and volatiles were removed in vacuo (40° C. and 15 mbar). Then, the remaining residue was dissolved in THF (50 mL) and hereafter cooled to −70° C. followed by the addition of first NEt$_a$ (17.8 mL 128 mmol) and then, over 30 min, 5'-ODMT-DNA-G (9.99 g 16.0 mmol) as a solution in THF (50 mL). The reaction mixture was stirred at −77° C. for 30 min and then for 2 h at room temperature. Hereafter, cold EtOAc (200 mL) was added and mixture was washed with cold NaHCO₃ (150 mL), brine (150 mL), dried (Na₂SO₄), filtered, and evaporated to dryness. The crude product was purified by flash column chromatography under argon (eluent DCM/EtOAc=2/1+7% NEt₃). D-DNA-G-DMF was isolated as a white foam (10.6 g, 72%) with traces of solvent impurities (EtOAc, toluene, and NEt₃).

$^1$H NMR (400 MHz, DMSO-d₆): δ 11.36 (1H, s), 8.52 (1H, s), 7.96 (1H, s), 7.40-7.16 (14H, m), 6.83-6.77 (4H, m), 6.27 (1H, t, J=6.4 Hz), 5.65 (1H, d, j=6.5 Hz), 5.08-5.01 (1H, m), 4.02-3.98 (1H, m), 3.91-3.83 (1H, m), 3.71 (6H, s), 3.45-3.35 (1H, m), 3.27-3.18 (2H, m), 3.07 (3H, s), 3.00 (3H, s), 2.97-2.88 (2H, m), 2.49-2.40 (1H, m), 1.58-1.48 (1H, m), 1.47-1.38 (1H, m), 1.16-1.09 (1H, m), 0.86-0.76 (1H, m).
$^{31}$P NMR (160 MHz, DMSO-d₆): δ 151.7
LRMS (ESI) m/z [M−H]⁻ calcd for C₄₅H₄₇N₇O₇P: 828.3. Found: 828.6.

Example 5

Synthesis of L-DNA G-DMF

To solution of N-methylmorpholine in toluene (25 mL) was PCl3 (1.33 mL 15.2 mmol) during 5 minutes added at −55° C. followed with the addition of P5-L (2.84 g 16.00 mmol) in toluene (25 mL) during 15 min. The resulting reaction mixture was stirred at −55 to −45° C. for 10 min and then at 1.5 h at room temperature. Then, the solvent and other volatiles were removed in vacuo (40° C. and 6 mbar). The remaining residue was then dissolved in THF (25 mL) and cooled to −77° C. Hereafter, NEt3 (8.92 mL 64 mmol) was added followed by a solution of 5'-ODMT-DNA-G-DMF (4.5 g, 7.2 mmol) in THF (25 mL) during 15 min. The reaction mixture was stirred at −77° C. for 15 min and then at 3 h at room temperature. Hereafter, EtOAc (150 mL) was added and the mixture was extracted with cold NaHCO₃ (100 mL), brine (50 mL), dried (Na2SO4), filtered, and evaporated.

The product was isolated by flash column chromatography under argon (eluent EtOAc/DCM=1/2+7% NEt$_3$) as a white foam (3.77 g, 63%) together with traces of EtOAc.

$^1$H NMR (400 MHz, DMSO-d$_6$): δ 11.36 (1H, s), 8.51 (1H, s), 7.96 (1H, s), 7.39-7.11 (14H, m), 6.80-6.73 (4H, m), 6.28 (1H, t, J=6.5 Hz), 5.72 (1H, d, j=6.5 Hz), 5.06-4.96 (1H, m), 4.02-3.95 (1H, m), 3.84-3.76 (1H, m), 3.70 (3H, s), 3.69 (3H, s), 3.50-3.39 (1H, m), 3.27-3.18 (2H, m), 3.08 (3H, s), 3.02 (3H, s), 2.98-2.83 (2H, m), 2.48-2.39 (11H, m), 1.58-1.40 (2H, m), 1.12-1.02 (1H, m), 0.83-0.71 (1H, m).

$^{31}$P NMR (160 MHz, DMSO-d$_6$): δ 150.3

LRMS (ESI) m/z [M+H]$^+$ calcd for C$_{45}$H$_{49}$N$_7$O$_7$P: 830.3. Found: 830.6.

Example 6

Synthesis of L-LNA-G-Ibu Monomers
Procedure for the Synthesis of 5'-OAP-LNA-G-iBu Derivatives

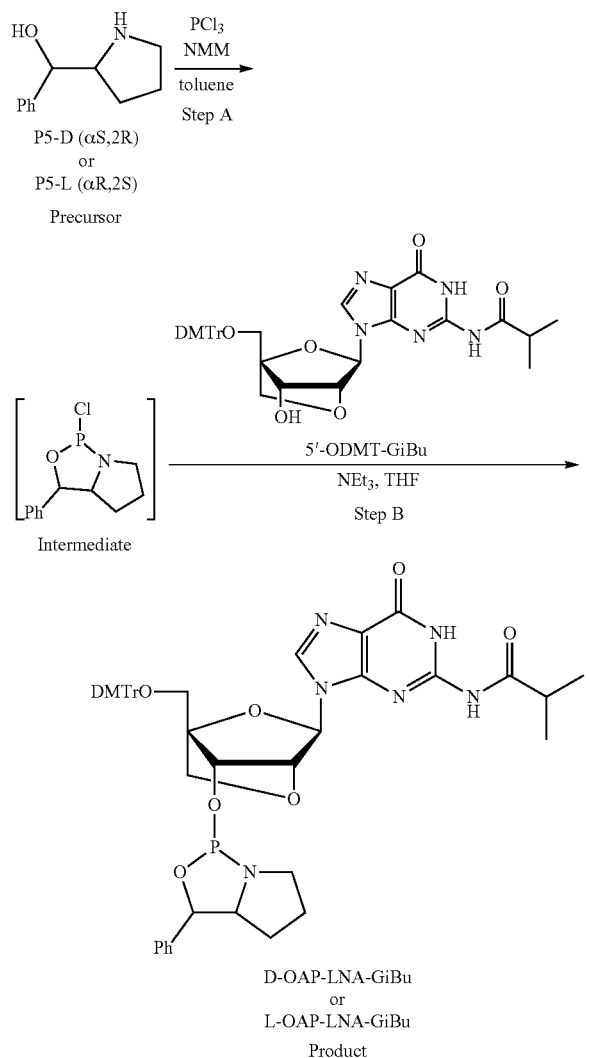

Step A: To a solution of N-methylmorpholine (1.76 mL 16.0 mmol) in toluene (15 mL) was added PCl$_6$ (0.66 mL 7.6 mmol) over 5 min at −55° C. Hereafter, a solution of (S)-phenyl-(R)-pyrolidin-2yl)methanol (P5-D) (1.42 g 8.00 mmol) in toluene (12 mL) was added during the next 15 min. Then, the reaction mixture was stirred for 10 min between −55 to −45° C. and then at room temperature for 1.5 h.

Solvents and other volatile compounds were removed in vacuo at 40° C. and 6 mbar after which THF (13 mL) was added.

Step B: This was followed by a cooling of the reaction mixture to −77° C. whereafter triethylamine (5.54 mL, 40 mmol) was added followed by a solution of 5'-ODMT-LNA-G-iBu (2.67 g, 4 mmol) in THF (13 mL) over 15 min. The resulting mixture was stirred for 15 min at −77° C. and then at room temperature for 3 h. Hereafter, EtOAc (75 mL) was added and the mixture was washed with cold NaHCO$_3$ (50 mL) and brine (50 mL), dried using Na$_2$SO$_4$, filtered, and evaporated in vacuo. The crude product was purified by flash column chromatography under Ar (EtOAc:hexane, 1:4+7% NEt$_3$).

The product was obtained as a white foam (1.95 g, estimated yield of 55%).

$^{31}$P-NMR in DMSO 148.8 ppm+1% at 28.8 ppm.

Additional optimization of the synthesis for both D-LNA G-iBu and L-LNA G-Bu

| No. | St. m. | molar ratio P5:PCl$_3$:5'-ODMT-LNA-G-iBu | 5'-ODMT-LNA-G-iBu, mmol | Estimated yield,$^a$ % |
|---|---|---|---|---|
| 1 | P5-L | 2:2:1 | 8.00 | 48 |
| 2 | P5-L | 2:1.9:1 | 4.00 | 55 |
| 3 | P5-D | 2.2:2.1:1 | 7.20 | 64 |
| 4 | P5-L | 2.4:2.4:1 | 8.00 | 64 |
| 5 | P5-L | 2.2:2.1:1 | 8.00 | 68 |

It was found that a slight excess of PCl$_3$ over the precursor (e.g. P5) causes formation of side products that significantly reduce the yield of the product (e.g. OAP-LNA-GiBu). It is therefore desirable to use at least molar equivalents of precursor & PCl$_3$. In some embodiments the molar ratio of precursor to PCl$_3$ in step 1 is, greater than about 1, such as 1.05 of above. In some embodiments the molar ratio of precursor to PCl$_3$ in step 1 is no greater than 1.5.

It was found that the use of over two fold molar equivalents of the intermediate in step 2 gave the highest yield of product (see table, entries 3 and 5). In some embodiments the molar ratio of intermediate (e.g. 5'-ODMT-G/iBu) to the precursor and PCl$_3$ is greater than 2.

The purity of the products was determined from $^{31}$P-NMR spectra.

Example 7

Determination of Stability and Solubility of Products

To investigate the stability and solubility of L-LNA G-DMF and L-LNA G-i-Bu the following experimental procedure was followed:

To a 1.5 mL vial was added 0.013 mmol of amidite after which the solid material was dissolved in 0.13 mL of solvent. Hereafter, the vial was capped, vortexed, and finally left at room temperature for 24 hours. Then, the dissolved material was visually examined regarding the solubility (FIG. 1). If the solution appeared cloudy or otherwise non-homogenous the solubility was set to "no". If the solution appeared completely homogenous the solubility was set to "yes" (examination repeated after 24 hours).

Stability Determination Method: To complete the analysis the stability of the amidite was investigated using an Agilent 1100 series HPLC-MS with a gradient from 80% A (1% NH$_4$OH in H$_2$O) to 100% B (20% A in MeCN) and a Waters Xterra MS C18 2.1×100 mm column. The mass and UV peak of the mother compound was identified at 0 hours and at 24 hours. Hereafter, the relative stability compared to other by-products was reported by integrating the UV chromatogram (254 nm) and normalizing the area to the chromatogram recorded at 0 hours (FIG. 2).

Figure 3B:
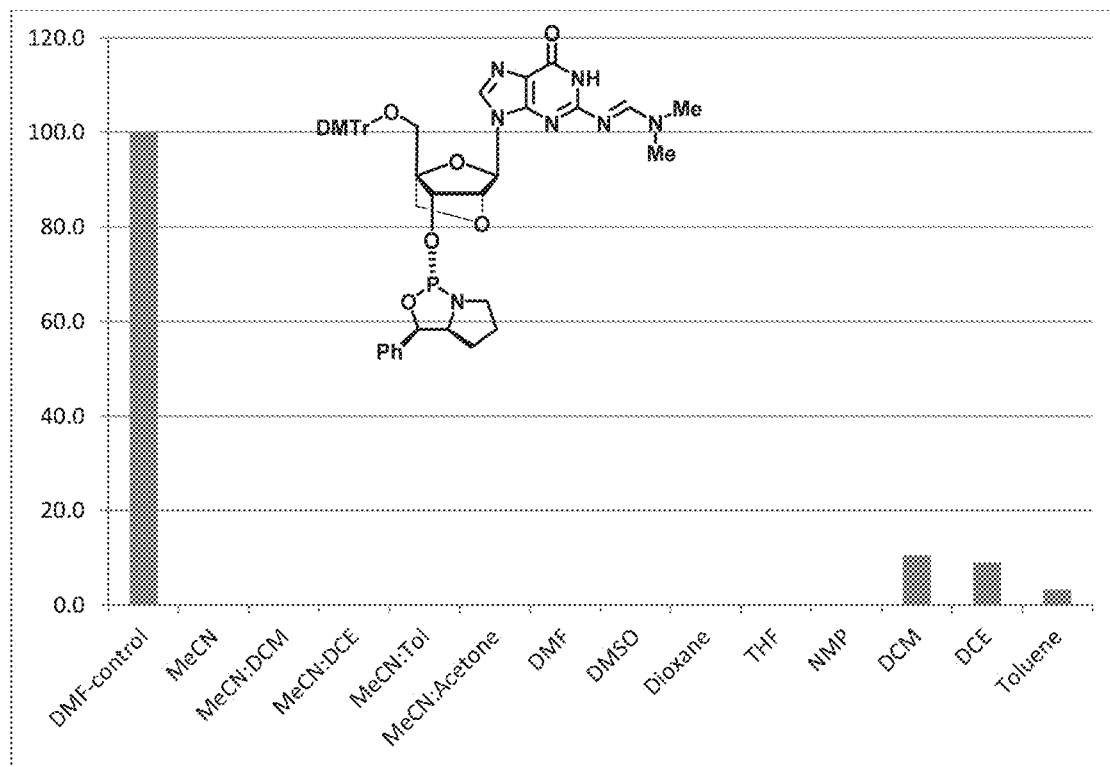

The solubility data at 0 hours and 24 hours after synthesis for the three monomers is illustrated in FIG. 1. The stability data measured after 24 hours in various solvents is shown in FIG. 2 and FIG. 3a (L-LNA-G-iBu) and 3b (L-LNA-G-DMF).

The monomer L-LNA G-DMF is unsoluble in most solvents (MeCN, MeCN:DCE, MeCN:Tol, MeCN:acetone, Dioxane, and THF). The solvents where the monomer is soluble (MeCN:DCM, DMF, DMSO, NMP, DCM, DCE, and Toluene) shows a tremendous instability. The best solvent being DCM with 10% left of the amidite after 24 hours.

The monomer L-LNA G-i-Bu is soluble in all solvents investigated (12 different) with the best performing being MeCN, MeCN:acetone, DCM, and DCE. All solvents investigated for the L-LNA G-i-Bu monomer shows a significant improvement in solubility and stability.

Example 8 Relative Coupling Efficiency in Model System

Model system: 5'-gcattggtatt(LNA A)cattgttgtttt-3'

In order to retard the coupling efficiency of a conventional LNA phosphoroamidate the LNA A was diluted to 0.025 M in MeCN (with and without 5% pyridine). Hereafter the amidite was used in the model system (5'-gcattggtatt(LNA A)cattgttgtttt-3'). Here the 3' flank was identified in the crude mixture after deprotection and compared to the full length product in order to obtain a relative coupling efficiency for the monomer in question, i.e. LNA A 0.025 M and LNA A 0.025 M+5% pyridine.

The results show that the coupling is indeed restarted by reducing the concentration of the monomer in solution. However, it also shows that in the case of LNA A there is a decrease in reactivity with the addition of pyridine (FIG. 4).

Example 9 Triethylamine Stabilisation of Oxazaphospholidine Phosphoramidite Monomer Solutions, but does not Improve Coupling Efficacy Here the stability of L-LNA A in the presence of $Et_3N$ (5-10 eq as compared to amidite) was monitored.

To investigate the stability and solubility of L-LNA A the following experimental procedure was followed.

To a 1.5 mL vial was added 0.013 mmol of amidite after which the solid material was dissolved in 0.13 mL of solvent (with and without $Et_3N$, approximately 5-10 eq). Hereafter, the vial was capped, vortexed, and finally left at room temperature for 24 hours. To investigate the stability of the amidite an Agilent 1100 series HPLC-MS with a gradient from 80% A (1% $NH_4OH$ in $H_2O$) to 100% B (20% A in MeCN) and a Waters Xterra MS C18 2.1×100 mm column was used. The mass and UV peak of the mother compound was identified at 0 hours and at 24 hours. Hereafter, the relative stability compared to other by-products was reported. This was again repeated after 48 hours.

The results (FIG. 5) show that the stability of L-LNA A, only in the presence of MeCN, is very unstable over time. After 24 hours most of the L-LNA A was degraded. After 48 hours the L-LNA A monomer was completely degraded. In the case of L-LNA A in MeCN and in the presence of Et3N (approximately 5-10 eq as compared to the monomer) the L-LNA A is completely stable after 24 hours. After 48 hours L-LNA A is partly, however still the majority of the L-LNA A is preserved in the solution.

Thus, the Et3N stabilizes the amidite in solution. However, using these conditions in the oligonucleotide synthesis only results in trace amounts full length product.

Example 10 Relative Coupling Efficiency in the Model System Using L-LNA a Oxazaphospholidine Phosphoramidite Monomers and a Variety of Different Amine Bases In order to find a suitable base which is tolerated in the coupling step several different additives in the concerning nitrogen containing bases were investigated in the model system (5'-gcattggtatt(LNA A)cattgttgtttt-3').

After global deprotection ($NH_4OH$ at 60° C. overnight) of the oligonucleotide the 3' DNA flank was identified and compared to the full length product in the crude mixture in order to obtain a value for the relative coupling efficiency for the conditions (solvent+/−base) investigated. The results are shown in FIG. 6.

Interestingly, it was found that the conventional oligonucleotide synthesis solvent MeCN in itself resulted in a mediocre relative coupling efficiency of 59%. However, in the presence of pyridine the coupling was possible and in some cases resulted in an improved relative coupling efficiency.

By titrating the amount of pyridine needed to obtain a maximum coupling efficiency it was found that an amount between 5 to 1% v/v pyridine in MeCN was optimal.

Furthermore, also pyridine derivatives such as 3-picoline enhanced the coupling efficiency.

Example 11 Relative Coupling Efficiency in the Model System Using a Variety of Oxazaphospholidine Phosphoramidite Monomers and a Variety of Different Solvents In order to investigate the effect of added pyridine to the solvent of the monomer a set of 5 additional monomers were investigated using the model system (5'-gcattggtatt(stereodefined amidite)cattgttgtttt-3').

After global deprotection ($NH_4OH$ at 60° C. overnight) of the oligonucleotide the 3' DNA flank was identified and compared to the full length product in the crude mixture in order to obtain a value for the relative coupling efficiency for the conditions (solvent+/−base) investigated. The results are shown in FIG. 7.

It is seen that the effect of increased reactivity, the addition of pyridine, is not general among all monomers. Interestingly, specific monomers, like D-DNA A, benefit from the pyridine in terms of increased relative coupling yield.

In other cases the results are comparable with and with out pyridine, as in the case w. L-DNA A. However, looking at the properties of solubility, MeCN by itself is not sufficient to keep the monomer in solution over a time period of 24 hours. With the addition of 2.5% pyrindine the monomer is kept in solution over a time period of 24 hours.

Example 12 Solubility of Various Oxazaphospholidine Phosphoramidite Monomers in MeCN+/−2.5% Pyridine, and Stability of the Solutions Solubility of the following monomers was determined as per example 7.

| Soluble after: | 0 h MeCN + 2.5% pyridine | 24 h MeCN + 2.5% pyridine | 0 h MeCN | 24 h MeCN |
|---|---|---|---|---|
| D-DNA A | Yes | Yes | Yes | No |
| L-DNA A | Yes | Yes | Yes | No |
| D-DNA T | Yes | Yes | Yes | No |
| L-DNA T | Yes | Yes | Yes | No |
| D-DNA C | Yes | Yes | Yes | No |
| L-DNA C | Yes | Yes | Yes | No |
| D-DNA G | Yes | Yes | Yes | No |
| L-DNA G | Yes | Yes | Yes | No |
| D-LNA A | Yes | Yes | Yes | No |
| L-LNA A | Yes | Yes | Yes | No |
| D-LNA T | Yes | Yes | Yes | Yes |
| L-LNA T | Yes | Yes | Yes | Yes |
| D-LNA C | Yes | Yes | Yes | No |
| L-LNA C | Yes | Yes | Yes | No |
| D-LNA G | Yes | Yes | Yes | Yes |
| L-LNA G-DMF | No | No | No | No |
| L-LNA-G-iBu | Yes | Yes | Yes | no |

DNA A is Bz protected, DNA C is acetyl (Ac) protected, DNA T no protecting group, DNA G is DMF, LNA A is Bz protected, LNA C is Bz, LNA T no protecting group, LNA G is DMF (D-LNA) and Ibu (L-LNA). Bz=benzoyl.

Unless indicated all monomers have DMF protected nucleobases, with the exception of L-LNA-G-iBu, which has an isobutyryl protection group.

Further testing additional monomers reveals that the solubility enhancing effect of the addition of pyridine is general across the series of monomers. As in the case of D-LNA A, D-DNA A and, L-DNA A these monomers are not soluble after 24 hours in MeCN. However with the addition of pyridine the solubility of the monomer is preserved. The enhancement in reactivity is also seen for D-DNA A and L-LNA T while L-DNA A and D-LNA A reacts in a comparable manner.

Example 13 Conversion of Full Length Product with and without 2.5% Pyridine and with Various Activation Concentrations The relative coupling conversions as obtained in the model system 5'-Xttttttttttttttt-3'—with X=L-LNA A. The unreacted fragment (5'-ttttttttttttttt-3') and the full length product (i.e. 5'-(L-LNA-A)ttttttttttttttt-3') is integrated and compared relative to each other in order to obtain the relative coupling efficiency in the system. Different concentrations of activator was used in order to determine the optimal concentrations. The addition of pyridine clearly enhances the coupling efficiency as relative to the couplings whereby no pyridine is present. As can be seen by the results (FIG. 8), irrespective of activator concentration, the addition of pyridine has in general, a benefit in terms of an increased conversion ratio. It is also apparent, as is routine in the art, that the concentration of activator should be optimised, and with regards DCI, it is typically used at a concentration of 1M DCI with 0.1M NMI. Using the obtained conversions to full length product a number of theoretical yields were calculated. Here it is evident that the addition of pyridine is crucial in order to obtain useful yields which can be used for drug discovery. Given the coupling efficacy data obtained experimentally, it is possible the theoretic yields for a 13mer oligonucleotide are shown in FIG. 9, and for a 16mer oligonucleotide see FIG. 10. The data is provided in the table below:

Table of actual conversions to full length products together with the theoretical yields of 13 and 16 mers.

| Molarity of activator | over all yield 13mer no pyridine | over all yield 16mer no pyridine | over all yield 13mer with pyridine | over all yield 16mer eith pyridine |
|---|---|---|---|---|
| 1.6M DCI + 0.16M NMI | 0.020326 | 0.002858 | 4.668229 | 2.301619 |
| 1.5M DCI + 0.15M NMI | 4.21E−08 | 2.88E−10 | 16.35876 | 10.77229 |
| 1.4M DCI + 0.14M NMI | 0.00718 | 0.000794 | 0.012207 | 0.001526 |
| 1.3M DCI + 0.13M NMI | 0.012207 | 0.001526 | 0.000925 | 6.38E−05 |
| 1.2M DCI + 0.12M NMI | 1.59E−05 | 4.30E−07 | 0.012207 | 0.001526 |
| 1.1M DCI + 0.11M NMI | 1.49E−06 | 2.33E−08 | 0.015791 | 0.002095 |
| 1M DCI + 0.1M NMI | 1.67185 | 0.650378 | 21.98215 | 15.49673 |
| 0.9M DCI + 0.09M NMI | 0.084055 | 0.0164 | 14.07602 | 8.953137 |
| 0.8M DCI + 0.08M NMI | 0.246279 | 0.061581 | 4.298387 | 2.079287 |
| 0.7M DCI + 0.07M NMI | 0.161915 | 0.036752 | 6.461082 | 3.433684 |
| 0.6M DCI + 0.06M NMI | 0.005461 | 0.000567 | 1.165087 | 0.416998 |
| 0.5M DCI + 0.05M NMI | 1.59E−05 | 4.30E−07 | 1.397406 | 0.521579 |
| 0.4M DCI + 0.04M NMI | 0.000171 | 7.96E−06 | 4.668229 | 2.301619 |
| 0.3M DCI + 0.03M NMI | 2.822128 | 1.238846 | 0.200029 | 0.047672 |
| 0.2M DCI + 0.02M NMI | 8.11E−05 | 3.19E−06 | 0.000344 | 1.89E−05 |
| 0.1M DCI + 0.01M NMI | 2.83E−07 | 3.01E−09 | 0.001265 | 9.38E−05 |
| 0.05M DCI + 0.01M NMI | 2.54E−12 | 1.85E−15 | 7.94E−10 | 2.18E−12 |

This data show the marked benefit of using the coupling solvents of the present invention for the synthesis of stereo-defined oligonucleotides.

Example 14: Stereodefined Oligonucleotide Synthesis Improvements

In this example, synthesis of stereochemical variants of the LNA oligonucleotide shown below was performed, using the standard conditions (acetonitrile coupling solvent), and according to the invention:

(SEQ ID NO 1)
5'-$G_{Sp}C_{Sp}a_{Sp}t_{Sp}t_{Sp}g_{Sp}g_{Sp}t_{Sp}a_{Sp}t_{Sp}T_{Sp}C_{Sp}A$-3'

X denote LNA nucleotide
Lowercase letter denote DNA nucleotide
Subscript Sp=stereorandom phosphorothioate internucleoside linkage.

Prior art conditions: 49 compounds were synthesized on 1 µmol scale using acetonitrile as the solvent for the stereo-defined phosphoramidites, and 0.25M DCI as the activator. By using acetonitrile significant issues in relation to instability and solubility of the phosphoramidites was observed, which caused clogging of the lines on the synthesis instrument and low lifetime of the amidite solutions. All syntheses were carried out DMT-ON, meaning that no final acid treatment is taking place on the synthesis instrument. After the synthesis, the oligonucleotides were cleaved from the solid support using concentrated ammonium hydroxide at room temperature. The oligonucleotides were hereafter deprotected by placing the resultant solutions at 60° C. for 24 h. The oligonucleotides were hereafter purified by using DMTr-based reversed phase cartridge purification. After concentration of the oligonucleotides in vacuo, the oligonucleotides were dissolved in 200 μL PBS, and the concentration was determined by optical absorbance at 260 nm, and backcalculated to a concentration using a theoretically calculated extinction coefficient. The average concentrations of the 49 solutions of oligonucleotides was hereby measured to be 391 μM in 200 μL PBS.

New and improved conditions: 192 compounds were synthesized on 1 μmol scale using 3.5% pyridine in acetonitrile as the solvent for the stereodefined phosphoramidites, and 1M DCI+0.1M NMI as the activator. By using this solvent for the stereodefined amidites, no issues in relation to solubility were observed, and furthermore the lifetime of the amidite solutions was seen to be much longer. All syntheses were carried out DMT-ON, meaning that no final acid treatment is taking place on the synthesis instrument. After the synthesis, the oligonucleotides were cleaved from the solid support using concentrated ammonium hydroxide at room temperature. The oligonucleotides were hereafter deprotected by placing the resultant solutions at 60° C. for 24 h. The oligonucleotides were hereafter purified by using DMTr-based reversed phase cartridge purification. After concentration of the oligonucleotides in vacuo, the oligonucleotides were dissolved in 200 μL PBS, and the concentration was determined by optical absorbance at 260 nm, and backcalculated to a concentration using a theoretically calculated extinction coefficient. The average concentrations of the 192 solutions of oligonucleotides was hereby measured to be 1071 μM in 200 μL PBS Thus comparing the solubility and reactivity enhancements across the series we see a factor of 2.7 enhancement of the yield with pyridine compared to the conditions without pyridine.

Example 15: Relative Coupling Efficiency in the Model System Using a Variety of Oxazaphospholidine Phosphoramidite Monomers in Acetonitrile with and without Pyridine In order to investigate the effect of added pyridine to the solvent of the monomer a set of 7 additional monomers were investigated using the model system (5'-gcattggtatt(stereodefined amidite)cattgttgtttt-3').

After global deprotection (NH$_4$OH at 60° C. overnight) of the oligonucleotide the 3' DNA flank was identified and compared to the full length product in the crude mixture in order to obtain a value for the relative coupling efficiency for the conditions (solvent+/−base) investigated. The results are shown in FIG. 19. The results illustrate that in addition to the benefits of improved solubility and stability for all the monomers, the use of coupling solvents comprising heterocyclic base solvents, such as pyridine, provides a marked improvement in coupling efficacy of D-DNA-C, L-LNA-C and L-LNA-G monomers, in addition to L-LNA-T and D-DNA-A monomers (see FIG. 7). In addition, the results illustrate that the presence of pyridine does not adversely effect the coupling efficacy of other monomers.

Example 16: Evaluation of Repeated Coupling on Yield of the Stereodefined Oligonucleotide Oligonucleotides were synthesized on a MerMade12 instrument in 1 μmol scale on unylinker CPG solid support.

Stereodefined linkages were introduced by oxazaphospholidine phosphoramidite monomers, as in FIGS. 12 and 14. These were dissolved in 3.5% pyridine in acetonitrile at a concentration of 0.1M. Stereorandom linkages were introduced via s-cyanoethyl phosphoramidites that were dissolved in acetonitrile at a concentration of 0.1M.

3% Dichloroacetic acid in dichloromethane was used for detritylation, 1M DCI, 0.1M NMI was used as activator, 0.1M Xanthane Hydride in 1:1 pyridine and acetonitrile was used for sulfurization. Acetonitrile/N-Methylimidazole 8/2 (v/v) was used as CapA and Acetonitrile/Acetic Anhydride/Pyridine 5/2/3 (v/v/v) was used as cap B.

For oligonucleotide synthesis it is often seen that repeated coupling steps prior to oxidation can enhance the coupling efficacy and thereby the oligonucleotide yield. In this example it was investigated whether the use of multiple coupling steps could enhance the coupling conversion in the poly-t model system (5'ttttttttttttttt-3'). For the 16th coupling L-LNA A was used. After deprotection using NH$_4$OH (aq) at 55 C for 24 hours the crude material was analyzed by UPLC. Here the UV of the full length product (at 260 nm) was compared to the non-coupled poly-T fragment. From the integration of these two peaks a relative coupling efficiency was determined. From the data it is seen that repeated coupling has a negative effect on the relative coupling efficiency (FIG. 20). Thus the intermediate trivalent phosphorous might be unstable when exceeding three couplings (FIG. 21).

Example 17: Repeated Coupling and Oxidation Steps within a Single Elongation Cycle Oligonucleotides were synthesized on a MerMade12 instrument in 1 μmol scale on unylinker CPG solid support.

Stereodefined linkages were introduced by oxazaphospholidine phosphoramidite monomers, as in FIGS. 12 and 14. These were dissolved in 3.5% pyridine in acetonitrile at a concentration of 0.1M. Stereorandom linkages were introduced via β-cyanoethyl phosphoramidites, that were dissolved in acetonitrile at a concentration of 0.1M.

3% Dichloroacetic acid in dichloromethane was used for detritylation, 1M DCI, 0.1M NMI in acetonitrile was used as activator, 0.1M Xanthane Hydride in 1:1 pyridine and acetonitrile was used for sulfurization. Acetonitrile/N-Methylimidazole 8/2 (v/v) was used as CapA and Acetonitrile/Acetic Anhydride/Pyridine 5/2/3 (v/v/v) was used as cap B.

To examine the relative coupling efficiency a model system consisting of poly DNA T was set up. Here, the starting point for coupling consisted of 15 DNA-T's (i.e. 5'-ttttttttttttttt-3'). The 16th coupling would then be of the specific monomer examined i.e. the stereodefined L-LNA A amidite. After the coupling the oligonucleotide was globally deprotected using aq. ammonium hydroxide at 55° C. for 24 h. Then, the crude material was analyzed by UPLC. The UV, at 260 nm) of the unreacted 15 DNA T (i.e. 5' ttttttttttttttt3') was compared to the UV of full length product (i.e. 5' L-LNA-A-ttttttttttttttt-3'). The relative difference between these peaks, measured by integration of the UV chromatogram, were assigned as the relative coupling efficiency.

In order to investigate the old cycle (in figure denoted "Normal", using a std, coupling (×3), oxidation, wash, DMTr deprotection followed by further elongation steps), three different synthesis were investigated with L-LNA A as the 16th coupling. Hereafter, three synthesis were investigated with the new coupling cycle thus having an oxidation step between every coupling step (i.e. coupling, oxidation, wash, coupling, oxidation wash, coupling, oxidation wash, DMTr deprotection, and then followed by further elongation steps). The obtained relative coupling efficiencies can be seen in FIGS. 22 and 23. Here it is evident that the "normal" cycle is inferior to the new and improved "COWCOW-cycle".

Summarizing these results it is determined that the differences seen are significant.

Example 18

Examples of yields for fully stereodefined oligonucleotides using the "COWCOW" cycle.

Oligonucleotides were synthesized on a MerMade12 instrument in 1 µmol scale on unylinker CPG solid support.

Stereodefined linkages were introduced by oxazaphospholidine phosphoramidite monomers, as in FIGS. 12 and 14. These were dissolved in 3.5% pyridine in acetonitrile at a concentration of 0.1M. Stereorandom linkages were introduced via β-cyanoethyl phosphoramidites, that were dissolved in acetonitrile at a concentration of 0.1M.

3% Dichloroacetic acid in dichloromethane was used for detritylation, 1M DCI, 0.1M NMI in MeCN was used as activator, 0.1M Xanthane Hydride in 1:1 pyridine and acetonitrile was used for sulfurization. Acetonitrile/N-Methylimidazole 8/2 (v/v) was used as CapA and Acetonitrile/Acetic Anhydride/Pyridine 5/2/3 (v/v/v) was used as cap B.

In this example 19 oligos targeting Hif-1-alpha mRNA were synthesized on a 1 µmol scale. The design of the oligo was: 13mer, gapmer design, 4 LNAs, and 9 DNAs. All synthesized with a stereodefined phosphorothioate backbone. The oligos were synthesized using three repeats of the "coupling-oxidation-wash"-cycle.

Out of the 19 oligos synthesized 16 of these had a superior isolated yield of 32% with an average purity of 77%. The remaining 3 oligos were determined to have failed in the synthesis as their yield were an average of 6%. Taking all data points into consideration the average yield was 28%. Thus, the yield was enhanced (factor of 3) compared to using the "normal cycle" (i.e. from 10% isolated yield to 28% average isolated yield).

Example 19: Further Investigations of the Enhanced Yield

Oligonucleotides were synthesized on a MerMade192 instrument in 1 µmol scale on unylinker CPG solid support.

Stereodefined linkages were introduced by oxazaphospholidine phosphoramidite monomers, as in FIGS. 12 and 14. These were dissolved in 3.5% pyridine in acetonitrile at a concentration of 0.1M. Stereorandom linkages were introduced via β-cyanoethyl phosphoramidites, that were dissolved in acetonitrile at a concentration of 0.1M.

3% Trichloroacetic acid in dichloromethane was used for detritylation, 1M DCI, 0.1M NMI in MeCN was used as activator, 0.1M Xanthane Hydride in 1:1 pyridine and acetonitrile was used for sulfurization. Acetic Anhydride/Tetrahydrofurane 9.1/90.9 (v/v) was used as CapA and Tetrahydrofurane/N-Methylimidazole/Pyridine 8/1/1 (v/v/v) was used as cap B.

To validate the invention of the COWCOW-cycle the data set was expanded to cover in total 92 oligos. The oligo was chosen as a 16mer LNA gapmer. All of these were synthesized with the "normal cycle" and with the "COWCOW-cycle". In this example only two repeats of the "coupling-oxidation-wash"-cycle was carried out.

The results showed a 50% improvement in yield. The "normal-cycle" gave an average isolated yield of 12% whereas the improved "COWCOW-cycle" gave an average isolated yield of 17%. Thus with only two repeats of the "COW"-cycle a 50% improvement in yield was obtained.

Average yields old cycle: 12%
Average yields new cycle: 17%
Increase in coupling yield: 50%

Example 20—Analysis of Coupling Efficiency

The relative coupling conversions as obtained in the model system 5'-Xtttttttttttttt-3' (X=L-LNA$^m$C) or 5'-Xtttttttt-3' (X=L-DNA T). t is stereorandom DNA T. All linkages are phosphorothioates.

The unreacted fragment and the full length product is integrated after UPLC analysis and compared relative to each other in order to obtain the relative coupling efficiency in the system. The synthesis was carried out on an Akta 100 synthesizer in 200 µmol scale on Unylinker polystyrene solid support.

Stereodefined linkages were introduced by oxazaphospholidine phosphoramidite monomers, as in FIGS. 12 and 14. These were dissolved in 3.5% pyridine in acetonitrile at a concentration of 0.15M. Stereorandom linkages were introduced via β-cyanoethyl phosphoramidites, that were dissolved in acetonitrile at a concentration of 0.2M.

2 equivalents was used for each coupling with a coupling time 10 minutes for all phosphoramidites.

3% Dichloroacetic acid in dichloromethane was used for detritylation, 1M DCI, 0.1M NMI in MeCN was used as activator, 0.1M Xanthane Hydride in 1:1 pyridine and acetonitrile was used for sulfurization. Acetonitrile/N-Methylimidazole 8/2 (v/v) was used as CapA and Acetonitrile/Acetic Anhydride/Pyridine 5/2/3 (v/v/v) was used as cap B.

After synthesis had completed the solid support was suspended in concentrated ammonia for 24 hours. The solid support was removed and ammonia evaporated in vacuo prior to evaluation of coupling efficiency on the crude material by UPLC-MS analysis.

For L-DNA T the following results was obtained as seen in FIG. 25

Double coupling: 84.8% coupling conversion
COWCOW: 96% coupling conversion
Overall 13.2% increase in coupling efficiency is seen
For L-LNA C the following results was obtained as seen in FIG. 26
Double coupling: 47.4% conversion
COWCOW: 53.3% conversion
Overall a 12% increase in coupling efficiency is seen

The invention claimed is:

1. A method for the synthesis of a stereodefined phosphorothioate oligonucleotide, comprising the steps of:
   a) deprotecting a protected 5'-hydroxy terminus of a nucleoside, or oligonucleotide, attached to a solid support,
   b) coupling an oxazaphospholidine phosphoramidite monomer to the deprotected 5'-hydroxy terminus of a nucleoside or oligonucleotide, to form a phosphite triester intermediate, wherein said coupling reaction takes place in an acetonitrile solvent composition, wherein the acetonitrile solvent comprises acetonitrile and an aromatic heterocyclic solvent, and wherein the aromatic heterocyclic solvent is pyridine, and the concentration of pyridine in acetonitrile is between about 1% and about 10%,
   c) oxidizing the phosphite triester intermediate with a sulfurizing reagent, followed by an optional washing step,
   d) repeating steps b) and c) within the same elongation cycle,
   e) optionally repeating steps a)-d) for one or more further elongation cycles, and
   f) deprotecting and cleaving the oligonucleotide from the solid support.

2. The method according to claim 1, wherein steps d) is performed at least twice.

3. A method according to claim 1, wherein said method comprises multiple further elongation cycles (e).

4. The method according to claim 1, wherein the oxazaphospholidine phosphoramidite monomer is of Formula 1a or Formula 1b

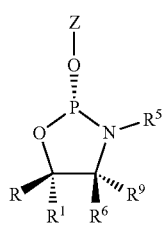

Formula 1a

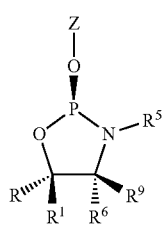

Formula 1b wherein Z is a 3'-O-substitutent derived from a nucleoside, $R^5$ and $R^6$ are independently selected from the group consisting of hydrogen, alkyl, cyclo-alkyl, aryl, N-heteroaryl, substituted alkyl, substituted cyclo-alkyl, substituted aryl, and substituted N-heteroaryl, or $R^5$ and $R^6$ together form a heterocyclic ring consisting of 3-16 carbon atoms, together with the N atom of formula 1a or 1b;

$R^9$ is hydrogen;

$R^1$ is selected from the groups consisting of hydrogen and $C_{1-3}$ alkyl;

R is selected from the groups consisting of aryl, N-heteroaryl, substituted aryl, substituted N-heteroaryl, nitro, halogen, cyano, silyl, substituted silyl, sulfone, substituted sulfone (aryl substituted sulfone), fluorene, and substituted fluorene; and, wherein, when substituted, R, $R^5$, and $R^6$ may be substituted with a group selected from the group consisting of: $C_{1-4}$ alkyl group, $C_{6-14}$ aryl group $C_{1-4}$ alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group, multiple substitutions may be independently selected from the group consisting of: $C_{1-4}$ alkyl group, $C_{6-14}$ aryl group, $C_{1-4}$ alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

5. The method of claim 1, wherein a nucleoside, or oligonucleotide, comprises a 3'-O-substituted DNA, RNA, or LNA monomer, or combination of monomers, containing a nucleobase selected from a group consisting of: 9-adeninyl, 9-guaninyl, 1-cytosinyl, 1-thymidinyl, 1-uracil, 9-xanthinyl, 9-hypoxanthinyl, 1-5-methyl-cytosinyl, 1-isocytosinyl, 1-pseudoisocytosinyl, 1-5-bromo-uracil, 1-5-propynyl-uracil, 9-6-aminopurinyl, 9-2-aminopurinyl, 9-diaminopurinyl, and 9-2-chloro-6-aminopurinyl.

6. The method of claim 1, wherein deprotecting a protected 5'-hydroxy terminus of a nucleoside, or oligonucleotide, attached to a solid support removes a protecting group consisting of: -DMTr or -MMTr.

7. The method according to claim 1, wherein the concentration (v/v), of aromatic heterocyclic solvent in acetonitrile is between about 1% and about 5%.

8. A method for the synthesis of a stereodefined phosphorothioate oligonucleotide, comprising the steps of:
   a) deprotecting a protected 5'-hydroxy terminus of a nucleoside, or oligonucleotide, attached to a solid support,
   b) coupling an oxazaphospholidine phosphoramidite monomer to the deprotected 5'-hydroxy terminus of a nucleoside or oligonucleotide, to form a phosphite triester intermediate, wherein said coupling reaction takes place in an acetonitrile solvent composition, wherein the acetonitrile solvent comprises acetonitrile and an aromatic heterocyclic solvent, wherein the concentration (v/v), of aromatic heterocyclic solvent in acetonitrile is between about 1% and about 10%, and wherein the aromatic heterocyclic solvent is pyridine,
   c) oxidizing the phosphite triester intermediate with a sulfurizing reagent, followed by an optional washing step, d) repeating steps b) and c) within the same elongation cycle, e) optionally repeating steps a)-d) for one or more further elongation cycles, and f) deprotecting and cleaving the oligonucleotide from the solid support.

9. A method for the synthesis of a stereodefined phosphorothioate oligonucleotide, comprising the steps of:

a) deprotecting a protected 5'-hydroxy terminus of a nucleoside, or oligonucleotide, attached to a solid support, b) coupling an oxazaphospholidine phosphoramidite monomer to the deprotected 5'-hydroxy terminus of a nucleoside or oligonucleotide, to form a phosphite triester intermediate, wherein the oxazaphospholidine phosphoramidite monomer is an L-LNA guanine monomer, wherein the exocyclic nitrogen on the guanine residue is protected with an acyl group according to Formula 31 or Formula 32

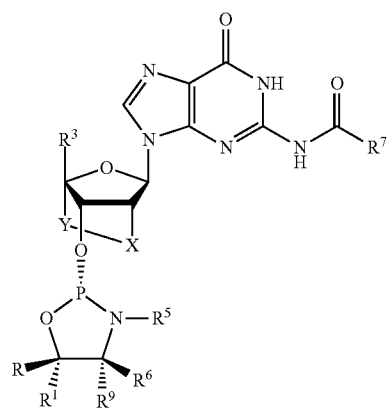

Formula 31

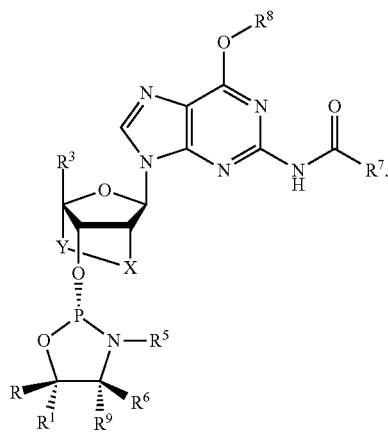

Formula 32 wherein $R^5$ and $R^6$ are independently selected from the group consisting of hydrogen, alkyl, cyclo-alkyl, aryl, N-heteroaryl, substituted alkyl, substituted cyclo-alkyl, substituted aryl, and substituted N-heteroaryl, or $R^5$ and $R^6$ together form a heterocyclic ring consisting of 3-16 carbon atoms, together with the N atom;

$R^9$ is hydrogen;

$R^1$ is selected from the groups consisting of hydrogen and $C_{1-3}$ alkyl;

R is selected from the groups consisting of aryl, N-heteroaryl, substituted aryl, substituted N-heteroaryl, nitro, halogen, cyano, silyl, substituted silyl, sulfone, substituted sulfone (aryl substituted sulfone), fluorene, and substituted fluorene;

wherein, when substituted, R, $R^5$, and $R^6$ may be substituted with a group selected from the group consisting of: $C_{1-4}$ alkyl group, $C_{6-14}$ aryl group $C_{1-4}$ alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group, multiple substitutions may be independently selected from the group consisting of: $C_{1-4}$ alkyl group, $C_{6-14}$ aryl group, $C_{1-4}$ alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group;

$R^3$ is selected from the group consisting of $CH_2$—O-DMTr and $CH_2$—O-MMTr;

X is selected from the group consisting of sulfur and oxygen;

Y is selected from the group consisting of $C_{1-2}$ alkyl and $C_{1-2}$ substituted alkyl;

wherein, when substituted Y may be substituted with a methyl group;

$R^7$ is isobutyryl; and, $R^8$ is cyanoethyl;

wherein said coupling reaction takes place in an acetonitrile solvent composition, wherein the acetonitrile solvent comprises acetonitrile and an aromatic heterocyclic solvent, and wherein the aromatic heterocyclic solvent is pyridine, and the concentration of pyridine in acetonitrile is between a bout 1% a nd a bout 10%, c) oxidizing the phosphite triester intermediate with a sulfurizing reagent, followed by an optional washing step, d) repeating steps b) and c) within the same elongation cycle, e) optionally repeating steps a)-d) for one or more further elongation cycles, and f) deprotecting and cleaving the oligonucleotide from the solid support.

\* \* \* \* \*

SEQUENCE LISTING

<160> NUMBER OF SEQ ID NOS: 6

<210> SEQ ID NO 1
<211> LENGTH: 24
<212> TYPE: DNA

```
<213> ORGANISM: Artificial Sequence
<220> FEATURE:
<223> OTHER INFORMATION: Model antisense oligonucleotide
<220> FEATURE:
<221> NAME/KEY: misc_feature
<222> LOCATION: (12)..(12)
<223> OTHER INFORMATION: n = LNA A (locked nucleic acid)

<400> SEQUENCE: 1
gcattggtat tncattgttg tttt                                          24

<210> SEQ ID NO 2
<211> LENGTH: 23
<212> TYPE: DNA
<213> ORGANISM: Artificial Sequence
<220> FEATURE:
<223> OTHER INFORMATION: Model antisense oligonucleotide

<400> SEQUENCE: 2
gcattggtat tcattgttgt ttt                                           23

<210> SEQ ID NO 3
<211> LENGTH: 16
<212> TYPE: DNA
<213> ORGANISM: Artificial Sequence
<220> FEATURE:
<223> OTHER INFORMATION: Model antisense oligonucleotide
<220> FEATURE:
<221> NAME/KEY: misc_feature
<222> LOCATION: (1)..(1)
<223> OTHER INFORMATION: n = LNA A (locked nucleic acid)

<400> SEQUENCE: 3 ntttttttt tttttt                                                    16

<210> SEQ ID NO 4
<211> LENGTH: 15
<212> TYPE: DNA
<213> ORGANISM: Artificial Sequence
<220> FEATURE:
<223> OTHER INFORMATION: Model antisense oligonucleotide

<400> SEQUENCE: 4
tttttttttt ttttt                                                    15

<210> SEQ ID NO 5
<211> LENGTH: 13
<212> TYPE: DNA
<213> ORGANISM: Artificial Sequence
<220> FEATURE:
<223> OTHER INFORMATION: Model antisense oligonucleotide

<400> SEQUENCE: 5
gcattggtat tca                                                      13

<210> SEQ ID NO 6
<211> LENGTH: 10
<212> TYPE: DNA
<213> ORGANISM: Artificial Sequence
<220> FEATURE:
<223> OTHER INFORMATION: Model antisense oligonucleotide
<220> FEATURE:
```

```
<221> NAME/KEY: misc_feature
<222> LOCATION: (1)..(1)
<223> OTHER INFORMATION: n = LNA T (locked nucleic acid)

<400> SEQUENCE: 6 nttttttttt                                                          10
```